(12) United States Patent
Shima et al.

(10) Patent No.: US 7,186,731 B2
(45) Date of Patent: Mar. 6, 2007

(54) 2-CYANOPYRROLIDINECARBOXAMIDE COMPOUND

(75) Inventors: Ichiro Shima, Osaka (JP); Akio Kuroda, Osaka (JP); Takehiko Ohkawa, Osaka (JP); Toshio Kurosaki, Osaka (JP); Yuki Sawada, Osaka (JP); Aiko Wada, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 110 days.

(21) Appl. No.: 10/975,524

(22) Filed: Oct. 29, 2004

(65) Prior Publication Data

US 2005/0137224 A1 Jun. 23, 2005

(30) Foreign Application Priority Data

Oct. 31, 2003 (AU) ............................... 2003906010
Feb. 25, 2004 (AU) ............................... 2004900961

(51) Int. Cl.
*A61K 31/4439* (2006.01)
*C07D 451/00* (2006.01)

(52) U.S. Cl. ..................... 514/304; 546/127; 546/129; 546/132

(58) Field of Classification Search ................ 546/127, 546/129, 132; 514/304
See application file for complete search history.

(56) References Cited

U.S. PATENT DOCUMENTS

2005/0176771 A1* 8/2005 Hayakawa et al. ......... 514/326

FOREIGN PATENT DOCUMENTS

WO WO 03/057144 A2 7/2003
WO WO 03/057666 A2 7/2003
WO WO 2003057666 A2 * 7/2003

* cited by examiner

*Primary Examiner*—Kamal A. Saeed
*Assistant Examiner*—Nyeemah Grazier
(74) *Attorney, Agent, or Firm*—Oblon, Spivak, McClelland, Maier & Neustadt, P.C.

(57) ABSTRACT

A compound of the formula (I) or a pharmaceutically acceptable salt thereof:

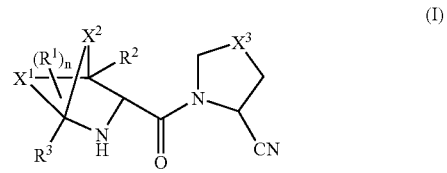

[wherein
$X^1$ and $X^2$ each is independently lower alkylene;
$X^3$ is $=CH_2$, $=CHF$ or $=CF_2$;
$R^1$ is substituent,
$R^2$ and $R^3$ each is independently H or lower alkyl;
n is 0, 1, 2, 3 or 4.]
having the activity inhibiting DPP-IV activity. They are therefore useful in the treatment of conditions mediated by DPP-IV, such as NIDDM.

27 Claims, No Drawings

2-CYANOPYRROLIDINECARBOXAMIDE COMPOUND

TECHNICAL FIELD

This invention relates to the compound and pharmaceutically acceptable salt thereof which inhibit dipeptidyl peptidase-IV (DPP-IV).

Moreover, this invention relates to medicament or pharmaceutical composition comprising the above-mentioned compound or pharmaceutically acceptable salt thereof as an active ingredient, a method for treatment and/or prevention of NIDDM, use of the above compound, and the like.

BACKGROUND ART

It is known that DPP-IV has various physiological functions in living body, especially has the action which inactivates Glucagon-like peptide-1 (GLP-1) by cleaving the terminal dipeptide (His-Ala) and decomposes some cytokines. That is, the resultant peptide is the receptor antagonist of GLP-1 and totally reduces the activity of GLP-1.

This GLP-1 has very important role in sugar metabolism. For example, (1) GLP-1 intensifies the secretion of insulin, (2) express genes which are indispensable for the secretion of insulin, (3) stimulate proliferation of β-cell, (4) suppresses secretion of glucagon, (5) suppresses the function about secretion and motility of digestive organs (especially, peristalsis), and (6) suppresses appetite. That is, GLP-1 restricts food ingestion, postpones the process of digestion and absorption, and raised the use of the sugar in blood.

Therefore, the inhibitor of DPP-IV can maintain the activity of GLP-1, so it is expected as a medicine to treat and prevent various diseases, especially non-insulin dependent diabetes mellitus (NIDDM).

Hitherto, such inhibitors of DPP-IV are known so far. For example in U.S. Pat. Nos. 6,011,155 and 6,124,305, 2-cyanopyrrolidine compounds having [3.1.1]bicyclo moiety like following are disclosed.

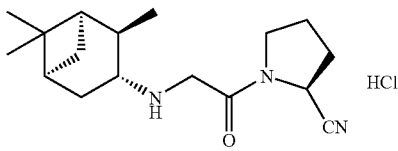

Pyrrolidine, 1-[(2,6,6-trimethylbicyclo[3.1.1]hept-3-yl)amino]acetyl-2-cyano, (S)[1S[1α,2β,3α(S),5α]] monohydrochloride However, the azabicyclo structure of Compound (I) of the present invention is not described in this prior art.

In WO 00/34241, 2-cyanopyrrolidine compounds having substituted adamantyl structure like following are disclosed.

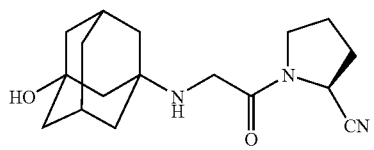

"LAF-237"

Pyrrolidine, 1-[(3-hydroxy-1-adamantyl)amino]acetyl-2-cyano, (S)

However, adamantyl structure is different from the azabicyclo structure of Compound (I) of the present invention.

In WO 03/57666, the azabicyclo compound as following is described.

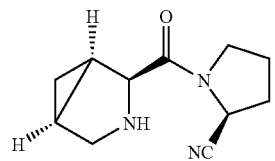

However, the azabicyclo structure of Compound (I) of the present invention is not described.

The hydroxypyrroridine compound like following is described in WO 02/14271.

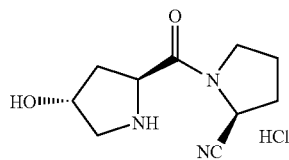

In this document, however, the azabicyclo structure of Compound (I) of the present invention is not described.

WO 02/38541 discloses 2-cyanopyrrolidine compound. However, the azabicyclo structure of Compound (I) of the present invention is not described.

WO 03/074500 discloses (2S,4S)-4-fluoro-1-(2-{[8-(2-pyrazinyl)-8-azabicyclo[3.2.1]oct-3-yl]amino}acetyl)-2-pyrrolidinecarbonitrile dihycrochloride as Example 2.

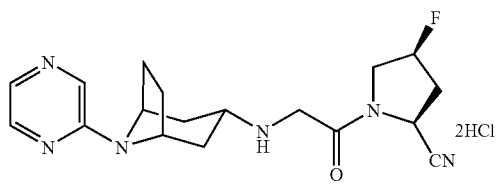

By comparison of this compound and Compound (I) of the present invention, the position of nitrogen atom in azabicyclo structure is different, and pyrrolidine ring is connected to azabicyclo structure by the intermediary of only carbonyl group in Compound (I). Compound (1) of the present invention is different from this compound in that Compound (1) is substituted at 3-position of azabicyclo structure.

WO 03/002553 discloses piperidine compounds such as (2S,4S)-4-fluoro-1-({[1-(isopropylsulfonyl)-4-piperidinyl]amino}acetyl)-2-pyrrolidinecarbonitrile hydrochloride.

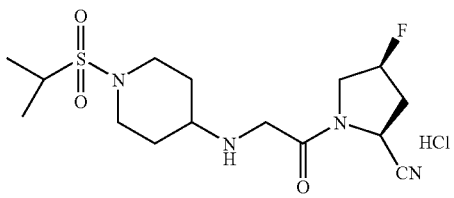

However, the compounds described in the prior art are substituted by sulfonyl group at the nitrogen atom of piperidine ring.

The pyrroridine compound having piperidine ring substituted by the substituent except sulfonyl group is described in WO 02/30890. However, the pyrroridine ring of this compound is not substituted by fluorine atom, compared with Compound (1) of the present compound.

In U.S. Pat. No. 6,172,081, DPP-IV inhibitor having tetrahydroisoquinoline and pyrrolidine structure is described. This compound is obviously different from Compound (2) having tetrahydroquinoline structure.

DISCLOSURE OF INVENTION

Under the above situation, the inventors of this invention found that the compound of this invention (especially, the compound having specific azabicyclo structure) has the outstanding activity to inhibit DPP-IV, and the inventors completed this invention.

Accordingly, this invention relates to DPP-IV inhibitor. More particularly, this invention relates to DPP-IV inhibitor useful for treating or preventing conditions mediated by DPP-IV, more particularly useful for treating or preventing altered glucose tolerance, glucosuria, hyperlipidemia, metabolic acidosis, diabetes mellitus (IDDM and NIDDM), diabetic neuropathy, nephropathy, and secondary diseases in mammals caused by diabetes mellitus.

That is, one object of this invention is to provide new compound and pharmaceutically acceptable salt thereof, of which activity to inhibit DPP-IV is remarkably improved against known compounds.

Another object of this invention is to provide a medicament and pharmaceutical composition containing the compound and/or pharmaceutically acceptable salt thereof as an active ingredient.

A further object of this invention is to provide a inhibitor of DPP-IV and a method for inhibiting DPP-IV comprising administering an effective amount of the compound and/or pharmaceutically acceptable salt thereof.

A further object of this invention is to provide a use of the compound and pharmaceutically acceptable salt thereof as medicaments.

A further object of this invention is to provide the compound and pharmaceutically acceptable salt thereof which are useful for the manufacture of medicaments for treating or preventing conditions mediated by DPP-IV inhibition, more particularly useful for treating or preventing altered glucose tolerance, glucosuria, hyperlipidemia, metabolic acidosis, diabetes mellitus (IDDM and NIDDM), diabetic neuropathy, nephropathy, and secondary diseases in mammals caused by diabetes mellitus, especially NIDDM.

A further object of this invention is to provide the commercial package comprising the pharmaceutical composition containing the new compound.

The present invention is directed to the following compound of the formula (I) or pharmaceutically acceptable salt thereof.

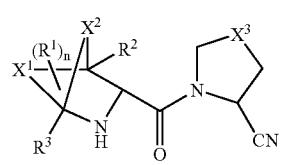

(I)

[wherein
  $X^1$ and $X^2$ each is independently lower alkylene;
  $X^3$ is $=CH_2$, $=CHF$ or $=CF_2$;
  $R^1$ is substituent;
  $R^2$ and $R^3$ are independently H or lower alkyl;
  n is 0, 1, 2, 3 or 4.]

The present invention is also directed to the following compound having formula (1) or pharmaceutically acceptable salt thereof:

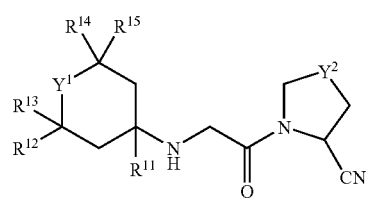

(1)

[wherein
  $Y^1$ is $—O—$, $—S—$ or $=NR^{16}$;
  $Y^2$ is $=CHF$ or $=CF_2$;
  $R^{11}$ is lower alkyl or lower alkyl substituted by hydroxy;
  $R^{12}$, $R^{13}$, $R^{14}$ and $R^{15}$ are independently H, lower alkyl or $R^{13}$ and $R^{14}$ may be connected together to make lower alkylene;
  $R^{16}$ is lower alkyl, heteroaryl (optionally substituted by substituent (i)) or [straight chain lower alkyl]sulfonyl;
  substituent (i) is selected from the group consisting of lower alkyl, lower alkoxy, amino, carboxy, hydroxy, cyano and halogen.]

Furthermore, the present invention is directed to the following compound having formula (2) or pharmaceutically acceptable salt thereof:

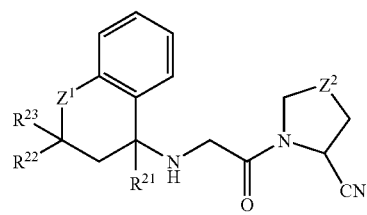

(2)

[wherein
  $Z^1$ is $—O—$, $—S—$ or $=NR^{24}$;
  $Z^2$ is $=CH_2$, $=CHF$ or $=CF_2$;
  $R^{21}$ is H, lower alkyl or lower alkyl substituted by hydroxy;

$R^{22}$ and $R^{23}$ are independently H, lower alkyl;

$R^{24}$ is lower alkyl, heteroaryl (optionally substituted by substituent (ii)) or [straight chain lower alkyl]sulfonyl;

benzene ring may be optionally substituted by substituent (ii);

substituent (ii) is selected from the group consisting of lower alkyl, lower alkoxy, amino, carboxy, hydroxy, cyano and halogen.]

In the above and subsequent description of the present specification, suitable examples of the various definitions to be included within the scope of the invention are explained in detail in the following.

The term "lower" is intended to mean a group having 1 to 6 carbon atom(s), unless otherwise provided.

Therefore, the "lower alkylene" means a straight or branched chain aliphatic hydrocarbon divalent group, such as methylene, methylmethylene, ethylmethylene, isopropylmethylene, isobutylmethylene, tert-butylmethylene, dimethylmethylene, isopropylmethylmethylene, ethylene, methylethylene, ethylethylene, isopropylethylene, isobutylethylene, tert-butylethylene, 1,1-dimethylmethylene, 1,2-dimethylmethylene, propylene, methylpropylene, ethylpropylene, isopropylpropylene, and the like. It is preferably (C1–C4)alkylene, more preferably (C1–C3)alkylene, more preferably (C1–C2)alkylene, most preferably methylene or ethylene. Preferably, in the definition of $X^1$ and $X^2$, the lower alkylene is methylene or ethylene which may be substituted by (C1–C4)alkyl.

The "lower alkyl" means a straight or branched chain aliphatic hydrocarbon, such as methyl, ethyl, propyl, isopropyl, butyl, isobutyl, tert-butyl, pentyl, hexyl, and the like. It is preferably (C1–C4)alkyl, more preferably (C1–C2)alkyl, most preferably methyl.

The "(lower)alkenyl" means a straight or branched chain aliphatic hydrocarbon group having more than one double bond between two carbon atoms, such as vinyl, 1-methylvinyl, 1-propenyl, 2-propenyl, 1-methyl-1-propenyl, 2-butenyl, 3-butenyl, 3-methyl-2-butenyl, pentenyl, hexenyl, and the like. It is preferably (C2–C5)alkenyl, more preferably (C2–C5)alkenyl, most preferably 2-propenyl (allyl).

The "aryl" means an aromatic hydrocarbon group, such as phenyl, naphthyl, indenyl, and the like, and it is preferably (C6–C10)aryl, more preferably phenyl.

Therefore, the "aryloxy" means oxy group substituted with the above aryl, and includes phenyloxy, naphthyloxy, indenyloxy, and the like, and it is preferably phenyloxy.

The "heteroaryl" means 5- or 6-membered aromatic heterocyclic group which contains at least one hetero atom such as nitrogen, oxygen and sulfur atom. The "heteroaryl" may include 5-membered heteroaryl group such as pyrrolyl, imidazolyl, pyrazolyl, thienyl, furyl, oxazolyl, isoxazolyl, thiazolyl, isothiazolyl, thiadiazol, or the like; 6-membered heteroaryl group such as pyridinyl, pyrazinyl, pyrimidinyl, pyridazinyl, or the like. It is preferably nitrogen containing heteroaryl, more preferably thiadiazol or pyridinyl, most preferably pyridinyl. The "heteroaryloxy" means oxy group substituted said heteroaryl group.

The "lower alkanoyl" means a formyl and a lower alkyl carbonyl group such as acetyl, propionyl, butyryl, isobutyryl, valeryl, isovaleryl, pivaloyl, hexanoyl, and the like. It is preferably (C1–C4)alkanoyl (including formyl), more preferably (C1–C2)alkanoyl, most preferably acetyl.

The "(lower alkyl)sulfonyl", "arylsulfonyl", "heteroarylsulfonyl" means sulfonyl group substituted with the above lower alkyl, aryl, heteroaryl, respectively.

The "(lower)alkoxy" means a straight or branched chain aliphatic hydrocarbon oxy group, such as methoxy, ethoxy, propoxy, isopropoxy, butoxy, isobutoxy, tert-butoxy, pentoxy, hexoxy, and the like. It is preferably (C1–C4)alkoxy, more preferably (C1–C2)alkoxy.

The "aryl (lower alkyl) oxy" means the "lower alkoxy" group mentioned above substituted by aryl group, and includes benzyloxy, 1-phenylethoxy, 2-phenylethoxy, 3-phenylpropoxy, 4-phenylbutoxy, naphthylmethoxy, 2-naphthylethoxy, and the like. It is preferably phenyl(lower alkyl)oxy, more preferably phenyl[(C1–C4)alkyl]oxy, more preferably phenyl[(C1–C2)alkyl]oxy 1, most preferably benzyloxy.

The "heteroaryl(lower alkyl)oxy" means the "lower alkoxy" group mentioned above substituted by heteroaryl group. It is preferably heteroaryl[(C1–C4)alkyl]oxy, more preferably heteroaryl[(C1–C2)alkyl]oxy, more preferably (nitrogen containing heteroaryl)[(C1–C2)alkyl]oxy, most preferably pyridinylmethyloxy.

The "saturated heterocyclyl" means 5- or 6-membered saturated heterocyclyl group which contains at least one hetero atom such as nitrogen, oxygen, or sulfur atom. The "saturated heterocyclyl" may be substituted with general substituent such as lower alkyl. The "saturated heterocyclyl" may include 5-membered saturated heterocyclyl group such as pyrrolidinyl, methylpyrrolidinyl, imidazolidinyl, pyrazolidyl, tetrahydrofuranyl, tetrahydrothiophenyl, oxazolidyl, isoxazolidyl, thiazolidyl, isothiazolidyl, or the like; and 6-membered saturated heterocyclyl group such as piperidyl, piperazinyl, tetrahydropyranyl, pentamethylene sulfide, morpholinyl, or the like. It is preferably nitrogen containing saturated heterocyclyl.

The "halogen" may include a fluorine atom, a chlorine atom, a bromine atom and an iodine atom, more preferably a fluorine atom or a chlorine atom, most preferably a fluorine atom.

The "(lower alkyl)amino" means a amino group substituted by the above lower alkyl group, such as methylamino, ethylamino, propylamino, isopropylamino, butylamino, isobutylamino, tert-butylamino, pentylamino, hexylamino, and the like. It is preferably [(C1–C4)alkyl]amino, more preferably [(C1–C2)alkyl]amino.

The "di(lower alkyl)amino" means a amino group substituted by the same or different above two lower alkyl groups, such as dimethylamino, diethylamino, dipropylamino, diisopropylamino, dibutylamino, diisobutylamino, dipentylamino, dihexylamino, ethylmethylamino, methylpropylamino, butylmethylamino, ethylpropylamino, butylethylamino, and the like, and it is preferably di[(C1–C4)alkyl]amino, more preferably di[(C1–C2)alkyl]amino, most preferably dimethylamino.

The "arylamino" means amino group substituted with the above aryl, and includes phenylamino, naphthylamino, indenylamino, and the like, and it is preferably phenylamino.

The "heteroarylamino" means amino group substituted said heteroaryl group.

The "halogenated (lower alkyl)" means the above lower alkyl substituted by halogen atom(s), such as fluoromethyl, chloromethyl, difluoromethyl, dichloromethyl, dibromomethyl, trifluoromethyl, trichloromethyl, fluoroethyl, chloroethyl, 2,2,2-trifluoroethyl, 2,2,2-trichloroethyl, 2,2,3,3,3-pentafluoroethyl, fluoropropyl, fluorobutyl, fluorohexyl, and the like. It is preferably halogenated[(C1–C4)alkyl], more preferably halogenated[(C1–C2)alkyl], more preferably fluorinated[(C1–C4)alkyl], more preferably fluorinated [(C1–C2)alkyl], most preferably trifluoromethyl.

The "(lower alkyl)sulfonylamino", "[halogenated(lower alkyl)]sulfonylamino", "arylsulfonylamino", "heteroarylsulfonylamino", "di(loweralkyl)aminosulfonylamino" means sulfonylamino group substituted with the above lower alkyl, [halogenated(lower alkyl), aryl, heteroaryl, di(lower alkyl) amino, respectively.

The "(lower alkanoyl)amino" means amino group substituted with the above lower alkanoyl.

The "lower alkyl substituted by hydroxy" means the above mentioned lower alkyl group substituted by a hydroxy, such as hydroxymethyl, hydroxyethyl, hydroxypropyl, hydroxyisopropyl, hydroxybutyl, hydroxyisobutyl, (hydroxy)tert-butyl, and the like, and it is preferably (C1–C4)alkyl substituted by hydroxy, more preferably (C1–C2)alkyl substituted by hydroxy, most preferably hydroxymethyl.

The "[straight chain lower alkyl]sulfonyl" in the definition of $R^{16}$ or $R^{24}$ is exemplified methylsulfonyl, ethylsulfonyl, n-propylsulfonyl, and the like, and it is preferably methylsulfonyl or ethylsulfonyl, most preferably methylsulfonyl.

The "substituent" in the definition of Compound (I) is not limited, but means general substituent. The "substituent" can be exemplified by:
(a) $R^4O$— wherein $R^4$ is H, lower alkyl optionally substituted with substituent α, lower alkenyl, aryl optionally substituted with substituent α, or heteroaryl optionally substituted with substituent α;
(b) $R^5R^6N$— wherein $R^5$ and $R^6$ each is independently H, lower alkyl, lower alkanoyl, (lower alkyl)sulfonyl, arylsulfonyl optionally substituted with substituent α, or heteroarylsulfonyl optionally substituted with substituent α;
(c) $R^7N$= wherein $R^7$ is H, hydroxy, lower alkoxy, aryl (lower alkyl)oxy optionally substituted with substituent α on the aryl group, or heteroaryl(lower alkyl)oxy optionally substituted with substituent α on the heteroaryl group,
(d) saturated heterocyclyl;
(e) carboxy;
(f) sulfonic acid;
(g) halogen; and
(h) oxo.

The above substituent α is not also limited, but means general substituent. The "substituent α" can be selected from the group consisting of lower alkyl, hydroxy, lower alkoxy, aryloxy optionally substituted with substituent β, heteroaryloxy optionally substituted with substituent β, amino, (lower alkyl)amino, di(lower alkyl)amino, arylamino optionally substituted with substituent β on the aryl group, heteroarylamino optionally substituted with substituent β on the heteroaryl group, (lower alkyl)sulfonylamino, [halogenated(lower alkyl)]sulfonylamino, arylsulfonylamino optionally substituted with substituent β on the aryl group, heteroarylsulfonylamino optionally substituted with substituent β on the heteroaryl group, di(lower alkyl)aminosulfonylamino, oxo, imino, hydroxyimino, (lower alkyl)sulfonyl, arylsulfonyl optionally substituted with substituent β, heteroarylsulfonyl optionally substituted with substituent β, lower alkanoyl, halogen, cyano, nitro and carboxy.

The above substituent β is not also limited, but means general substituent. The "substituent β" can be selected from the group consisting of lower alkyl, hydroxy, lower alkoxy, amino, (lower alkyl)amino, di(lower alkyl)amino, (lower alkanoyl)amino, halogen, cyano, nitro and carboxy.

The number of substituent α and β may be two or more if feasible. In case that the number of substituent α or β is plural, they may be identical or different to each other. For example, lower alkyl optionally substituted with substituent α in the definition of $R^4$ includes lower alkyl substituted with carbamoyl which may be further substituted with such as sulfonyl group, two or more hydroxys, and alkoxycarbonyl.

From another point of view, hydrophilic group is preferable as the "substituent" in the definition of Compound (I). The "hydrophilic group" means polar group having strong affinity for water and general group substituted by such polar group. The "hydrophilic group" can be exemplified by hydroxy, amino, carboxy, sulfonic acid, imino, and lower alkoxy substituted by such as hydroxy, or the like.

"$R^1$" in Compound (I) may be located on the azabicyclo moiety directly or on the alkyl group in the $X^1$, $X^2$, $R^2$ or $R^3$, preferably it is located directly on the azabicyclo moiety. In case that the number of $R^1$ is plural (n is 2, 3 or 4), $R^1$s maybe identical or different to each other.

The "heteroaryl" in the definition of $R^{16}$ and $R^{24}$ in Compound (1) and (2) may be substituted by substituent (i) and (ii), respectively. The number of the substituent depends on the kind of the heteroaryl, and is preferably 1 to 3, more preferably 1 or 2, most preferably 1. In case that the number of substituent (i) or (ii) is plural, they may be same or different each other.

The Compound (I), (1) and (2) may contain one or more asymmetric centers and thus they can exist as enantiomers or diastereoisomers. This invention includes both mixtures and separate individual isomers. However, in the 2-position of 2-cyanopyrrolidine moiety (the position substituted with cyano group), (2S) isomer is more preferable.

The compounds of the formula (I), (1) and (2) may also exist in tautomeric forms and this invention includes both mixtures and separate individual tautomers.

The Compound (I), (1), (2) and their salts may be in a form of a solvate such as hydrate, which is included within the scope of the present invention.

Also included in the scope of this invention are radiolabelled derivatives of Compound (I), (1) and (2) which are suitable for biological studies.

In the scope of the present invention, the prodrug of the Compound (I), (1) and (2) is included, which prodrug is capable of undergoing metabolic conversion to Compound (I), (1) and (2) following administration in body. Further, in the scope of the present invention, metabolites of Compound (I), (1) and (2) are included, which metabolites are therapeutically active in the treatment of the targeted medical condition.

The compounds of this invention can be converted to salt according to a conventional method. Suitable salts of the compounds (I), (1) and (2) are pharmaceutically acceptable conventional non-toxic salts and include an organic acid salt (e.g., acetate, maleate, tartrate, methanesulfonate, benzenesulfonate, formate, toluenesulfonate, trifluoroacetate, or the like), an inorganic acid salt (e.g., hydrochloride, hydrobromide, sulfate, phosphate, or the like), a salt with an amino acid (e.g., aspartate, glutamate, or the like), or the like.

In the each definition of the Compound (I), preferably,
(1) $X^1$ and $X^2$ each is independently (C1–C4)alkylene;
(2) $X^1$ and $X^2$ each is independently (C1–C3)alkylene;
(3) $X^1$ and $X^2$ each is independently (C1–C2)alkylene;
(4) $X^1$ is methylene;
(5) $X^1$ is ethylene;
(6) $X^2$ is methylene;
(7) $X^2$ is ethylene;
(8) $X^3$ is =$CH_2$ or =CHF;
(9) $X^3$ is =$CH_2$;
(10) $R^1$ is hydrophilic group;
(11) $R^1$ is selected from the group consisting of hydroxy, lower alkoxy optionally substituted with hydroxy(s), lower alkenyloxy, amino optionally substituted with lower alkanoyl, halogen, oxo, imino and hydroxyimino;
(12) $R^1$ is selected from the group consisting of hydroxy, amino and halogen;
(13) $R^1$ is selected from the group consisting of hydroxy, amino, (lower alkyl)amino and di(lower alkyl)amino;
(14) $R^1$ is hydroxy;
(15) $R^1$ is amino, (lower alkyl)amino or di(lower alkyl)amino;
(16) $R^1$ is amino, [(C1–C2)alkyl]amino or di[(C1–C2)alkyl]amino;
(17) $R^1$ is $R^4O$— wherein $R^4$ is lower alkyl optionally substituted with substituent α, aryl optionally substituted with substituent α, or heteroaryl optionally substituted with substituent α; the said substituent α is selected from the group consisting of hydroxy, arylamino, heteroarylamino, arylsulfonylamino, heteroarylsulfonylamino, oxo, imino, hydroxyimino, lower alkanoyl, halogen, cyano, nitro and carboxy;
(18) $R^1$ is lower alkoxy optionally substituted with substituent α, the said substituent α is selected from the group consisting of hydroxy, lower alkoxy, amino, (lower alkyl)amino, di(lower alkyl)amino, (lower alkyl)sulfonylamino, [halogenated(lower alkyl)]sulfonylamino, di(lower alkyl)aminosulfonylamino, oxo, imino, hydroxyimino and carboxy;
(19) $R^1$ is selected from the group consisting of lower alkoxy optionally substituted with substituent α, the said substituent α is selected from the group consisting of aryl (lower alkyl)oxy optionally substituted with substituted with substituent β, heteroarylamino optionally substituted with substituted with substituent β, heteroarylsulfonylamino optionally substituted with substituted with substituent β, oxo and arylsulfonyl optionally substituted with substituted with substituent β, the said substituent β is selected from the group consisting of lower alkyl, hydroxy, lower alkoxy, amino, (lower alkanoyl)amino, halogen, cyano, nitro and carboxy;
(20) $R^1$ is lower alkoxy optionally substituted with substituent α; the substituent α is selected from the group consisting of heteroarylamino optionally substituted with substituent β on the heteroaryl group, heteroarylsulfonylamino optionally substituted with substituent β on the heteroaryl group and oxo; the said substituent β is selected from the group consisting of lower alkyl, hydroxy, lower alkoxy, amino, (lower alkyl)amino, di(lower alkyl)amino, lower alkanoyl, halogen, cyano, nitro and carboxy.
(21) $R^1$ is selected from the group consisting of aryloxy optionally substituted with substituent α, heteroaryloxy optionally substituted with substituent α, and saturated heterocyclyl; the said substituent α is selected from the group consisting of lower alkyl, hydroxy, lower alkoxy, amino, (lower alkyl)amino, di(lower alkyl)amino, lower alkanoyl, halogen, cyano, nitro and carboxy;
(22) $R^1$ is selected from the group consisting of aryloxy optionally substituted with substituent α, and heteroaryloxy optionally substituted with substituent α; the said substituent α is selected from the group consisting of lower alkyl, hydroxy, lower alkoxy, amino, (lower alkyl)amino, di(lower alkyl)amino, lower alkanoyl, halogen, cyano, nitro and carboxy;
(23) $R^1$ is $R^5R^6N$— wherein $R^5$ and $R^6$ each is independently (lower alkyl)sulfonyl, arylsulfonyl optionally substituted with substituent α, or heteroarylsulfonyl optionally substituted with substituent α; the said substituent α is selected from the group consisting of lower alkyl, hydroxy, lower alkoxy, amino, (lower alkyl)amino, di(lower alkyl)amino, lower alkanoyl, halogen, cyano, nitro and carboxy;
(24) $R^1$ is $R^7N$= wherein $R^7$ is H, hydroxy, lower alkoxy, or aryl(lower alkyl)oxy optionally substituted with substituent α on the aryl group; the said substituent α is selected from the group consisting of lower alkyl, hydroxy, lower alkoxy, amino, (lower alkyl)amino, di(lower alkyl)amino, lower alkanoyl, halogen, cyano, nitro and carboxy;
(25) $R^1$ is selected from the group consisting of lower alkoxy, amino and imino, the said lower alkoxy, amino and imino optionally substituted with substituent α, the said substituent α is selected from the group consisting of hydroxy, aryloxy optionally substituted with substituent β, heteroaryloxy optionally substituted with substituent β, aryl (lower alkyl)oxy optionally substituted with substituent β on the aryl group, arylamino optionally substituted with substituent β on the aryl group, heteroarylamino optionally substituted with substituent β on the heteroaryl group, arylsulfonylamino optionally substituted with substituent β on the aryl group, heteroarylsulfonylamino optionally substituted with substituent β on the heteroaryl group, oxo, imino, hydroxyimino, arylsulfonyl optionally substituted with substituent β on the aryl group, heteroarylsulfonyl optionally substituted with substituent β on the heteroaryl group, lower alkanoyl, halogen, cyano, nitro and carboxy; the said substituent β is selected from the group consisting of lower alkyl, hydroxy, lower alkoxy, amino, (lower alkyl)amino, di(lower alkyl)amino, (lower alkanoyl)amino, halogen, cyano, nitro and carboxy;
(26) $R^1$ is selected from the group consisting of lower alkoxy, amino and imino, the said lower alkoxy, amino and imino optionally substituted with substituent α; the said substituent α is selected from the group consisting of aryl(lower alkyl)oxy, heteroarylamino, heteroarylsulfonylamino, oxo, arylsulfonyl, the said aryl(lower alkyl)oxy, heteroarylamino, heteroarylsulfonylamino and arylsulfonyl may have substituent β on the aryl or heteroaryl group, the substituent β is selected from the group consisting of lower alkyl, hydroxy, lower alkoxy, amino, (lower alkanoyl)amino, halogen, cyano, nitro and carboxy;
(27) $R^2$ and $R^3$ each is independently H or (C1–C4)alkyl;
(28) $R^2$ and $R^3$ each is independently H or (C1–C2)alkyl;
(29) $R^2$ and $R^3$ are H;
(30) $R^2$ is H or (C1–C4)alkyl;
(31) $R^2$ is H;
(32) $R^2$ is (C1–C2)alkyl;
(33) $R^2$ is methyl;
(34) $R^3$ is H or (C1–C4)alkyl;
(35) $R^3$ is H;
(36) $R^3$ is methyl;
(37) $R^3$ is isopropyl;
(38) n is 1, 2, 3 or 4;
(39) n is 1 or 2;
(40) n is 1;
(41) n is 2.

The Compound (I) is preferably selected from:
(2S)-1-{[(1S,3S,4S,5S,6R)-5,6-Dihydroxy-2-azabicyclo[2.2.2]oct-3-yl]carbonyl}-2-pyrrolidinecarbonitrile hydrochloride;
(2S)-1-{[(1S,3S,4S,5R)-5-Hydroxy-2-azabicyclo[2.2.2]oct-3-yl]carbonyl}-2-pyrrolidinecarbonitrile hydrochloride;
(2S)-1-{[(1R,3S,4S,6R)-6-Hydroxy-2-azabicyclo[2.2.1]hept-3-yl]carbonyl}-2-pyrrolidinecarbonitrile hydrochloride;

(2S)-1-{[(1R,3S,4S,6S)-6-Hydroxy-2-azabicyclo[2.2.1]hept-3-yl]carbonyl}-2-pyrrolidinecarbonitrile hydrochloride;

(2S)-1-{[(1R,3S,4S,6R)-6-(2-Hydroxyethoxy)-2-azabicyclo[2.2.1]hept-3-yl]carbonyl}-2-pyrrolidinecarbonitrile hydrochloride;

(2S)-1-{[(1R,3S,4S,6Z)-6-Hydroxyimino-2-azabicyclo[2.2.1]hept-3-yl]carbonyl}-2-pyrrolidinecarbonitrile hydrochloride;

N-((1R,3S,4S,6R)-3-{[(2S)-2-Cyano-1-pyrrolidinyl]carbonyl}-2-azabicyclo[2.2.1]hept-6-yl)acetamide hydrochloride;

(2S)-1-{[(1R,3S,4R,6R)-6-Amino-2-azabicyclo[2.2.1]hept-3-yl]carbonyl}-2-pyrrolidinecarbonitrile dihydrochloride;

(2S)-1-{[(1R,4R,5R,7S)-4-Hydroxy-6-azabicyclo[3.2.1]oct-7-yl]carbonyl}-2-pyrrolidinecarbonitrile hydrochloride.

In the each definition of the compound formula (1) preferably,
(42) $Y^1$ is —O—;
(43) $Y^1$ is —S—;
(44) $Y^1$ is =$NR^{16}$;
(45) $Y^2$ is =CHF;
(46) $R^{11}$ is (C1–C4)alkyl;
(47) $R^{11}$ is (C1–C4)alkyl substituted by hydroxy;
(48) $R^{11}$ is hydroxymethyl;
(49) $R^{12}$, $R^{13}$, $R^{14}$ and $R^{15}$ are independently H or methyl;
(50) $R^{12}$ and $R^{15}$ are independently H or methyl, and $R^{13}$ and $R^{14}$ may be connected together to make (C1–C4)alkylene;
(51) $R^{12}$ and $R^{15}$ are independently H or methyl, and $R^{13}$ and $R^{14}$ may be connected together to make ethylene;
(52) $R^{16}$ is (C1–C4)alkyl;
(53) $R^{16}$ is heteroaryl (optionally substituted by substituent (i));
(54) $R^{16}$ is heteroaryl;
(55) $R^{16}$ is nitrogen containing heteroaryl (optionally substituted by substituent (i));
(56) $R^{16}$ is nitrogen containing heteroaryl;
(57) $R^{16}$ is [(C1–C2)alkyl]sulfonyl;
(58) substituent (i) is selected from the group consisting of lower alkoxy, amino and hydroxy;
(59) substituent (i) is selected from the group consisting of carboxy, cyano and halogen;
(60) substituent (i) is cyano or halogen;
(61) substituent (i) is (are) cyano.

In the each definition of the compound formula (2) preferably,
(62) $Z^1$ is —O—;
(63) $Z^1$ is —S—;
(64) $Z^1$ is =$NR^{24}$;
(65) $Z^2$ is =$CH_2$ or =CHF;
(66) $Z^2$ is =CHF;
(67) $R^{21}$ is H;
(68) $R^{21}$ is (C1–C4)alkyl;
(69) $R^{21}$ is (C1–C4)alkyl substituted by hydroxy;
(70) $R^{21}$ is hydroxymethyl;
(71) $R^{22}$ and $R^{23}$ are independently H or methyl;
(72) $R^{22}$ and $R^{23}$ are H;
(73) $R^{24}$ is (C1–C4)alkyl;
(74) $R^{24}$ is heteroaryl (optionally substituted by substituent (ii));
(75) $R^{24}$ is heteroaryl;
(76) $R^{24}$ is nitrogen containing heteroaryl;
(77) $R^{24}$ is [(C1–C2)alkyl]sulfonyl;
(78) substituent (ii) is selected from the group consisting of lower alkoxy, amino and hydroxy;
(79) substituent (ii) is selected from the group consisting of carboxy, cyano and halogen;
(80) substituent (ii) is cyano or halogen;
(81) substituent (ii) is cyano.

The Compound (I) of the present invention can be prepared according to the following Process A.

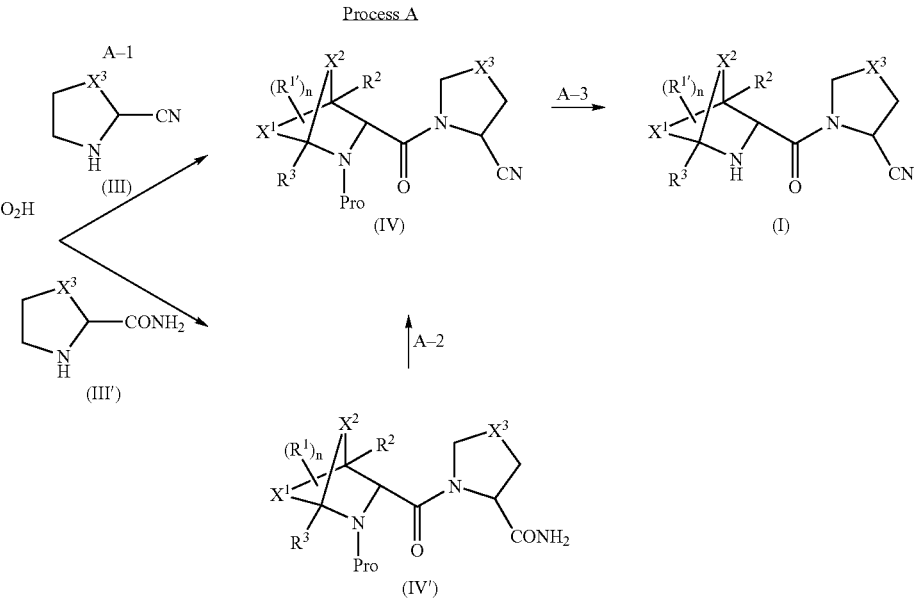

In the above formula, $R^1$ to $R^3$, $X^1$ to $X^3$ and n represent the same meanings as defined above. "$R^{1'}$" represents $R^1$ protected not to inhibit this reaction, if needed. "Pro" represents protective group of amino group.

Process A is the process for preparing the Compound (I).

Process A-1

This process is carried out by reacting carboxylic acid Compound (II) with pyrrolidine Compound (III) or (III') in the presence of catalyst in solvent.

Compound (II) may be purchased if it is commercial, or synthesized according to Process B to Process E mentioned after or other general methods obvious to the person skilled in the organic chemistry from commercial compounds. Compound (III) and (III') may be purchased if it is commercial or synthesized by general methods obvious to the person skilled in the organic chemistry from commercial compounds, since the structure of Compound (III) and (III') is relatively simple.

In this process, general amide-forming reaction such as the reaction using condensing agent can be employable. The condensing agent employable in this process is not particularly limited so long as it accelerates forming amide bond and may include carbodiimide compounds such as dicyclohexylcarbodiimide (DCC), diisopropyl-carbodiimide (DIPCI), water solvable carbodiimide (WSCD) such as 1-ethyl-3-(3'-dimethylaminopropyl)-carbodiimide.

In this case, additive is generally used. The additive employable in this process is not particularly limited so long as it can mainly make the carboxyl groups of Compound (II) active or suppress the racemization, and may include 1-hydroxybenzotriazole (HOBt), 3,4-dihydro-3-hydroxy-4-oxo-1,2,3-benzotriazole (HOOBt), 1-hydroxy-7-azabenzotriazole (HOAt).

The solvent employable in this process is not particularly limited so long as it is inactive in this reaction and may include amides such as dimethylformamide and dimethylacetamide; alcohol such as methanol and ethanol.

This process is generally carried out by adding Compound (III) or (III') and base, to the solution of Compound (II), condensing agent and additive.

The base employable in this step may include organic amines such as triethylamine and diisopropylethylamine (DIEA).

The temperature at that time depends on the starting material, the solvent, or the like, and it is usually room temperature.

The reaction time after the adding depends on the starting material, the solvent, or the like, and it is usually from 1 hr to 24 hrs.

After the reaction, the mixture is quenched with water, and extracted with organic solvent insoluble with water such as ethyl acetate, chloroform, or the like. The organic layer is washed by water such as hydrochloric acid, saturated aqueous NaHCO$_3$, brine, or the like. The washed organic layer is dried over anhydrous magnesium sulfate or sodium sulfate, and evaporated in vacuo. The target compound is purified by the conventional method such as silica gel chromatography to obtain Compound (IV) or (IV').

Process A-2

Then, carbamoyl group of Compound (IV') is transformed to cyano group to synthesize Compound (IV) if necessary.

In this Process A-2, some general dehydration reactions can be adopted. For example, acid anhydride such as trifluoroacetic anhydride and organic amine are reacted with Compound (IV') in solvent.

The organic amine employable in this process may include pyridine, triethylamine, tributylamine, diisopropylethylamine.

The solvent employable in this process is not particularly limited so long as it is inactive in this reaction, and may include ether such as diethyether, tetrahydrofuran and dioxane.

This Process A-2 is generally carried out by adding organic amine and acid anhydride to the solution of Compound (IV'). When organic amine and acid anhydride were added, the temperature is preferably −10° C. to 20° C. However, after the addition, the temperature can be raised to room temperature. The reaction time after the addition depends on the starting material, the solvent, or the like, and it is usually from 1 hr to 12 hrs.

After the reaction, the mixture is alkalized with base such as saturated aqueous NaHCO$_3$, and concentrated in vacuo. The residue is diluted with H$_2$O, the mixture is extracted with organic solvent insoluble with water such as ethyl acetate, chloroform, or the like. The organic layer is dried over anhydrous magnesium sulfate or sodium sulfate, and evaporated in vacuo. The target compound is purified by the conventional method such as recrystallization to obtain Compound (IV).

Process A-3

Finally, in case that "Pro" is protective group of amino group, Compound (IV) is deprotected to give Compound (I).

Concerning the protective group of Compound (IV), the general kind and the condition of cleavage reaction may be referred to [PROTECTIVE GROUPS IN ORGANIC SYNTHESIS Second Edition] T. W. Green and P. G. M. Wuts, John Wiley & Sons, INC. (the contents of which are hereby incorporated by reference).

For example, in case that "Pro" is carbamate such as tert-butoxycarbonyl or methoxycarbonyl, the cleavage reaction is carried out in acidic condition.

The solvent employable in this case is not particularly limited so long as it is inactive in this reaction and may include halogenated hydrocarbon such as dichloromethane, chloroform.

The reagent for making acidic condition is not particularly limited so long as it accelerates cleavage reaction and may include hydrogen chloride solution in solvent such as 4N hydrogen chloride solution in 1,4-dioxane.

This process is generally carried out by adding the reagent for making acidic condition dropwise to the solution of Compound (IV). The temperature at that time depends on the starting material, the solvent, or the like, and it is usually from −10° C. to 30° C., preferably room temperature.

The reaction time after adding the reagent for making acidic condition depends on the starting material, the solvent, or the like, and it is usually from 10 minutes to 2 hrs.

After the reaction, the organic solvent was removed, and the target Compound (I) maybe obtained by conventional purifying method such as thin layer chromatography, silica gel column chromatography, or the like. After the reaction of Process A-3, the residue may be only washed with solvent, which does not dissolve the target Compound (I) to remove excess acid.

Addition of two hydroxy groups to the azabicyclo moiety can be carried out as following Process B, provided that following schemes are typical examples and can be applied to the production of Compound (II).

Process B

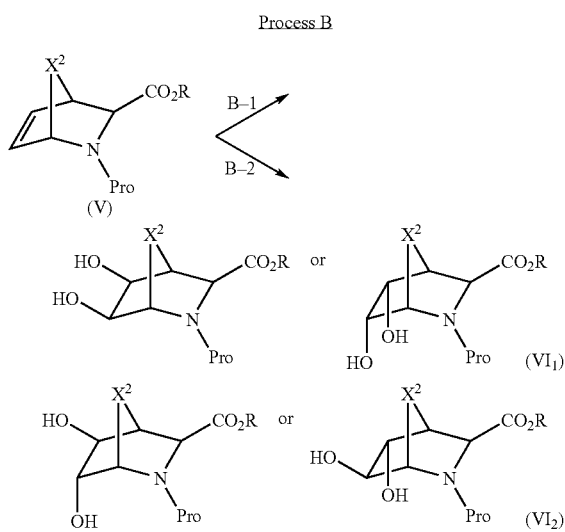

In the above formula, $X^2$ and "Pro" represent the same meanings as defined above. "R" represents lower alkyl such as methyl or ethyl.

Process B is the process for adding two hydroxy groups to the double bond of azabicyclo moiety. Wherever the double bond is in the azabicyclo moiety, this reaction can be applied.

Compound (V) may be purchased if it is commercial, or synthesized other general methods obvious to the person skilled in the organic chemistry from commercial compounds.

Process B-1

Process B-1 (syn addition) can be carried out by adding the solution of osmium tetroxide ($OsO_4$) to the solution of Compound (V). This osmium tetroxide gives syn addition from the less-hindered side of the double bond of Compound (V) to give dihydroxy compound.

As the solvent for the solution of osmium tetroxide, water can be employable. The solvent employable for the solution of Compound (V) in this process is not particularly limited so long as it is inactive in this reaction, and may include water; ketones such as acetone and methylethyketone; alcohol such as methanol and ethanol; and mixed solvent thereof.

To reduce the amount of expensive osmium tetroxide, morpholine N-oxide, N-methylmorpholine-N-oxide, or the like can be added to the solution of Compound (V).

The temperature at that time depends on the starting material, the solvent, or the like, and it is usually room temperature.

The reaction time after the adding depends on the starting material, the solvent, or the like, and it is usually from 12 hrs to 50 days.

After the reaction, decomposing agent such as sodium thiosulfate ($Na_2S_2O_3$) or sodium sulfite ($Na_2SO_3$) is added to give dihydroxide Compound ($VI_1$) by decomposing cyclic ester consisting Compound (V) and osmium tetroxide.

After the addition of the decomposing agent, insoluble residue is filtered off. The obtained filtrate is evaporated, then acidic water such as sulfuric acid is added. The mixture is extracted with organic solvent insoluble with water such as ethyl acetate, chloroform, or the like, and the organic layer is washed by water, brine, or the like. The organic layer is dried over anhydrous magnesium sulfate or sodium sulfate, and evaporated in vacuo. The target compound is purified by the conventional method such as silica gel chromatography to obtain Compound ($VI_1$).

Process B-2

In case of Process B-2 (anti addition), $H_2O_2$ and acid (such as formic acid) are used. That is, first, epoxide is synthesized from Compound (V) and $H_2O_2$, and then Sn2 reaction takes place to give dihydroxide Compound ($VI_2$). Therefore, the position selectivity and stereo selectivity of hydroxy group mainly depend on the circumstance of the C—C double bond of Compound (V).

When one hydroxy group is introduced, Compound (VII) can be produced by following Process C.

Process C

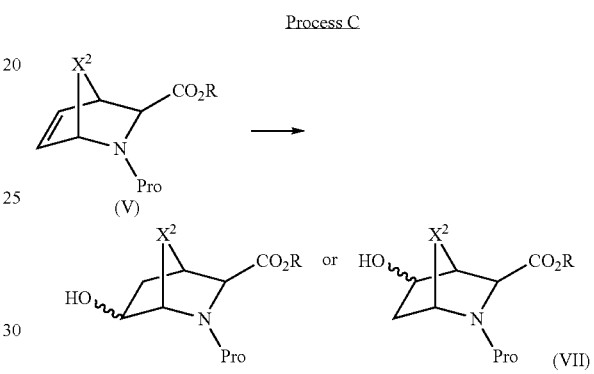

In the above formula, $X^2$, R and "Pro" represent the same meanings as defined above.

Process C is the process for adding one hydroxy group to the double bond of azabicyclo moiety. Wherever the double bond is in the azabicyclo moiety, this reaction can be applied.

Process C can be generally carried out by adding the solution of borane-tetrahydrofuran complex ($BH_3$-THF) to the solution of Compound (V) under $N_2$ atmosphere, and then basic aqueous solution of $H_2O_2$. In this Process C, the position selectivity and stereo selectivity of hydroxy group mainly depend on the circumstance of the C—C double bond of Compound (V).

As the solvent for the solution of Compound (V), tetrahydrofuran can be preferably employable. The base for making basic solution of $H_2O_2$ may include alkali metal hydroxides such as lithium hydroxide, sodium hydroxide and potassium hydroxide.

When borane-tetrahydrofuran complex or $H_2O_2$ was added, the each temperature depends on the starting material, the solvent, or the like, and it is usually $-10°$ C. to $10°$ C.

The each reaction time after adding borane-tetrahydrofuran complex or $H_2O_2$ depends on the starting material the solvent, or the like, and it is usually from 5 minutes to 5 hrs.

After the reaction, aqueous solution such as brine is added to the mixture, and the mixture is extracted with organic solvent insoluble with water such as ethyl acetate, chloroform, or the like. The organic layer is separated, washed by water, brine, or the like. The washed organic layer is dried over anhydrous magnesium sulfate or sodium sulfate, and evaporated in vacuo. The target compound is purified by the conventional method such as silica gel chromatography to obtain Compound (VII).

When one $R^1$ is introduced, Compound (VIII) is used as material compound as following Process D.

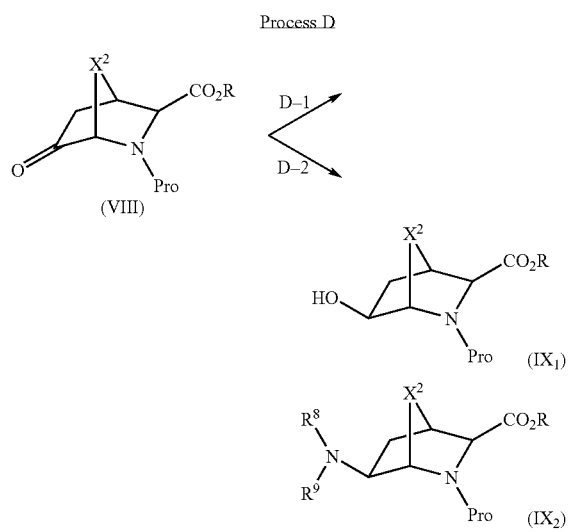

In the above formula, $X^2$, R and "Pro" represent the same meanings as defined above. $R^8$ and $R^9$ each is independently H or lower alkyl.

Process D is the process for conversion from oxo group in the azabicyclo moiety to $R^1$. Wherever the oxo group is in the azabicyclo moiety, this reaction can be applied.

Compound (VIII) may be purchased if it is commercial, or synthesized other general methods obvious to the person skilled in the organic chemistry from commercial compounds.

Process D-1

Process D-1 can be carried out by adding hydrogenation agent to the solution of Compound (VIII).

In this process, mild hydrogenation agent such as $NaBH_4$ is used, because strong hydrogenation agents can have negative effects on ester group of Compound (VIII).

Process D-2

Process D-2 can be carried out by adding ammonia or amines ($HNR^8R^9$) to the solution of Compound (VIII), and then adding hydrogenation agent. As this hydrogenation, the above method used in Process D-1 can be employable.

When Compound (I) having three or four $R^1$ is synthesized, other starting compound is used or the combination the above Process B to D can be applied.

In case $R^1$ is amino or (lower alkyl)amino, $R^1$ should be protected on cue.

After introducing $R^1$, the protective group of carboxyl group is removed to give Compound (II).

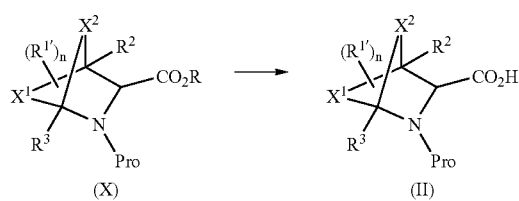

In the above formula, $R^1$ to $R^3$, R, $R^{1'}$, $X^1$, $X^2$, n and "Pro" represent the same meanings as defined above.

Compound (X) can be synthesized by applying the above Processes B to D or other general methods obvious to the person skilled in the organic chemistry from commercial compounds.

Process E is the process for deprotecting the ester group of Compound (X) to give Compound (II). In this process, general cleavage methods of ester group can be employable. For example, Compound (X) is dissolved in solvent, and base is added to the solution.

The solvent employable for the solution of Compound (X) in this process is not particularly limited so long as it is inactive in this reaction and may include water; alcohol such as methanol and ethanol; and mixed solvent thereof.

The base employable in this process can be alkali metal hydroxides such as sodium hydroxide and potassium hydroxide; alkali metal hydrogencarbonates such as lithium hydrogencarbonate, sodium hydrogencarbonate and potassium hydrogencarbonate; alkali metal carbonates such as lithium carbonate, sodium carbonate and potassium carbonate; alkaline earth metal carbonates such as magnesium carbonate and calcium carbonate.

The temperature at that time depends on the starting material, the solvent, or the like, and it is usually room temperature to reflux condition, preferably room temperature. The reaction time after the adding depends on the starting material, the solvent, or the like, and it is usually from 1 hr to 24 hrs.

The compound of the formula (1) of the present invention can be prepared according to the following Process F.

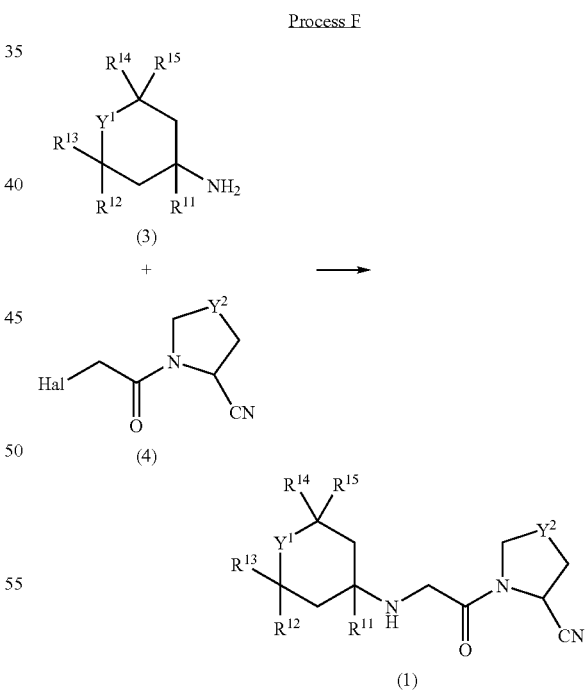

In the above formula, $R^{11}$ to $R^{15}$, $Y^1$ and $Y^2$ represent the same meanings as defined above. "Hal" represents halogen atom, especially, chlorine or bromine atom.

Process F is the process for preparing the Compound (1) by condensing Compound (3) and (4).

Compound (3) and (4) may be purchased if it is commercial, or synthesized according to general methods obvious to the person skilled in the organic chemistry from commercial compounds or following Process G and H, respectively.

This process is generally carried out by adding Compound (4) to the solution or mixture of Compound (3) and base. The temperature at that time depends on the starting material, the solvent, or the like, and it is usually −10° C. to 10° C., preferably the addition is carried out under cooling by ice bath. After the addition, the temperature may be raised to room temperature.

The solvent employable in Process F is not particularly limited so long as it is inactive in this reaction and dissolves moderately substrates, and may include preferably ethers such as diisopropyl ether, tetrahydrofuran and dioxane; alcohols such as methanol and ethanol.

The base employable in this process for making basic condition is not particularly limited so long as it accelerate this reaction, and may include alkali metal carbonates such as lithium carbonate, sodium carbonate and potassium carbonate; alkali metal hydrogencarbonates such as lithium hydrogencarbonate, sodium hydrogencarbonate and potassium hydrogencarbonate.

The reaction time after the adding depends on the starting material, the solvent, or the like, and it is usually from 12 hr to 2 days. To accelerate this reaction, a catalytic amount of NaI may be added.

After the reaction, the mixture is partitioned between water and organic solvent insoluble with water such as ethyl acetate, chloroform, or the like, and the organic layer is separated. The organic layer is washed by water, hydrochloric acid, saturated sodium hydrogencarbonate solution, brine, or the like, dried over anhydrous magnesium sulfate or sodium sulfate, and evaporated in vacuo. The target compound is purified by the conventional method such as silica gel column chromatography, or the like.

Compound (3), which is the starting compound of Process F, can be synthesized by following Process G.

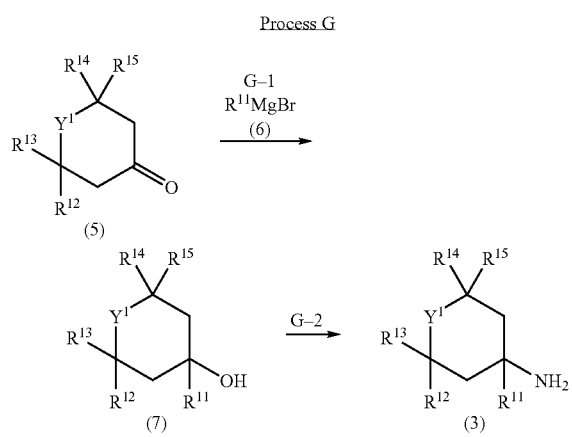

In the above formula, $R^{11}$ to $R^{15}$, $Y^1$ and $Y^2$ represent the same meanings as defined above.

Compound (5) and (6) may be purchased if it is commercial, or synthesized according to general methods obvious to the person skilled in the organic chemistry from commercial compounds.

Process G-1 can be carried out by applying conventional Grignard reaction method. For example, the solution of Compound (6) is added dropwise to the solution of Compound (5).

Then, the hydroxy group in Compound (7) is transformed to amino group by conventional functional group interchange transforms reaction. For example, the following reaction can be applicable.

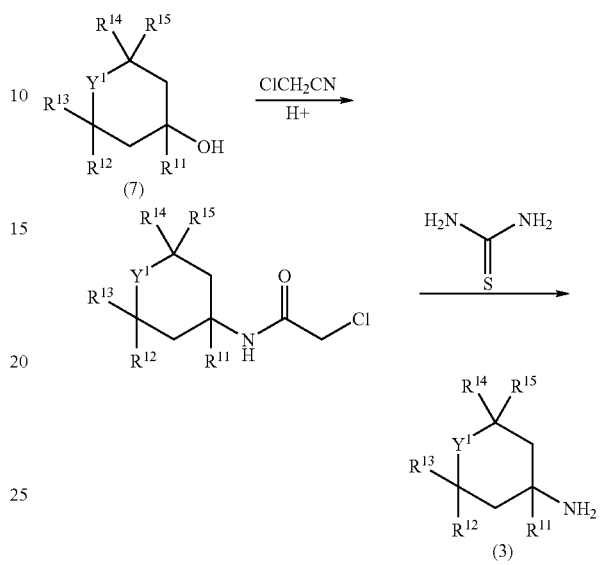

Besides Process G, Compound (3') in which $R^{11}$ is H can be obtained by Process H.

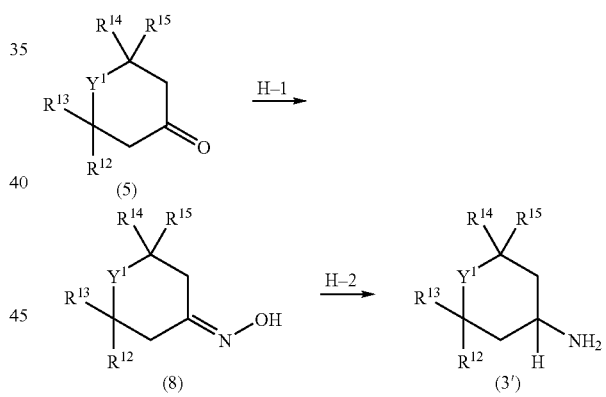

Compound (8) can be obtained by general oximation reaction. Then, this oxime compound (8) is reduced. The reduction condition is not limited, for example, oxime compound (8) is reduced under hydrogen atmosphere in the presence of catalyst at room temperature.

The solvent employable is not particularly limited, and may include preferably methanol and ethanol; and the mixture of water and alcohol. As the catalyst, palladium catalyst such as Pd(OH)$_2$ can be used.

The reaction time after the adding depends on the starting material, the solvent, or the like, and it is usually from 30 minutes to 6 hrs.

After the reaction, catalyst is removed by filtration, and the filtrate is concentrated to give Compound (3').

Compound (4), which is the starting compound of Process F, can be synthesized by following Process I.

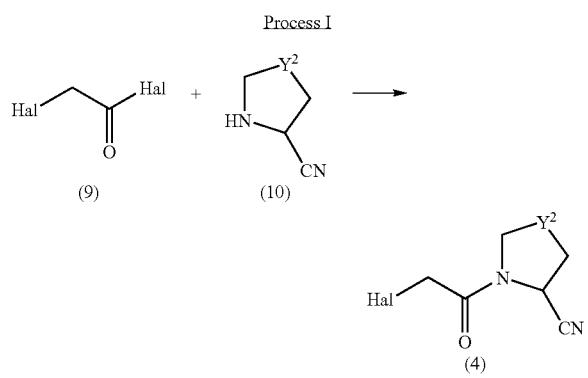

In the above formula, $Y^2$ and Hal represent the same meanings as defined above.

Process I is the process for preparing the Compound (4). This process is carried out by reacting Compound (9) and Compound (10) in the presence of base to form amide bond in solvent. A conventional reaction method to form amide bond is applicable to this Process I.

Compound (9) and (10) may be purchased if it is commercial, or synthesized by the methods obvious to the person skilled in the organic chemistry from commercial compounds, because Compound (9) and (10) as starting compound have comparatively simple structure.

In the Process I, conventional functional group interchange transforms reactions can be applicable. Such reactions can be exemplified as followings:

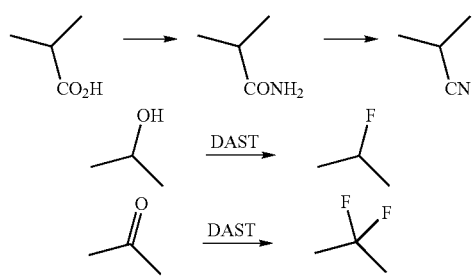

In the above formula, DAST is diethylaminosulfur trifluoride which is fluoridation agent. Concerning fluoridation, L. Demange, et al., Tetrahedron letters, 39, pp. 1169–1172 (1998) (the contents of which are hereby incorporated by reference) can be referred.

By application of the above Processes F to I, Compound (2) can be also synthesized.

Above processes, all starting materials and product compounds may be salts. The compounds of above processes can be converted to salt according to a conventional method.

In the above compounds, which have reactive group, may be protected at the group on cue and be deprotected on cue. In these reactions (protecting or deprotecting steps), concerning the kind of protective group and the condition of the reaction, [PROTECTIVE GROUPS IN ORGANIC SYNTHESIS Second Edition] T. W. Green and P. G. M. Wuts, John Wiley & Sons, INC. (the contents of which are hereby incorporated by reference) may be referred.

The patents, patent applications and publications cited herein are incorporated by reference.

For therapeutic purpose, Compound (I), (1) and (2) a pharmaceutically acceptable salt thereof of the present invention can be used in a form of pharmaceutical preparation containing one of said compounds as an active ingredient, in admixture with a pharmaceutically acceptable carrier such as an organic or inorganic solid or liquid excipient suitable for oral, parenteral or external administration. The pharmaceutical preparations maybe capsules, tablets, dragees, granules, inhalant, suppositories, solution, lotion, suspension, emulsion, ointment, gel, cream, or the like. If desired, there may be included in these preparations, auxiliary substances, stabilizing agents, wetting or emulsifying agents, buffers and other commonly used additives.

While the dosage of therapeutically effective amount of the Compound (I), (1) and (2) depend upon the age and condition of each individual patient, an average single dose of about 0.01 mg, 0.1 mg, 1 mg, 10 mg, 50 mg, 100 mg, 250 mg, 500 mg and 1000 mg of the Compound (I), (1) and (2) may be effective for treating the above-mentioned diseases. In general, amounts between 0.01 mg/body and about 1,000 mg/body may be administered per day.

This application is based on Australian Patent Application No. 2003906010 filed on Oct. 31, 2003 and No. 2004900961 filed on Feb. 25, 2004, the contents of which are hereby incorporated by references.

Although the present invention has been fully described by way of example, it is to be understood that various changes and modifications will be apparent to those skilled in the art. Therefore, unless otherwise such changes and modifications depart from the scope of the present invention hereinafter defined, they should be construed as being included therein.

THE BEST MODE FOR CARRYING OUT THE INVENTION

The following Examples are given only for the purpose of illustrating the present invention in more detail.

EXAMPLE 1-1

Ethyl (1S,3S,4S,5S,6R)-5,6-dihydroxy-2-[(1R)-1-phenylethyl]-2-azabicyclo[2.2.2]octane-3-carboxylate To a solution of ethyl (1S,3S,4R)-2-[(1R)-1-phenylethyl]-2-azabicyclo[2.2.2]oct-5-ene-3-carboxylate (9 g) and morpholine N-oxide in acetone/water=6/1 (90 mL), was added 4% solution of osmium tetroxide in water (2 mL) with cooling on an ice bath. The reaction mixture was warmed to room temperature and stirred for 4 days.

To the resulting mixture, $Na_2S_2O_3 \cdot 5H_2O$ and Florisil were added. The solid was then filtered off through a celite pad and washed with acetone. The combined filtrate and washings were concentrated in vacuo. The residue was acidified with 6N $H_2SO_4$ (pH2) and extracted with ethyl acetate. The combined organic layer was washed with saturated aqueous NaCl, dried over $MgSO_4$, and concentrated in vacuo. The residue was purified with silica gel chromatography (n-hexane/ethyl acetate=2/1 to 1/1) to give the target compound as a colorless oil (4.2 g).

$^1$H-NMR (CDCl$_3$): δ 7.52–7.11(5H, m), 4.12–3.89(4H, m), 3.85(1H, q, J=6.6 Hz), 3.48–3.38(1H, m), 3.06–2.98(1H, m), 2.98–2.86(1H, m), 2.64–2.51(1H, m), 2.12–2.01(1H, m), 1.98–1.58(3H, m), 1.46–1.30(4H, m), 1.12(3H, t, J=7.2 Hz).

MASS (ES+) m/z: 320.46 (M+1).

EXAMPLE 1-2

Ethyl (1S,3S,4S,5S,6R)-5,6-dihydroxy-2-azabicyclo[2.2.2]octane-3-carboxylate

Ethyl (1S,3S,4S,5S,6R)-5,6-dihydroxy-2-[(1R)-1-phenylethyl]-2-azabicyclo[2.2.2]octane-3-carboxylate obtained in Example 1-1 (4.2 g) was dissolved in methanol (10 mL), and 10% Pd(OH)$_2$—C (800 mg) was added to the solution. The mixture was hydrogenated under H$_2$ (4.0 atm) at room temperature for 2 hrs.

The catalyst was filtered through a celite pad and washed with ethyl acetate. The filtrate and washings were concentrated in vacuo to give the target compound as colorless oil (2.9 g).

$^1$H-NMR (CDCl$_3$): δ 4.36–4.14(2H, m), 4.14–3.97(2H, m), 3.67–3.57(1H, m), 2.98–2.88(1H, m), 2.86–2.21(3H, m), 2.20–2.10(1H, m), 2.00–1.70(2H, m), 1.65–1.49(1H, m), 1.37–1.20(4H, m).

MASS (ES+) m/z: 216.30 (M+1).

EXAMPLE 1-3

(1S,3S,4S,5S,6R)-2-(tert-Butoxycarbonyl)-5,6-dihydroxy-2-azabicyclo[2.2.2]octane-3-carboxylic acid Ethyl (1S,3S,4S,5S,6R)-5,6-dihydroxy-2-azabicyclo[2.2.2]octane-3-carboxylate obtained in Example 1-2 (4.2 g) was dissolved in methanol (8 mL), and 1N NaOH (17 mL) was added to the solution at room temperature. The solution was stirred at that temperature for 2 hrs and the organic solvent (methanol) was removed in vacuo.

To this remaining aqueous solution, 530 mg of NaOH and then a solution of di-tert-butyl dicarbonate in dioxane (8 mL) were added dropwise at room temperature. The mixture was stirred for 16 hrs and then acidified with 1N HCl (pH2). The resulting precipitate was collected with filter paper and the precipitate was washed with chloroform to give the target compound as a white powder (2.81 g).

$^1$H-NMR (DMSO-d$_6$): δ 4.07–3.92(1H, m), 3.92–2.72 (2H, m), 3.72–2.55(1H, m), 2.12–1.49(4H, m), 1.46–1.25 (9H, m), 1.24–1.01(1H, m).

MASS (ES−) m/z: 286.29 (M−1).

EXAMPLE 1-4

Tert-Butyl (1S,3S,4S,5S,6R)-3-{[(2S)-2-cyano-1-pyrrolidinyl]carbonyl}-5,6-dihydroxy-2-azabicyclo[2.2.2]octane-2-carboxylate To a solution of (1S,3S,4S,5S,6R)-2-(tert-butoxycarbonyl)-5,6-dihydroxy-2-azabicyclo[2.2.2]octane-3-carboxylic acid obtained in Example 1-3 (500 mg) 1-hydroxybenzotriazole hydrate (415 mg) and 1-(3-dimethylaminopropyl)-3-ethylcarbodiimide hydrochloride (493 mg) in dimethylformamide (10 mL), were added diisopropylethylamine and (2S)-2-pyrrolidinecarbonitrile hydrochloride with cooling on an ice bath. The reaction mixture was stirred at that temperature for 3 hrs.

The reaction mixture was quenched by water and extracted with ethyl acetate. The combined organic layer was washed with 1N HCl, saturated aqueous NaHCO$_3$ and saturated aqueous NaCl, dried over MgSO$_4$, and concentrated in vacuo. The residue was purified with silica gel chromatography (chloroform/methanol=20/1) to give the target compound as a colorless oil (122 mg).

$^1$H-NMR (CDCl$_3$): δ 4.93–4.82(1H, m), 4.29–3.88(4H, m), 3.80–3.49(2H, m), 3.27–3.15(1H, m), 3.00–2.80(1H, m), 2.40–1.53(8H, m), 1.53–1.29(10H, m).

MASS (ES+) m/z: 366.43 (M+1).

EXAMPLE 1-5

(2S)-1-{[(1S,3S,4S,5S,6R)-5,6-Dihydroxy-2-azabicyclo [2.2.2]oct-3-yl]carbonyl}-2-pyrrolidinecarbonitrile hydrochloride To a solution of tert-butyl (1S,3S,4S,5S,6R)-3-{[(2S)-2-cyano-1-pyrrolidinyl]carbonyl}-5,6-dihydroxy-2-azabicyclo[2.2.2]octane-2-carboxylate obtained in Example 1-4 (122 mg) in chloroform (1 mL), was added 4N HCl in dioxane (3 mL) at room temperature. The reaction mixture was stirred for 15 minutes and the organic solvent was removed in vacuo. The residue was triturated with ethyl acetate to give the target compound as a white powder (100 mg).

$^1$H-NMR (DMSO-d$_6$): δ 10.38–9.96(1H, m), 8.47–7.98 (1H, m), 4.95–4.65(1H, m), 4.58–3.1(8H, m), 2.43–0.97(9H, m).

MS (ES+) m/z: 266.42 (M+1).

EXAMPLE 2-1

Ethyl (2Z)-{[(1R)-1-phenylethyl]imino}acetate

To a (1S)-1-phenylethanamine (77.4 mL), was added a solution of ethyl glyoxylate in toluene (45–50%, 123 mL) at room temperature. After 1 hr, the mixture was evaporated in vacuo. The residue (120 g) was used in the next step without further purification.

$^1$H-NMR (300 MHz, CDCl$_3$): δ 1.35(3, t, J=7.2 Hz), 1.62(3H, d, J=6.7 Hz), 4.34(2H, q, J=7.2 Hz), 4.61(1H, d, J=0.7, 6.7 Hz), 7.21–7.40(5H, m), 7.23(1H, d, J=0.7 Hz).

EXAMPLE 2-2

Ethyl (1S,3S,4R)-2-[(1R)-1-phenylethyl]-2-azabicyclo-(2.2.2)oct-5-ene-3-carboxylate To a suspension of ethyl (2Z)-{[(1R)-1-phenylethyl]imino}acetate obtained in Example 2-1 (205 g) and Molecular sieves 4A (30 g) in CH$_2$Cl$_2$ (2 L), were added trifluoroacetic acid (76.9 mL) and boron trifluoride diethyl etherate (127 mL) dropwise at −70° C. under N$_2$ atmosphere. After 15 minutes, cyclohexadiene (100 mL) was added dropwise. The mixture was stirred at room temperature overnight.

To the reaction mixture cooled by an ice-bath, were added NaHCO$_3$ and water. After 20 minutes, the organic layer was separated and evaporated. The residue was diluted with ethyl acetate (1.5 L) and washed with saturated aqueous NaHCO$_3$ solution. The separated organic layer was extracted with 3N HCl. The aqueous layer was alkalized with saturated aqueous NaHCO$_3$, and then extracted with ethyl acetate. The combined organic layer was washed with brine, dried with MgSO$_4$, and filtrated. The filtrate was concentrated in vacuo. The residue was purified by silica gel column chromatography (ethyl acetate/hexane=1/30) to provide the target compound (220 g) as an oil.

$^1$H-NMR (300 MHz, CDCl$_3$): δ 0.95–1.15(1H, m), 1.12 (3H, t, J=7.2 Hz), 1.22–1.35(1H, m), 1.30(3H, d, J=6.6 Hz), 1.52–1.65(1H, m), 1.96–2.10(1H, m), 2.68–2.76(1H, m), 2.89(1H, br-s), 3.43(1H, q, J=6.6 Hz), 3.62 1H, br-s), 3.97(2H, q, J=7.2 Hz), 6.26(1H, ddd, J=1.1, 5.2, 7.9 Hz), 6.39(1H, ddd, J=1.4, 6.6, 7.9 Hz), 7.14–7.29(3H, m), 7.41 (2H, br-d, J=7.2 Hz).

MASS (ES+) m/e: 286 (M+1).

EXAMPLE 2-3

Ethyl (1S,3S,4S,5R)-5-hydroxy-2-[(1R)-1-phenyl-ethyl]-2-azabicyclo[2.2.2]octane-3-carboxylate To a solution of ethyl (1S,3S,4R)-2-[(1R)-1-phenylethyl]-2-azabicyclo-[2.2.2]oct-5-ene-3-carboxylate obtained in Example 2-2 (5.0 g) in tetrahydrofuran (50 mL), was added borane-tetrahydrofuran complex (1.0M in tetrahydrofuran, 17.5 mL) with cooling on an ice bath under $N_2$ atmosphere. After 10 minutes, the bath was removed and the mixture was stirred overnight at room temperature. To this mixture, 3N aqueous NaOH solution (8 mL) and 30% $H_2O_2$ (8 mL) were added with cooling on an ice bath.

After 20 minutes, NaCl was added to the mixture, and then the organic layer was separated. The organic layer was washed with brine, dried over $Na_2SO_4$, and evaporated in vacuo. The residue was purified by silica gel column chromatography (ethyl acetate/hexane=1/2) to provide the diastereomeric mixture (4.05 g) of the target compound as oil. Further purification was not attempted.

$^1$H-NMR (300 MHz, CDCl$_3$): δ 1.04(3H, t, J=7.2 Hz), 1.16–2.05(6H, m), 1.33(3H, d, J=6.6 Hz),2.35–2.48(1H, m), 3.10(1H, br-s), 3.17(1H, br-s), 3.56(1H, q, J=6.6 Hz), 3.89 (2H, q, J=7.2 Hz), 4.05–4.16(1H, m), 7.12–7.32(3H, m), 7.34–7.44(2H, m).

MASS (ES+) m/e: 304 (M+1).

EXAMPLE 2-4

Ethyl (1S,3S,4S,5R)-5-hydroxy-2-azabicyclo[2.2.2]-octane-3-carboxylate

To a solution of ethyl (1S,3S,4S,5R)-5-hydroxy-2-[(1R)-1-phenylethyl]-2-azabicyclo[2.2.2]octane-3-carboxylate obtained in Example 2-3 (22 g) in ethanol (300 mL), was added Pearlman's catalyst (4 g). The mixture was stirred for 3 hrs under $H_2$ atmosphere on 4 atm.

The catalyst was removed by filtration and washed with ethanol. The combined filtrate and washings were concentrated in vacuo. The residue was purified by silica gel column chromatography (methanol/CHCl$_3$=1/20 to 1:5) to provide the diastereomeric mixture of the target compound (8.9 g) as a pale yellow oil. Further purification was not attempted.

$^1$H-NMR (300 MHz, CDCl$_3$): δ 1.24(3H, t, J=7.2 Hz), 1.35–1.45(2H, m), 1.57–2.04(3H, m), 2.06–2.11(1H, m), 2.32–2.44(1H, m), 2.99(1H, br-s), 3.67(1H, t, J=2.3 Hz), 4.16–4.32(3H, m).

MASS (ES+) m/e: 200 (M+1).

EXAMPLE 2-5

(1S,3S,4S,5R)-2-(tert-Butoxycarbonyl)-5-hydroxy-2-azabicyclo[2.2.2]octane-3-carboxylic acid To a solution of ethyl (1S,3S,4S,5R)-5-hydroxy-2-azabicyclo[2.2.2]-octane-3-carboxylate obtained in Example 2-4 (8.9 g) in dioxane (130 mL), was added 1N aqueous NaOH solution (134 mL) at room temperature. After 30 minutes, di-tert-butyl dicarbonate (9.75 g) was added to the mixture with cooling on an ice bath. After 10 minutes, the bath was removed and the mixture was stirred for 3 hrs at room temperature.

The mixture was concentrated in vacuo. The residue was acidified with 1N aqueous HCl and extracted with CHCl$_3$. The organic layer was dried over $Na_2SO_4$, and evaporated in vacuo. The residue was recrystallized from 2-propanol to provide the target compound (6.78 g) as a white crystal.

$^1$H-NMR (300 MHz, DMSO-d$_6$): δ 1.15–1.40(2H, m), 1.33(6H, s), 1.37(3H, s), 1.48–1.62(1H, m), 1.68–2.10(4H, m), 3.80–4.00(3H, m), 4.89(1H, br-s), 12.55(1H, br-s).

MASS (ES–) m/e: 270 (M–1).

EXAMPLE 2-6

Tert-Butyl (1S,3S,4S,5R)-3-{[(2S)-2-aminocarbo-nyl-1-pyrrolidinyl]carbonyl}-5-hydroxy-2-azabicy-clo[2.2.2]octane-2-carboxylate To a solution of (1S,3S,4S,5R)-2-(tert-butoxycarbonyl)-5-hydroxy-2-azabicyclo[2.2.2]octane-3-carboxylic acid obtained in Example 2-5 (4.05 g), (2S)-2-pyrrolidinecarboxamide (1.77 g) and 1-hydroxybenzotriazole hydrate (1.68 g), were added 1-(3-dimethylaminopropyl)-3-ethylcarbodiimide hydrochloride (3.15 g) and N,N-diisopropylethylamine (5.2 mL) with cooling on an ice bath. After 5 minutes, the ice bath was removed and the mixture was stirred overnight at room temperature.

The mixture was concentrated in vacuo. The residue was purified by silica gel column chromatography (methanol/ethyl acetate=1/5) to provide the target compound (8.7 g) as a white solid.

$^1$H-NMR (300 MHz, CDCl$_3$): δ 1.20–2.65(11H, m), 1.35–1.47(9H, m), 3.46–3.80(2H, m), 4.02–4.36(4H, m), 4.67–4.76(1H, m), 5.32 1×9/10H, br-s), 5.53(1×1/10H, br-s).

MASS (ES+) m/e: 368 (M+1).

EXAMPLE 2-7

Tert-Butyl (1S,3S,4S,5R)-3-{[(2S)-2-cyano-1-pyrrolidinyl]carbonyl}-5-hydroxy-2-azabicyclo[2.2.2] octane-2-carboxylate To a solution of tert-butyl (1S,3S,4S,5R)-3-{[(2S)-2-aminocarbonyl-1-pyrrolidinyl]carbonyl}-5-hydroxy-2-azabicyclo[2.2.2]octane-2-carboxylate obtained in Example 2-6 (8.7 g) in tetrahydrofuran (90 mL), were added pyridine (9.58 mL) and trifluoroacetic anhydride (10 mL) with cooling on an ice bath under $N_2$ atmosphere. After 10 minutes, the ice bath was removed and the mixture was stirred for 2 hrs at room temperature.

The mixture was alkalized with saturated aqueous NaHCO$_3$, and then concentrated in vacuo. The residue was diluted with water and extracted with CHCl$_3$. The organic layer was dried over $Na_2SO_4$ and evaporated in vacuo. The residue (9.7 g) was triturated with ethyl acetate and recrystallized from 2-propanol to provide the target compound (4.15 g) as a white crystal.

$^1$H-NMR (300 MHz, DMSO-d$_6$): δ 1.20–1.40(11H, m), 1.42–1.60(1H, m), 1.74–2.30(8H, m), 3.48–3.66(2H, m), 3.84–4.08(2H, m), 4.24(1H, br-s), 4.76–4.90(2H, m).

MASS (ES+) m/e: 350 (M+1).

EXAMPLE 2-8

(2S)-1-{[(1S,3S,4S,5R)-5-hydroxy-2-azabicyclo[2.2.2]oct-3-yl]carbonyl}-2-pyrrolidinecarbonitrile hydrochloride To a solution of tert-butyl (1S,3S,4S,5R)-3-{[(2S)-2-cyano-1-pyrrolidinyl]carbonyl}-5-hydroxy-2-azabicyclo[2.2.2]octane-2-carboxylate obtained in Example 2-7 (2.0 g) in dioxane (10 mL), was added 4N HCl in dioxane (1.43 mL) at room temperature.

After 1 hr, the precipitate was filtered and washed with dioxane. The solid was recrystallized from ethanol-water to provide the target compound (0.83 g) as a white crystal.

$^1$H-NMR (300 MHz, DMSO-$d_6$): δ 1.10–1.26(1H, m), 1.40(1H, br-d, J=14.5 Hz), 1.53–1.68(1H, m), 1.76–2.20 (6H, m), 2.24–2.44(2H, m), 3.43(1H, br-s), 3.46–3.60(1H, m), 3.63–3.75(1H, m), 4.04–4.15(1H, m), 4.19(1H, br-s), 4.86(1H, dd, J=5.9, 7.9 Hz), 5.23(1H, d, J=3.9 Hz).

MASS (ES+) m/e: 250 (M+1).

EXAMPLE 3

(2S)-1-{[(1S,3S,4R,6S)-6-hydroxy-1,4-dimethyl-2-azabicyclo[2.2.2]oct-3-yl]carbonyl}-2-pyrrolidinecarbonitrile Ethyl (1S,3S,4R)-1,4-dimethyl-2-[(1R)-1-phenylethyl]-2-azabicyclo[2.2.2]oct-5-ene-3-carboxylate is used as starting compound, the target compound can be obtained by similar method described in Example 2-3 to 2-8.

EXAMPLE 4

(2S)-1-{[(1R,3S,4R,6S)-6-hydroxy-1-isopropyl-4-methyl-2-azabicyclo[2.2.2]oct-3-yl]carbonyl}-2-pyrrolidinecarbonitrile Ethyl (1S,3S,4R)-1-isopropyl-4-methyl-2-[(1R)-1-phenylethyl]-2-azabicyclo[2.2.2]oct-5-ene-3-carboxylate is used as starting compound, the target compound can be obtained by similar method described in Example 2-3 to 2-8.

EXAMPLE 5-1

Ethyl (1S,3S,4R)-2-[(1R)-1-phenylethyl]-2-azabicyclo[2.2.1]hept-5-ene-3-carboxylate The title compound was obtained from ethyl (2Z)-{[(1R)-1-phenylethyl]-imino}acetate obtained in Example 2-1 in a manner similar to Example 2-2.

$^1$H-NMR (300 MHz, CDCl$_3$): δ 0.95(3H, t, J=7.2 Hz), 1.41(3H, d, J=6.6 Hz), 2.13(1H, d, J=8.3 Hz), 2.20(1H, s), 2.90(1H, m), 3.03(1H, q, J=6.6 Hz), 3.81(2H, q, J=7.2 Hz), 4.30(1H, s), 6.26(1H, m), 6.42(1H, m), 7.12–7.34(5H, m).

EXAMPLE 5-2

Ethyl (1S,3S,4S,6R,7S)-6-hydroxy-7-iodo-2-[(1R)-1-phenylethyl]-2-azabicyclo[2.2.1]heptane-3-carboxylate To a solution of ethyl (1S,3S,4R)-2-[(1R)-1-phenylethyl]-2-azabicyclo[2.2.1]hept-5-ene-3-carboxylate obtained in Example 5-1 (2.44 g) in dimethyl sulfoxide (12 mL) and water (1.5 mL), was added N-iodosuccinimide (2.06 g). The mixture was stirred at room temperature for 30 minutes.

The resulting mixture was diluted with ethyl acetate, and washed successively with sodium hydrogencarbonate solution and brine. The organic layer was dried over NaSO$_4$ and evaporated in vacuo. The residue was chromatographed on silica gel eluting with hexane and ethyl acetate (2:1) to give the target compound (1.99 g) as a solid.

$^1$H-NMR (300 MHz, CDCl$_3$): δ 1.09(3H, t, J=7.2 Hz), 1.41(3H, d, J=6.6 Hz), 1.91(1H, m), 2.01(1H, d, J=10.2 Hz), 2.15(1H, m), 2.73(1H, m), 3.29(1H, m), 3.51(1H, s), 3.71 (1H, q, J=6.6 Hz), 3.80(1H, m), 3.92(1H, q, J=7.2 Hz), 4.18(1H, m), 7.16–7.31(5H, m).

Mass (m/z): 416 (M+1).

EXAMPLE 5-3

Ethyl (1R,3S,4S,6R)-6-hydroxy-2-[(1R)-1-phenylethyl]-2-azabicyclo[2.2.1]heptane-3-carboxylate To a solution of ethyl (1S,3S,4S,6R,7S)-6-hydroxy-7-iodo-2-[(1R)-1-phenylethyl]-2-azabicyclo[2.2.1]heptane-3-carboxylate obtained in Example 5-2 (1.44 g) in toluene (20 mL), was added tributyltin hydride (1.11 g) and 2,2'-azobisisobutyronitrile (228 mg). The mixture was stirred at 100° C. for 30 minutes.

The resulting mixture was diluted with ethyl acetate, and washed successively with water and brine. The organic layer was dried over NaSO$_4$ and evaporated in vacuo. The residue was chromatographed on silica gel eluting with hexane and ethyl acetate (1:1) to give the target compound (951 mg).

$^1$H-NMR (300 MHz, DMSO-$d_6$): δ 1.01(3H, t, J=7.2 Hz), 0.95–1.1(1H, m), 1.28(3H, d, J=6.6 Hz), 1.42–1.57(2H, m), 1.66(1H, m), 2.44(1H, m), 3.10(1H, s), 3.20(1H, m), 3.63 (1H, q, J=6.6 Hz), 3.74(1H, m), 3.84(2H, q, J=7.2 Hz), 4.63(3H, d, J=3. 9 Hz), 7.13–7.27(3H, m), 7.30–7.36(2H, m).

Mass (m/z): 290 (M+1).

EXAMPLE 5-4

Ethyl (1R,3S,4S,6R)-6-hydroxy-2-azabicyclo-[2.2.1]heptane-3-carboxylate

The title compound was obtained from ethyl (1R,3S,4S,6R)-6-hydroxy-2-[(1R)-1-phenylethyl]-2-azabicyclo[2.2.1]heptane-3-carboxylate obtained in Example 5-3 in a manner similar to Example 2-4.

EXAMPLE 5-5

2-tert-Butyl 3-ethyl (1R,3S,4S,6R)-6-hydroxy-2-azabicyclo[2.2.1]heptane-2,3-dicarboxylate To a solution of ethyl (1R,3S,4S,6R)-6-hydroxy-2-azabicyclo-[2.2.1]heptane-3-carboxylate obtained in Example 5-4 (606 mg) in ethanol (10 mL), was added di-tert-butyl dicarbonate (857 mg). The mixture was stirred at room temperature for 2 hrs. The resulting mixture was evaporated in vacuo, and the residue was chromatographed on silica gel eluting with hexane and ethyl acetate (1:1) to give the target compound (602 mg) as a solid.

$^1$H-NMR (300 MHz, CDCl$_3$) (major peak of rotational isomer): δ 1.29(3H, t, J=7.2 Hz), 1.2–1.4(1H, m), 1.39(9H, s), 1.58–1.64(1H, m), 1.78–1.88(1H, m), 1.98(1H, m), 2.20 (1H, d, J=3.3 Hz), 2.76(1H, m), 4.04–4.28(5H, m).

Mass (m/z): 286 (M+1).

EXAMPLE 5-6

(1R,3S,4S,6R)-2-(tert-Butoxycarbonyl)-6-hydroxy-2-azabicyclo[2.2.1]heptane-3-carboxylic acid To a solution of 2-tert-butyl 3-ethyl (1R,3S,4S,6R)-6-hydroxy-2-azabicyclo[2.2.1]heptane-2,3-dicarboxylate obtained in Example 5-5 (249 mg) in dioxane (4.5 mL) and water (1.5 mL), was added lithium hydroxide monohydrate (110 mg). The mixture was stirred at 43° C. for 12 hrs and then 60° C. for 3 hrs. The resulting mixture was evaporated in vacuo. 1N Hydrochloric acid (2.7 mL) was added to the residue, and the mixture was extracted with ethyl acetate. The combined organic phase was washed with brine, dried over $NaSO_4$, and evaporated in vacuo. The residue was triturated with ether to give the target compound (164 mg) as a solid.

$^1$H-NMR (300 MHz, DMSO-$d_6$): δ 1.09–1.20(1H, m), 1.32, 1.39(9H, s), 1.45–1.55(1H, m), 1.66(1H, d, J=11 Hz), 1.72–1.86(1H, m), 2.58–2.66(1H, m), 3.74–3.82(1H, m), 3.85–3.96(2H, m), 4.96–5.03(1H, m).

MASS (ES–) m/z: 256.2 (M–1).

EXAMPLE 5-7 tert-Butyl (1R,3S,4S,6R)-3-{[(2S)-2-cyano-1-pyrrolidinyl]carbonyl}-6-hydroxy-2-azabicyclo[2.2.1]heptane-2-carboxylate To a solution of (1R,3S,4S,6R)-2-(tert-butoxycarbonyl)-6-hydroxy-2-azabicyclo[2.2.1]heptane-3-carboxylic acid obtained in Example 5-6 (90 mg) in N,N-dimethylformamide (1.6 mL), was added (2S)-2-pyrrolidinecarbonitrile hydrochloride (55.7 mg) 1-hydroxy-7-azabenzotriazole (57.2 mg) and 1-(3-dimethylaminopropyl)-3-ethylcarbodiimide (65 mg). The mixture was then stirred at room temperature for 6 hrs. The resulting mixture was evaporated in vacuo and the residue was chromatographed on silica gel eluting with ethyl acetate to give the target compound (85.4 mg) as a solid.

$^1$H-NMR (300 MHz, CDCl$_3$): δ 1.23–1.34(1H, m), 1.34, 1.46(9H, s), 1.64(1H, d, J=9 Hz), 1.82, 1.97(1H, d, J=3 Hz), 1.84–1.94(1H, m), 2.03–2.36(5H, m), 2.66–2.76(1H, m), 3.46–3.69(2H, m), 4.08–4.23(2H, m), 4.23–4.35(1H, m), 4.76–4.90(1H, m).

MASS m/z: 336.

EXAMPLE 5-8

(2S)-1-{[(1R,3S,4S,6R)-6-hydroxy-2-azabicyclo[2.2.1]hept-3-yl]carbonyl}-2-pyrrolidinecarbonitrile hydrochloride The title compound was obtained from tert-butyl (1R,3S,4S,6R)-3-{[(2S)-2-cyano-1-pyrrolidinyl]carbonyl}-6-hydroxy-2-azabicyclo[2.2.1]heptane-2-carboxylate obtained in Example 5-7 in a manner similar to Example 2-8.

$^1$H-NMR (300 MHz, DMSO-$d_6$): δ 1.32(1H, m), 1.62(1H, ddd, J=1.8, 6.9, 13.8 HZ), 1.79(1H, m), 1.88–2.33(5H, m), 3.03(1H, br-s), 3.53–3.71(3H, m), 3.97(1H, m), 4.31(1H, m), 4.82(1H, dd, J=5.1, 8.1 Hz), 5.46(1H, d, J=4.2 Hz).

MASS (ES+) m/z: 236 (M+1).

EXAMPLE 6

(2S)-1-{[(1R,3S,4S)-7-hydroxy-2-azabicyclo[2.2.1]hept-3-yl]carbonyl}-2-pyrrolidinecarbonitrile Ethyl (1R,3S,4R)-2-[(1R)-1-phenylethyl]-2-azabicyclo[2.2.1]hept-7-hydroxy-3-carboxylate is used as starting compound, which can be synthesized from ethyl (1R,3S,4R)-2-[(1R)-1-phenylethyl]-2-azabicyclo[2.2.1]hept-7-oxy-3-carboxylate by reductive reaction, the target compound can be obtained by similar method described in Example 2-4 to 2-8.

EXAMPLE 7-1

4-Methyltetrahydro-2H-pyran-4-ol

To a solution of tetrahydro-4H-pyran-4-one in diethyl ether (10 mL), was added 0.92M methylmagnesium bromide in tetrahydrofuran (6.5 mL) dropwise with cooling on an ice bath. The reaction mixture was warmed to room temperature and stirred for 2 hrs.

The reaction mixture was quenched by adding saturated aqueous $NH_4Cl$, and then NaCl was added. The resulting solution was extracted with chloroform, the combined organic layer was washed with saturated aqueous NaCl, and dried over $MgSO_4$. After removal of the solvent, the target compound was given as a colorless oil (595 mg).

$^1$H-NMR (300 MHz, CDCl$_3$): δ 1.29(3H, s), 1.81–1.46 (4H, m), 3.87–3.61(4H, m).

Mass (ES+) m/z: 117.09 (M+1).

EXAMPLE 7-2

2-Chloro-N-(4-methyltetrahydro-2H-pyran-4-yl)acetamide

To a solution of 4-methyltetrahydro-2H-pyran-4-ol obtained in Example 7-1 in chloroacetonitrile (0.65 mL), was added a mixture of acetic acid and conc. sulfuric acid (1/1, 1.6 mL) dropwise with cooling on an ice bath. The reaction mixture was warmed to room temperature and stirred for 3 hrs.

The reaction mixture was quenched by adding 3N NaOH. The resulting solution was extracted with ethyl acetate. The combined organic layer was washed with saturated aqueous NaCl, dried over $MgSO_4$, and concentrated in vacuo. The residue was purified with silica gel chromatography (hexane/ethyl acetate=1/2) to give the target compound as a white powder (630 mg).

$^1$H-NMR (300 MHz, CDCl$_3$): δ 1.46(3H, s), 1.83–1.67 (2H, m), 2.14–2.00(2H, m), 3.67–3.55(2H, m), 3.81–3.67 (2H, m), 4.00(2H, s), 4.03(1H, br-s).

Mass (ES+) m/z: 192.16 (M+1).

EXAMPLE 7-3

(4-Methyltetrahydro-2H-pyran-4-yl)amine hydrochloride

To a solution of 2-chloro-N-(4-methyltetrahydro-2H-pyran-4-yl)acetamide obtained in Example 7-2 (630 mg) in ethanol/acetic acid (5/1, 6 mL), was added thiourea (275 mg) at room temperature. The reaction mixture was heated at reflux for 2 hrs.

The resulting mixture was cooled to room temperature, and the precipitate was removed by filtration. After removal of the solvent, the residue was triturated with ethanol to give the target compound as a white powder (200 mg).

$^1$H-NMR (300 MHz, DMSO-$d_6$): δ 1.35(3H, s), 1.66–1.53 (2H, m), 1.86–1.70(2H, m), 3.59–3.43(2H, m), 3.83–3.67 (2H, m), 8.25(3H, br-s).

Mass (ES+) m/z: 116.96 (M+1).

EXAMPLE 7-4

Methyl (2S,4R)-4-hydroxy-2-pyrrolidinecarboxylate hydrochloride

Hydroxy proline (155 g) was dissolved in "Hydrogen Chloride, Methanol Reagent 10" (Tokyo Kasei Kogyo Co., Ltd. 900 mL), and this mixture was heated at reflux for 2 hrs. The resulting mixture was cooled to room temperature, and the solvent was removed in vacuo to give the target compound as white powder (215 g).

$^1$H-NMR (in DMSO-$d_6$): δ 2.30–1.99(2H, m), 3.14–2.97 (1H, m), 3.45–3.25(1H, m), 3.76(3H, s), 4.57–4.35(2H, m), 9.23(1H, br-s), 10.32(1H, br-s).

EXAMPLE 7-5

1-tert-Butyl 2-methyl (2S,4R)-4-hydroxy-1,2-pyrrolidinedicarboxylate

To a solution of methyl (2S,4R)-4-hydroxy-2-pyrrolidinecarboxylate hydrochloride obtained in Example 7-4 (215 g) in water/dioxane (800/500 mL) with cooling on an ice bath, was added a solution of di-tert-butyl dicarbonate (271 g) in dioxane (150 mL) and 6N NaOH (400 mL) dropwise. The reaction mixture was stirred at room temperature for 3 hrs and quenched by adding with 1N HCl.

The aqueous layer was extracted with ethyl acetate. The combined organic layer was washed with saturated aqueous NaCl, dried over MgSO$_4$, and concentrated in vacuo. The resulting residue was triturated with hexane to give the target compound as a white powder (200 g).

$^1$H NMR (in CDCl$_3$): δ 1.51–1.32(9H, m), 2.39–1.82(2H, m), 3.79–3.38(5H, m), 4.58–4.31(2H, m).

EXAMPLE 7-6

1-tert-Butyl 2-methyl (2S,4S)-4-fluoro-1,2-pyrrolidinedicarboxylate 1-tert-Butyl 2-methyl (2S,4R)-4-hydroxy-1,2-pyrrolidinedicarboxylate obtained in Example 7-5 (130 g) and cesium fluoride (105 g) were dissolved in dioxane (600 mL), and this mixture was cooled on an ice bath. To the mixture, was added a solution of diethylaminosulfur trifluoride (100 g) in dioxane (20 mL) dropwise for 30 minutes. The reaction mixture was warmed to room temperature and stirred for 5 hrs.

The resulting mixture was added NaHCO$_3$ (400 g). The reaction mixture was quenched with saturated aqueous NaHCO$_3$, and then H$_2$O (1000 mL) and CaCl$_2$ (382 g) in H$_2$O (300 mL) was added. The resulting suspension was filtered and the filtrate was extracted with ethyl acetate. The combined organic layer was washed with saturated aqueous NaCl, dried over MgSO$_4$, and concentrated in vacuo to give the target compound as an yellow oil (127.5 g). Further purification was not attempted.

$^1$H-NMR (in CDCl$_3$): δ 1.55–1.35(9H, m), 2.62–2.16(2H, m), 3.94–3.49(5H, m), 4.60–4.36(1H, m), 5.20(1H, br-d, J=52.8 Hz).

EXAMPLE 7-7

(2S,4S)-1-(tert-butoxycarbonyl)-4-fluoro-2-pyrrolidinecarboxylic acid

The crude product of 1-tert-butyl 2-methyl (2S,4S)-4-fluoro-1,2-pyrrolidinedicarboxylate obtained in Example 7-6 (127.5 g) was dissolved in methanol (400 mL) and then 1N NaOH (800 mL) was added at room temperature.

After stirring for 1.5 hrs, the resulting mixture was washed with diethyl ether, acidified with 1N HCl (1000 mL) and then was extracted with ethyl acetate. The combined organic layer was washed with saturated aqueous NaCl, dried over MgSO$_4$, and concentrated in vacuo. The resulting residue was triturated with ethyl acetate to give the target compound as a white powder (64 g).

$^1$H-NMR (in CDCl$_3$): δ 1.62–1.31(9H, m), 2.94–2.09(2H, m), 4.01–3.44(2H, m), 4.66–4.37(1H, m), 5.22(1H, br-d, J=51.9 Hz).

EXAMPLE 7-8 tert-Butyl (2S,4S)-2-aminocarbonyl-4-fluoro-1-pyrrolidinecarboxylate

To a mixture of (2S,4S)-1-(tert-butoxycarbonyl)-4-fluoro-2-pyrrolidinecarboxylic acid obtained in Example 7-7 (66 g) and 1-hydroxybenzotriazole hydrate (45 g) in acetonitrile (1500 mL) with cooling on an ice bath, was added 1-(3-dimethylaminopropyl)-3-ethylcarbodiimide hydrochloride (82 g).

After the mixture was stirred for 45 minutes, 28% aqueous NH$_3$ (43 mL) was added at that temperature. The resulting mixture was warmed to room temperature and stirred for 15 minutes. The reaction mixture was filtered and the filtrate was evaporated in vacuo. After dilution with ethyl acetate, the reaction mixture was washed with 1N HCl, saturated aqueous NaHCO$_3$ and saturated aqueous NaCl, dried over MgSO$_4$, and filtered. After removal of the solvent, the target compound was obtained as a white powder (46 g).

$^1$H-NMR (in CDCl$_3$): δ 1.58–1.36(9H, m), 2.99–2.02(2H, m), 3.99–3.43(2H, m), 4.57–4.23(1H, m), 5.23(1H, br-d, J=51.6 Hz), 5.69–5.40(1H, m), 6.79–6.05(1H, m).

Mass (ES+) m/z: 233.10 (M+1).

EXAMPLE 7-9

(2S,4S)-4-Fluoro-2-pyrrolidinecarboxamide hydrochloride tert-Butyl (2S,4S)-2-aminocarbonyl-4-fluoro-1-pyrrolidinecarboxylate obtained in Example 7-8 (46 g) was dissolved in 4N HCl in dioxane (200 mL) and the resulting mixture was stirred for 10 minutes at room temperature. After removal of the solvent, the resulting residue was triturated with ethyl acetate to give the target compound as a white powder (34 g).

$^1$H-NMR (in DMSO-$d_6$): δ 2.84–2.00(2H, m), 4.10–3.09 (2H, m), 4.44–4.15(1H, m), 5.39(1H, br-d, J=52.5 Hz), 7.73(1H, br-s), 8.09(1H, br-s), 8.76(1H, br-s), 10.62(1H, br-s).

Mass (ES+) m/z: 132.94 (M+1).

EXAMPLE 7-10

(2S,4S)-1-Chloroacetyl-4-fluoro-2-pyrrolidinecarboxamide

To a mixture of (2S,4S)-4-fluoro-2-pyrrolidinecarboxamide hydrochloride obtained in Example 7-9 (33 g) and sodium 2-ethylhexanoate (70 g) in tetrahydrofuran (500 mL) with cooling on an ice bath, was added chloroacetyl chloride. After stirring for 2 hrs, the resulting residue was then poured onto buchner funnel/filter paper and washed with ethyl acetate. The solvent was removed in vacuo and the resulting residue was triturated with diethyl ether to give the target compound as a white powder (34 g).

$^1$H-NMR (in CDCl$_3$): δ 2.58–2.03(1H, m), 3.05–2.58(1H, m), 4.17–3.68(4H, m), 4.85–4.54(1H, m), 5.36(1H, br-d, J=52.5 Hz), 5.88–5.49(1H, m), 6.63–6.19(1H, m).

EXAMPLE 7-11

(2S,4S)-1-Chloroacetyl-4-fluoro-2-pyrrolidinecarbonitrile

To a solution of (2S,4S)-1-chloroacetyl-4-fluoro-2-pyrrolidinecarboxamide obtained in Example 7-10 (34 g) in tetrahydrofuran (800 mL), was added trifluoroacetic anhydride (28 mL) at room temperature. After stirring for 15 minutes, the resulting mixture was concentrated in vacuo. The resulting residue was triturated with ethyl acetate to give the target compound as a white powder (22 g)

$^1$H-NMR (in CDCl$_3$): δ 2.52–2.22(1H, m), 2.87–2.59(1H, m), 4.33–3.75(4H, m), 5.12–4.87(1H, m), 5.41(1H, br-d, J=50.7 Hz).

EXAMPLE 7-12

(2S,4S)-4-Fluoro-1-{[(4-methyltetrahydro-2H-pyran-4-yl)amino]acetyl}-2-pyrrolidinecarbonitrile To a mixture of (4-methyltetrahydro-2H-pyran-4-yl)amine hydrochloride obtained in Example 7-3 (90 mg) and K$_2$CO$_3$ (100 mg) in tetrahydrofuran (3 mL) cooled on an ice bath, were added (2S,4S)-1-chloroacetyl-4-fluoro-2-pyrrolidinecarbonitrile obtained in Example 7-11 (100 mg) and a catalytic amount of NaI. The reaction mixture was warmed to room temperature and stirred for 23 hrs.

The reaction was quenched with pouring H$_2$O. The aqueous layer was saturated with NaCl and then extracted three times with chloroform. The combined organic layer was dried over MgSO$_4$, filtered, and the solvent was removed in vacuo. The residue was purified with silica gel chromatography (ethyl acetate/methanol=9/1). After removal of the solvent in vacuo, the residue was triturated by 2-propanol to give the target compound as a white powder (75 mg).

$^1$H-NMR (300 MHz, DMSO-d$_6$): δ 1.04(3H, s), 1.58–1.30 (4H, m), 1.89–1.58(1H, br-s), 2.70–2.22(2H, m), 3.55–3.13 (4H, m), 4.10–3.55(4H, m), 5.05–4.89(1H, m), 5.66–5.33 (1H, m).

Mass (ES+) m/z: 270.36 (M+1).

EXAMPLE 8-1

4-Methyltetrahydro-2H-thiopyran-4-ol

The title compound was obtained from tetrahydro-4H-thiopyran-4-one in a manner similar to Example 7-1.

$^1$H-NMR (300 MHz, CDCl$_3$): δ 1.23(3H, s), 1.93–1.58 (4H, m), 3.22–2.30(4H, m).

EXAMPLE 8-2

2-Chloro-N-(4-methyltetrahydro-2H-thiopyran-4-yl)acetamide

The title compound was obtained from 4-methyltetrahydro-2H-thiopyran-4-ol obtained in Example 8-1 in a manner similar to Example 7-2.

$^1$H-NMR (300 MHz, CDCl$_3$): δ 1.41(3H, s), 1.91–1.70 (2H, m), 2.47–2.32(2H, m), 2.61–2.47(2H, m), 2.84–2.64 (2H, m), 3.99(2H, s), 6.27(1H, br-s).

Mass (ES+) m/z: 208.26 (M+1).

EXAMPLE 8-3

(4-Methyltetrahydro-2H-thiopyran-4-yl)amine hydrochloride

The title compound was obtained from 2-chloro-N-(4-methyltetrahydro-2H-thiopyran-4-yl) acetamide obtained in Example 8-2 in a manner similar to Example 7-3.

$^1$H-NMR (300 MHz, DMSO-d$_6$): δ 1.26(3H, s), 2.01–1.81 (4H, m), 2.77–2.59(4H, m), 8.24(3H, br-s).

Mass (ES+) m/z: 132.02 (M+1).

EXAMPLE 8-4

(2S,4S)-4-Fluoro-1-{[(4-methyltetrahydro-2H-thiopyran-4-yl)amino]acetyl}-2-pyrrolidinecarbonitrile The title compound was obtained from (2S,4S)-1-chloroacetyl-4-fluoro-2-pyrrolidinecarbonitrile obtained in Example 7-11 and (4-methyltetrahydro-2H-thiopyran-4-yl) amine hydrochloride obtained in Example 8-3 in a manner similar to Example 7-12.

$^1$H-NMR (300 MHz, DMSO-d$_6$): δ 0.97(3H, s), 1.90–1.45 (5H, m), 2.68–2.23(4H, m), 2.94–2.70(2H, m), 4.13–3.12 (4H, m), 5.15–4.86(1H, m), 5.75–5.26(1H, m).

Mass (ES+) m/z: 286.34 (M+1).

EXAMPLE 9-1

2,6-Dimethyltetrahydro-4H-pyran-4-one 2,6-Dimethyl-4H-pyran-4-one (4 g) was dissolved in ethanol (20 mL) and 10% Pd/C (400 mg) was added. The mixture was hydrogenated under H$_2$ (1 atm) at room temperature for 25 hrs.

The catalyst was filtered through a celite pad and washed with ethanol. The filtrate was concentrated in vacuo, and the residue was purified with silica gel chromatography (hexane/ethyl acetate=4/1) to give the target compound as a colorless oil (2.08 g).

$^1$H-NMR (300 MHz, CDCl$_3$): δ 1.33(3H, d, J=6.0 Hz), 2.22(1H, dd, J=11.4, 14.4 Hz), 2.36(1H, dd, J=2.7, 14.4 Hz), 3.74(1H, ddq, J=2.7, 6.0, 11.4 Hz).

EXAMPLE 9-2

2,4,6-Trimethyltetrahydro-2H-pyran-4-ol

The title compound was obtained from 2,6-dimethyltetrahydro-4H-pyran-4-one obtained in Example 9-1 in a manner similar to Example 7-1.

¹H-NMR (300 MHz, CDCl₃): δ 1.73–1.10(14H, m), 4.01–3.36(2H, m).

EXAMPLE 9-3

2-Chloro-N-(2,4,6-trimethyltetrahydro-2H-pyran-4-yl)acetamide

The title compound was obtained from 2,4,6-trimethyltetrahydro-2H-pyran-4-ol obtained in Example 9-2 in a manner similar to Example 7-2.

¹H-NMR (300 MHz, CDCl₃): δ 1.29–1.10(8H, m), 1.41 (3H, s), 2.26–2.06(2H, m),3.71–3.51(2H, m), 3.99(2H, s), 6.35(1H, br-s).

Mass (ES+) m/z: 220.20 (M+1).

EXAMPLE 9-4

(2,4,6-Trimethyltetrahydro-2H-pyran-4-yl)amine

To a solution of 2-chloro-N-(2,4,6-trimethyltetrahydro-2H-pyran-4-yl) acetamide obtained in Example 9-3 (1.85 g) in ethanol/acetic acid (5/1, 15 mL), was added thiourea (705 mg) at room temperature. The reaction mixture was heated at reflux for 2 hrs.

The resulting mixture was cooled to room temperature, and the precipitate was removed by filtration. After removal of the solvent, the residual solid was neutralized with saturated aqueous NaHCO₃ and extracted with chloroform. The combined organic layer was dried with MgSO₄. After removal of the solvent, the target compound was given as a colorless oil (910 mg).

¹H-NMR (300 MHz, CDCl₃): δ 1.61–0.99(15H, m), 3.85–3.43(2H, m).

Mass (ES+) m/z: 144.09 (M+1).

EXAMPLE 9-5

(2S,4S)-4-Fluoro-1-({[2,4,6-trimethyltetrahydro-2H-pyran-4-yl]amino}acetyl)-2-pyrrolidinecarbonitrile To a mixture of (2,4,6-Trimethyltetrahydro-2H-pyran-4-yl)amine obtained in Example 9-4 (900 mg) and K₂CO₃ (1.2 g) in tetrahydrofuran (10 mL) cooled on an ice bath, were added (2S,4S)-1-(chloroacetyl)-4-fluoro-2-pyrrolidinecarbonitrile obtained in Example 7-11 (700 mg) and a catalytic amount of NaI. The reaction mixture was warmed to room temperature and stirred for 65 hrs.

The reaction mixture was quenched with pouring H₂O. The aqueous layer was saturated with NaCl and then extracted three times with chloroform. The combined organic layer was dried over MgSO₄, filtered, and the solvent was removed in vacuo. The residue was purified with silica gel chromatography (ethyl acetate/methanol=9/1). After removal of the solvent in vacuo, the residue was triturated by diethylether to give the target compound as a white powder (465 mg).

¹H-NMR (300 MHz, CDCl₃): δ 1.28–1.00(11H, m), 1.79–1.45(3H, m), 2.54–2.17(1H, m), 2.88–2.59(1H, m), 4.12–3.20(6H, m), 5.14–4.90(1H, m), 5.60–5.21(1H, m).

Mass (ES+) m/z: 298.31 (M+1).

EXAMPLE 10-1

1-Benzyl-4-methyl-4-piperidinol

Under nitrogen atmosphere, methylmagnesium bromide (3.0M solution in diethyl ether, 10.8 mL) was diluted with tetrahydrofuran (110 mL) with cooling on an ice bath. To the solution, was added dropwise a solution of 1-benzyl-4-piperidinone (5.6 g) in tetrahydrofuran (40 mL), and the mixture was stirred for 1 hr.

The reaction mixture was quenched by adding 1N hydrochloric acid. The aqueous layer was neutralized with sodium hydrogencarbonate and extracted with ethyl acetate three times. The combined organic extracts were washed with brine, dried over MgSO₄, and concentrated. The residue was purified by silica gel chromatography (eluent: ethyl acetate/methanol=50/1) to give the title compound as a pale yellow oil (3.34 g).

¹H-NMR (300 MHz, CDCl₃): δ 1.21(1H, br-s), 1.24(3H, s), 1.54–1.73(4H, m), 2.33–2.41(2H, m), 2.53–2.60(2H, m), 3.52(2H, s), 7.22–7.33(5H, m).

Mass (ES+) m/z: 206 (M+1).

EXAMPLE 10-2

N-(1-Benzyl-4-methyl-4-piperidinyl)acetamide

To a solution of 1-benzyl-4-methyl-4-piperidinol obtained in Example 10-1 (3.34 g) in acetonitrile (19 mL) was added dropwise conc. sulfuric acid (16 mL) with cooling on an ice bath. The mixture was warmed to 20° C. and stirred for 15 hrs. After cooling, the reaction mixture was quenched by adding 3N potassium hydroxide solution, and the resulting solution (pH9) was extracted with ethyl acetate three times. The combined organic extracts were washed with brine, dried over MgSO₄, and concentrated. The residual solid was triturated with ether to give the title compound as a white powder (3.55 g).

¹H-NMR (300 MHz, CDCl₃): δ 1.39(3H, s), 1.61–1.71 (2H, m), 1.95(3H, s), 1.98–2.06(2H, m), 2.18–2.27(2H, m), 2.52–2.60(2H, m), 3.49(2H, s), 5.10(1H, br-s), 7.22–7.33 (5H, m).

Mass (ES+) m/z: 247 (M+1).

EXAMPLE 10-3

1-Benzyl-4-methyl-4-piperidinamine

A mixture of N-(1-benzyl-4-methyl-4-piperidinyl)acetamide obtained in Example 10-2 (3.45 g) and conc. HCl (41 mL) was heated under reflux with stirring for 72 hrs. After cooling, the mixture was quenched by adding 3N potassium hydroxide solution, and the resulting solution (pH11) was extracted with chloroform. The organic layer was washed with brine, dried over MgSO₄, and concentrated to give the title compound as a pale brown oil (2.86 g).

¹H-NMR (300 MHz, CDCl₃): δ 1.11(3H, s), 1.41–1.49 (2H, m), 1.56–1.65(2H, m), 2.35–2.51(4H, m), 3.52(2H, s), 7.22–7.34(5H, m).

Mass (ES+) m/z: 205 (M+1).

EXAMPLE 10-4 tert-Butyl (1-benzyl-4-methyl-4-piperidinyl)carbamate

To a solution of 1-benzyl-4-methyl-4-piperidinamine obtained in Example 10-3 (3.73 g) in 1,4-dioxane (65 mL), were added 1N sodium hydroxide solution (18.3 mL) and di-tert-butyl dicarbonate (3.98 g). The mixture was stirred at 20° C. for 12 hrs.

The resulting mixture was evaporated in vacuo, and the residue was partitioned between water and chloroform. The organic layer was washed with brine, dried over $MgSO_4$, and concentrated. The residue was chromatographed on silica gel eluting with hexane and ethyl acetate (1:1) to give the title compound as a white solid (3.68 g).

$^1$H-NMR (300 MHz, $CDCl_3$): δ 1.33(3H, s), 1.44(9H, s), 1.56–1.66(2H, m), 1.88–1.99(2H, m), 2.20–2.30(2H, m), 2.50–2.60(2H, m), 3.50(2H, s), 4.32(1H, br-s), 7.22–7.34 (5H, m).

Mass (ES+) m/z: 305 (M+1).

EXAMPLE 10-5 tert-Butyl (4-methyl-4-piperidinyl)carbamate tert-Butyl (1-benzyl-4-methyl-4-piperidinyl)-carbamate obtained in Example 10-4 (1.01 g) was dissolved in methanol (20 mL), and 20% Pd(OH)$_2$ on carbon (300 mg) was added. The mixture was stirred under hydrogen atmosphere (4 atm) at 20° C. for 2 hrs. The reaction mixture was diluted with ethyl acetate, filtered through a pad of Celite, and concentrated. The residual solid was triturated with hexane to give the title compound as white crystals (425 mg)

$^1$H-NMR (300 MHz, $CDCl_3$): δ 1.35(3H, s), 1.45(9H, s), 1.48–1.57(2H, m), 1.66(1H, br-s), 1.85–1.98(2H, m), 2.78–2.85(4H, m), 4.38(1H, br-s).

Mass (ES+) m/z: 215 (M+1).

EXAMPLE 10-6 tert-Butyl [4-methyl-1-(2-pyrazinyl)-4-piperidinyl]-carbamate

To a mixture of tert-butyl (4-methyl-4-piperidinyl)carbamate obtained in Example 10–5 (415 mg) and potassium carbonate (321 mg) in N,N-dimethylformamide (4.5 mL), was added chloropyrazine (665 mg). The mixture was heated at 100° C. with stirring for 24 hrs. The resulting mixture was partitioned between saturated aqueous sodium hydrogencarbonate and ethyl acetate. The organic layer was washed with water and brine, dried over $MgSO_4$, and concentrated in vacuo. The residue was chromatographed on silica gel eluting with hexane and ethyl acetate (2:1) to give the title compound as a pale yellow oil (566 mg).

$^1$H-NMR (300 MHz, $CDCl_3$): δ 1.40(3H, s), 1.44(9H, s), 1.66(2H, ddd, J=14, 10, 4 Hz), 2.11(2H, br-d, J=14 Hz), 3.33(2H, ddd, J=14, 10, 3 Hz), 3.87(2H, ddd, J=14, 4, 4 Hz), 4.43(1H, br-s), 7.82(1H, d, J=2 .6 Hz), 8.05(1H, dd, J=2.6, 1.5 Hz), 8.16(1H, d, J=1.5 Hz).

Mass (ES+) m/z: 293 (M+1).

EXAMPLE 10-7

4-Methyl-1-(2-pyrazinyl)-4-piperidinamine

To a solution of tert-butyl [4-methyl-1-(2-pyrazinyl)-4-piperidinyl]carbamate obtained in Example 10-6 (508 mg) in dichloromethane (1 mL), was added trifluoroacetic acid (5 mL), and the mixture was stirred for 30 minutes at 20° C. The resulting mixture was evaporated in vacuo. The residue was neutralized with sodium hydrogencarbonate and extracted with chloroform three times. The organic layer was washed with brine, dried over $MgSO_4$, and concentrated to give the title compound as a pale yellow solid (281 mg).

$^1$H-NMR (300 MHz, $CDCl_3$): δ 1.21(3H, s), 1.36(2H, br-s), 1.47–1.57(2H, m), 1.65(2H, ddd, J=13.2, 8.4, 4.4 Hz), 3.54–3.73(4H, m), 7.80(1H, d, J=2.6 Hz), 8.05(1H, dd, J=2.6, 1.5 Hz), 8.17(1H, d, J=1.5 Hz).

Mass (ES+) m/z: 193 (M+1).

EXAMPLE 10-8

(2S,4S)-4-Fluoro-1-({[4-methyl-1-(2-pyrazinyl)-4-piperidinyl]amino}acetyl)-2-pyrrolidinecarbonitrile To a mixture of 4-methyl-1-(2-pyrazinyl)-4-piperidinamine obtained in Example 10-7 (90 mg) and potassium carbonate (78 mg) in N,N-dimethylformamide (1.5 mL), were added a solution of (2S,4S)-1-chloroacetyl-4-fluoro-2-pyrrolidinecarbonitrile obtained in Example 7-11 (89 mg) in N,N-dimethylformamide (0.5 mL) and a catalytic amount of sodium iodide. The mixture was heated at 40° C. with stirring for 2 hrs.

The resulting mixture was partitioned between saturated aqueous sodium hydrogencarbonate and ethyl acetate. The organic layer was washed with water and brine, dried over $MgSO_4$, and concentrated in vacuo. The residue was purified by silica gel chromatography (eluent: chloroform/methanol=5/1). After removal of the solvent, the residual solid was triturated with ethanol to give the title compound as white crystals (58 mg).

$^1$H-NMR (300 MHz, DMSO-$d_6$): δ 1.06(3H, s), 1.39–1.52 (2H, m), 1.53–1.65(2H, m), 1.73–1.92(1H, m), 2.27–2.61 (2H, m), 3.22–3.61(4H, m), 3.61–4.06(4H, m), 4.94–5.00 (1H, m), 5.32–5.61(1H, m), 7.77(1H, d, J=2.6 Hz), 8.03–8.06(1H, m), 8.29–8.32(1H, m).

Mass (ES+) m/z: 347 (M+1).
MP: 166–167° C.

EXAMPLE 11

(2S,4S)-4-Fluoro-1-({[(1R,5S)-3-methyl-8-(2-pyrazinyl)-8-azabicyclo[3.2.1]oct-3-yl]amino}acetyl)-2-pyrrolidinecarbonitrile The title compound was prepared from [(1R,5S)-3-methyl-8-(2-pyrazinyl)-8-azabicyclo[3.2.1]oct-3-yl]amine in a similar manner to that of Example 10-8.

$^1$H-NMR (300 MHz, DMSO-$d_6$): δ 0.80(3H, s), 1.57–1.75 (4H, m), 1.76–1.87(2H, m), 2.15–2.30(2H, m), 2.32–2.61 (2H, m), 3.19–3.40(2H, m), 3.45–4.03(2H, m), 4.50(2H, br-s), 4.96–5.01(1H, m), 5.34–5.61(1H, m), 7.74(1H, d, J=2. 6 Hz), 8.05(1H, dd, J=2.6, 1.5 Hz), 8.17(1H, d, J=1.5 Hz).

Mass (ES+) m/z: 373 (M+1).

EXAMPLE 12-1 tert-Butyl (1R,3S,4S,6R)-3-{[(2S)-2-cyano-1-pyrrolidinyl]carbonyl}-6-[(methylsulfonyl)oxy]-2-azabicyclo[2.2.1]heptane-2-carboxylate The title compound was prepared from tert-butyl (1R,3S,4S,6R)-3-{[(2S)-2-cyano-1-pyrrolidinyl]carbonyl}-6-hydroxy-2-azabicyclo[2.2.1]heptane-2-carboxylate obtained in Example 5-7 in a similar manner to that of Example 29-1 described later.

$^1$H-NMR (300 MHz, CDCl$_3$): δ 1.35 and 1.47(9H, s), 1.4–1.5(1H, m), 1.70–1.93(2H, m), 2.05–2.55(5H, m), 2.79 (1H, m), 3.03 and 3.05(3H, m), 3.52–3.68(2H, m), 4.18–4.27(1H, m), 4.52(1H, m), 4.88(1H, m).

MASS (ES+) m/z: 414 (M+1).

EXAMPLE 12-2 tert-Butyl (1R,3S,4R,6R)-3-{[(2S)-2-cyano-1-pyrrolidinyl]carbonyl}-6-(1-pyrrolidinyl)-2-azabicyclo[2.2.1]heptane-2-carboxylate To a solution of tert-butyl (1R,3S,4S,6R)-3-{[(2S)-2-cyano-1-pyrrolidinyl]carbonyl}-6-[(methylsulfonyl) oxy]-2-azabicyclo[2.2.1]heptane-2-carboxylate obtained in Example 12-1 (153 mg) in dimethylformamide (2.0 mL), was added pyrrolidine (79 mg). The mixture was stirred at 80° C. for 1 hr. The resulting mixture was evaporated in vacuo and the residue was chromatographed on silica gel eluting with chloroform and methanol (19:1) to give the target compound (91 mg).

$^1$H-NMR (300 MHz, CDCl$_3$): δ 1.36 and 1.46(9H, s), 1.50–1.82(7H, m), 2.06–2.45(6H, m), 2.40–2.65(4H, m), 3.54–3.80(3H, m), 4.20(1H, s), 4.00–4.25(2H, m), 4.83(1H, m).

MASS (ES+) m/z: 389 (M+1).

EXAMPLE 12-3

(2S)-1-{[(1R,3S,4S,6R)-6-(1-Pyrrolidinyl)-2-azabicyclo[2.2.1]hept-3-yl]carbonyl}-2-pyrrolidinecarbonitrile dihydrochloride The title compound was prepared from tert-butyl (1R,3S,4R,6R)-3-{[(2S)-2-cyano-1-pyrrolidinyl]carbonyl}-6-(1-pyrrolidinyl)-2-azabicyclo[2.2.1]heptane-2-carboxylate obtained in Example 12-2 in a similar manner to that of Example 2-8.

$^1$H-NMR (300 MHz, DMSO-d$_6$): δ 1.60(1H, m), 1.70–2.36(7H, m), 2.64(1H, m), 2.77–3.14(3H, m), 3.30–3.70(6H, m), 3.77(1H, m), 3.94(1H, m), 4.14(1H, s), 4.38(1H, s), 4.81(1H, dd, J=5, 8 Hz).

MASS (ES+) m/z: 289 (M+1).

EXAMPLE 13-1

Methyl (1S,3S,4S,6R,7R)-7-fluoro-6-hydroxy-2-[(1R)-1-phenylethyl]-2-azabicyclo[2.2.1]heptane-3-carboxylate To a solution of methyl (1S,3S,4S,6R,7S)-6-hydroxy-7-iodo-2-[(1R)-1-phenylethyl]-2-azabicyclo[2.2.1]heptane-3-carboxylate (100 mg) in acetonitrile (8 mL), was added tetrabutylammonium fluoride hydrate (102 mg). The mixture was stirred at 80° C. for 30 minutes. The resulting mixture was diluted with ethyl acetate, and washed successively with water and brine. The organic layer was dried over sodium sulfate and evaporated in vacuo. The residue was chromatographed on silica gel eluting with hexane and ethyl acetate (1:1) to give the target compound (59.5 mg)

$^1$H-NMR (300 MHz, CDCl$_3$): δ 1.39(3H, d, J=6.6 Hz), 1.63(1H, m), 1.82(1H, m), 2.19(1H, m), 2.76(1H, m), 3.26 (1H, m), 3.47(1H, m), 3.55(1H, s), 3.72(1H, q, J=6.6 Hz), 4.10(1H, m), 4.78(1H, d, J=50 Hz), 7.17–7.35(5H, m).

MASS (ES+) m/z 294 (M+1).

EXAMPLE 13-2

Methyl (1S,3S,4S,6R,7R)-7-fluoro-6-hydroxy-2-azabicyclo[2.2.1]heptane-3-carboxylate The title compound was prepared from methyl (1S,3S,4S,6R,7R)-7-fluoro-6-hydroxy-2-[(1R)-1-phenylethyl]-2-azabicyclo[2.2.1]heptane-3-carboxylate obtained in Example 13-1 in a similar manner to that of Example 2-4.

EXAMPLE 13-3

2-tert-Butyl 3-methyl (1S,3S,4S,6R,7R)-7-fluoro-6-hydroxy-2-azabicyclo[2.2.1]heptane-2,3-dicarboxylate The title compound was prepared from methyl (1S,3S,4S,6R,7R)-7-fluoro-6-hydroxy-2-azabicyclo[2.2.1]heptane-3-carboxylate obtained in Example 13-2 in a similar manner to that of Example 5-5.

$^1$H-NMR (300 MHz, CDCl$_3$): δ 1.39 and 1.47(9H, s), 1.77(1H, m), 1.94(1H, m), 2.20(1H, m), 2.92(1H, m), 3.76 (3H, s), 4.08–4.31(3H, m), 4.95(1H, d, J=50 Hz).

MASS m/z: 312 (M+Na).

EXAMPLE 13-4

(1S,3S,4S,6R,7R)-2-(tert-Butoxycarbonyl)-7-fluoro-6-hydroxy-2-azabicyclo[2.2.1]heptane-3-carboxylic acid The title compound was prepared from 2-tert-butyl 3-methyl (1S,3S,4S,6R,7R)-7-fluoro-6-hydroxy-2-azabicyclo[2.2.1]heptane-2,3-dicarboxylate obtained in Example 13-3 in a similar manner to that of Example 5-6.

$^1$H-NMR (300 MHz, DMSO-d$_6$): δ 1.32 and 1.39(9H, s), 1.62(1H, m), 1.92(1H, m), 2.76(1H, m), 3.88–4.05(3H, m), 4.84–5.08(2H, m).

MASS (ES+) m/z: 276 (M+1).

EXAMPLE 13-5 tert-Butyl (1S,3S,4S,6R)-3-{[(2S)-2-cyano-1-pyrrolidinyl]carbonyl}-7-fluoro-6-hydroxy-2-azabicyclo[2.2.1]heptane-2-carboxylate The title compound was prepared from (1S,3S,4S,6R,7R)-2-(tert-butoxycarbonyl)-7-fluoro-6-hydroxy-2-azabicyclo[2.2.1]heptane-3-carboxylic acid obtained in Example 13-4 in a similar manner to that of Example 5-7.

$^1$H-NMR (300 MHz, CDCl$_3$): δ 1.34 and 1.45(9H, s), 1.65–2.49(6H, m), 2.88(1H, m),3.58(1H, m), 4.16–4.45(2H, m), 4.77–5.07(1H, m).

MASS (ES+) m/z: 354 (M+1).

EXAMPLE 13-6

(2S)-1-{[(1S,3S,4S,6R,7R)-7-Fluoro-6-hydroxy-2-azabicyclo[2.2.1]hept-3-yl]carbonyl}-2-pyrrolidinecarbonitrile hydrochloride The title compound was prepared from tert-butyl (1S,3S,4S,6R)-3-{[(2S)-2-cyano-1-pyrrolidinyl]carbonyl}-7-fluoro-6-hydroxy-2-azabicyclo[2.2.1]heptane-2-carboxylate obtained in Example 13-5 in a similar manner to that of Example 2-8.

$^1$H-NMR (300 MHz, DMSO-d$_6$): δ 1.77(2H, m), 1.90–2.33(4H, m), 3.22(1H, br-s), 3.50–3.66(3H, m), 4.13(1H, m), 4.41(1H, m), 4.82(1H, dd, J=5, 8 Hz), 5.16(1H, d, J=50 Hz), 5.50(1H, br-s).

MASS (ES+) m/z: 254 (M+1).

EXAMPLE 14-1

2-tert-Butyl 3-methyl (1R,3R,4S,6R)-6-hydroxy-2-azabicyclo[2.2.1]heptane-2,3-dicarboxylate To 2-tert-butyl 3-methyl (1R,3S,4S,6R)-6-hydroxy-2-azabicyclo[2.2.1]heptane-2,3-dicarboxylate (3.04 g), was added 1N sodiummethoxide solution in methanol (34 mL). The mixture was stirred at reflux for 4 hrs. To the resulting mixture was added ammonium chloride solution and evaporated in vacuo. Water was added to the residue, and the mixture was extracted with ethyl acetate. The combined organic phase was washed with brine, dried over sodium sulfate, and evaporated in vacuo. The residue was recrystalized from hexane-diethyl ether to give the target compound (1.09 g) as a solid.

$^1$H-NMR (300 MHz, CDCl$_3$): δ 1.39 and 1.47(9H, s), 1.42–2.01(4H, m), 2.68(1H, m), 3.59and 3.69(1H, s), 3.73(3H, s), 3.96–4.17(2H, m).

MASS (ES+) m/z: 272 (M+1).

EXAMPLE 14-2

(1R,3R,4S,6R)-2-(tert-Butoxycarbonyl)-6-hydroxy-2-azabicyclo[2.2.1]heptane-3-carboxylic acid The title compound was prepared from 2-tert-butyl 3-methyl (1R,3R,4S,6R)-6-hydroxy-2-azabicyclo[2.2.1]heptane-2,3-dicarboxylate obtained in Example 14-1 in a similar manner to that of Example 5-6.

$^1$H-NMR (300 MHz, DMSO-d$_6$): δ 1.30(1H, m), 1.31 and 1.40(9H, s), 1.53(1H, m), 1.65(1H, m), 1.84(1H, m), 2.55(1H, m), 3.44(1H, m), 3.69(1H, m), 3.80 and 3.87(1H, br-s), 5.05(1H, m).

MASS (ES−) m/z: 256 (M−1).

EXAMPLE 14-3 tert-Butyl (1R,3R,4S,6R)-3-{[(2S)-2-cyano-1-pyrrolidinyl]carbonyl}-6-hydroxy-2-azabicyclo[2.2.1]heptane-2-carboxylate The title compound was prepared from (1R,3R,4S,6R)-2-(tert-butoxycarbonyl)-6-hydroxy-2-azabicyclo[2.2.1]heptane-3-carboxylic acid obtained in Example 14-2 in a similar manner to that of Example 5-7.

$^1$H-NMR (300 MHz, CDCl$_3$): δ 1.40 and 1.43(9H, s), 1.40–2.78(6H, m), 2.96(1H, m), 3.55–4.21(6H, m).

MASS (ES+) m/z: 336 (M+1).

EXAMPLE 14-4

(2S)-1-{[(1R,3R,4S,6R)-6-hydroxy-2-azabicyclo[2.2.1]hept-3-yl]carbonyl}-2-pyrrolidinecarbonitrile hydrochloride The title compound was prepared from tert-butyl (1R,3R,4S,6R)-3-{[(2S)-2-cyano-1-pyrrolidinyl]carbonyl}-6-hydroxy-2-azabicyclo[2.2.1]heptane-2-carboxylate obtained in Example 14-3 in a similar manner to that of Example 2-8.

$^1$H-NMR (300 MHz, DMSO-d$_6$): δ 1.32–1.55(4H, m), 1.73–1.83(2H, m), 1.90–2.28(2H, m), 2.82(1H, m), 3.70–3.87(4H, m), 4.14–4.25(2H, m), 5.42(1H, br-s).

MASS (ES+) m/z: 236 (M+1).

EXAMPLE 15-1 tert-Butyl (1R,3S,4S,6R)-3-{[(2S)-2-cyano-1-pyrrolidinyl]carbonyl}-6-(2-ethoxy-2-oxoethoxy)-2-azabicyclo[2.2.1]heptane-2-carboxylate The title compound was prepared from tert-butyl (1R,3S,4S,6R)-3-{[(2S)-2-cyano-1-pyrrolidinyl]carbonyl}-6-hydroxy-2-azabicyclo[2.2.1]heptane-2-carboxylate obtained in Example 5-7 in a similar manner to that of Example 35-1 described later.

$^1$H-NMR (300 MHz, CDCl$_3$): δ 1.27(3H, t, J=7 Hz), 1.32 and 1.34(9H, s), 1.44(1H, s), 1.66(1H, m), 1.88(1H, m), 2.05–2.38(5H, m), 2.72(1H, m), 3.55–3.67(2H, m), 3.91(1H, m), 4.03–4.38(6H, m), 4.84(1H, m).

MASS (ES+) m/z: 422 (M+1).

EXAMPLE 15-2

[((1R,3S,4S,6R)-2-(tert-Butoxycarbonyl)-3-{[(2S)-2-cyano-1-pyrrolidinyl]carbonyl}-2-azabicyclo[2.2.1]hept-6-yl)oxy]acetic acid To a solution of tert-butyl (1R,3S,4S,6R)-3-{[(2S)-2-cyano-1-pyrrolidinyl]carbonyl}-6-(2-ethoxy-2-oxoethoxy)-2-azabicyclo[2.2.1]heptane-2-carboxylate obtained in Example 15-1 (249 mg) in dioxane (3 mL) and water (1 mL), was added lithium hydroxide monohydrate (302 mg). The mixture was stirred at room temperature for 1 hr. The resulting mixture was evaporated in vacuo. 1N Hydrochloric acid (1.2 mL) was added to the residue, and the mixture was extracted with ethyl acetate. The combined organic phase was washed with brine, dried over sodium sulfate, and evaporated in vacuo to give the target compound (261 mg).

$^1$H-NMR (300 MHz, CDCl$_3$): δ 1.34 and 1.46(9H, s), 1.45(1H, m), 1.67(1H, m), 1.87(1H, m), 2.05–2.38(5H, m), 2.75(1H, m), 3.45–3.70(2H, m), 3.96(1H, m), 4.05–4.40(4H, m), 4.85(1H, m).

MASS (ES−) m/z: 392 (M−1).

EXAMPLE 15-3 tert-Butyl (1R,3S,4S,6R)-6-(2-amino-2-oxoethoxy)-3-{[(2S)-2-cyano-1-pyrrolidinyl]carbonyl}-2-azabicyclo[2.2.1]heptane-2-carboxylate To a solution of [((1R,3S,4S,6R)-2-(tert-butoxycarbonyl)-3-{[(2S)-2-cyano-1-pyrrolidinyl]carbonyl}-2-azabicyclo[2.2.1]hept-6-yl)oxy]acetic acid obtained in Example 51-2 (260 mg) in dimethylformamide (3.0 mL), was added 28% ammonium hydroxide (0.08 mL), 1-hydroxy-7-azabenzotriazole (117 mg) and 1-(3-dimethylaminopropyl)-3-ethylcarbodiimide hydrochloride (165 mg). The mixture was stirred at room temperature for 12 hrs.

The reaction mixture was diluted with ethyl acetate, and washed successively with 0.5N hydrochloric acid, sodium hydrogen carbonate solution and brine. The organic phase was dried over sodium sulfate and evaporated in vacuo. The residue was chromatographed on silica gel eluting with chloroform and methanol (19:1) to give the target compound (174 mg).

$^1$H-NMR (300 MHz, CDCl$_3$): δ 1.34 and 1.46(9H, s), 1.42(1H, m), 1.62–1.84(2H, m), 2.07–2.38(5H, m), 2.74(1H, m), 3.55–3.68(2H, m), 3.93–4.04(3H, m), 4.24(1H, br-s), 4.85(1H, m), 5.48(1H, br-s), 6.42(1H, br-s).

MASS (ES+) m/z: 393 (M+1).

EXAMPLE 15-4

2-[((1R,3S,4S,6R)-3-{[(2S)-2-Cyano-1-pyrrolidinyl] carbonyl}-2-azabicyclo[2.2.1]hept-6-yl)oxy]acetamide hydrochloride The title compound was prepared from tert-butyl (1R,3S, 4S,6R)-6-(2-amino-2-oxoethoxy)-3-{[(2S)-2-cyano-1-pyrrolidinyl]carbonyl}-2-azabicyclo[2.2.1]heptane-2-carboxylate obtained in Example 15-3 in a similar manner to that of Example 2-8.

$^1$H-NMR (300 MHz, DMSO-d$_6$): δ 1.35–1.57(1H, m), 1.56(1H, m), 1.58–2.35(6H, m), 3.06(1H, m), 3.64(1H, m), 3.82–3.90(3H, m), 4.01(1H, s), 4.33(1H, m), 4.83(1H, m).

MASS (ES+) m/z: 293 (M+1).

EXAMPLE 16-1 tert-Butyl (1R,3S,4S,6R)-6-allyloxy-3-{[(2S)-2-cyano-1-pyrrolidinyl]carbonyl}-2-azabicyclo[2.2.1] heptane-2-carboxylate To a solution of tert-butyl (1R,3S,4S,6R)-3-{[(2S)-2-cyano-1-pyrrolidinyl]carbonyl}-6-hydroxy-2-azabicyclo [2.2.1]heptane-2-carboxylate obtained in Example 5-7 (510 mg) in tetrahydrofuran (5.0 mL), were added 1,4-bis(diphenylphosphino)butane (64.8 mg), tris(dibenzylideneacetone) dipalladium(0)-chloroform adduct (39.3 mg) and allyl ethyl carbonate (0.4 mL). The mixture was stirred at 65° C. for 4 hrs. The resulting mixture was evaporated in vacuo and the residue was chromatographed on silica gel eluting with ethyl acetate to give the target compound (408 mg).

$^1$H-NMR (300 MHz, CDCl$_3$): δ 1.35 and 1.46(9H, s), 1.40(1H, m), 1.62(1H, m), 1.82(1H, m), 2.05–2.37(5H, m), 2.71(1H, m), 3.52–3.67(2H, m), 3.89–4.36(5H, m), 4.84(1H, m), 5.16(1H, m), 5.27(1H, m), 5.91(1H, m).

MASS (ES+) m/z: 376 (M+1).

EXAMPLE 16-2

(2S)-1-{[(1R,3S,4S,6R)-6-Allyloxy-2-azabicyclo [2.2.1]hept-3-yl]carbonyl}-2-pyrrolidinecarbonitrile hydrochloride The title compound was prepared from tert-butyl (1R,3S, 4S,6R)-6-allyloxy-3-{[(2S)-2-cyano-1-pyrrolidinyl]carbonyl}-2-azabicyclo[2.2.1]heptane-2-carboxylate obtained in Example 16-1 in a similar manner to that of Example 2-8.

$^1$H-NMR (300 MHz, DMSO-d$_6$): δ 1.43(1H, m), 1.64(1H, m), 1.84(2H, s), 1.90–2.35(4H, m), 3.06(1H, br-s), 3.63(2H, m), 3.83(1H, m), 3.87–4.08(3H, m), 4.13(1H, d, J=2 Hz), 4.83(1H, dd, J=5, 8 Hz), 5.12–5.31(2H, m), 5.89(1H, m).

MASS (ES+) m/z: 276 (M+1).

EXAMPLE 17-1 tert-Butyl (1R,3S,4S,6R)-3-{[(2S)-2-cyano-1-pyrrolidinyl]carbonyl}-6-(2-oxopropoxy)-2-azabicyclo [2.2.1]heptane-2-carboxylate To a solution of tert-butyl (1R,3S,4S,6R)-6-allyloxy-3-{ [(2S)-2-cyano-1-pyrrolidinyl]carbonyl}-2-azabicyclo[2.2.1] heptane-2-carboxylate obtained in Example 16-1 (277 mg) in dimethylformamide (5.0 mL) and water (0.45 mL), were added palladium(2) chloride (105 mg) and copper(1) chloride (292 mg). The mixture was stirred vigorously in aerobic condition at room temperature for 3 hrs.

The reaction mixture was diluted with ethyl acetate, and washed successively with 0.5N hydrochloric acid, sodium hydrogen carbonate solution and brine. The organic phase was dried over sodium sulfate and evaporated in vacuo. The residue was chromatographed on silica gel eluting with ethyl acetate to give the target compound (117 mg).

$^1$H-NMR (300 MHz, CDCl$_3$): δ 1.35 and 1.47(9H, s), 1.42(1H, m), 1.67(1H, m), 1.86(1H, m), 2.05–2.37(5H, m), 2.14 and 2.17(3H, s), 2.74(1H, m), 3.52–3.67(2H, m), 3.88 (1H, m), 4.07–4.37(4H, m), 4.84(1H, m).

EXAMPLE 17-2

(2S)-1-{[(1R,3S,4S,6R)-6-(2-Oxopropoxy)-2-azabicyclo[2.2.1]hept-3-yl]carbonyl}-2-pyrrolidinecarbonitrile hydrochloride The title compound was prepared from tert-butyl (1R,3S, 4S,6R)-3-{[(2S)-2-cyano-1-pyrrolidinyl]carbonyl}-6-(2-oxopropoxy)-2-azabicyclo[2.2.1]heptane-2-carboxylate obtained in Example 17-1 in a similar manner to that of Example 2-8.

$^1$H-NMR (300 MHz, DMSO-d$_6$): δ 1.47(1H, m), 1.77(1H, m), 1.85(2H, m), 1.95–2.33(4H, m), 2.04(3H, s), 3.06(1H, m), 3.63(2H, m), 3.83(1H, m), 3.97(1H, s), 4.22(2H, s), 4.32(1H, m), 4.83(1H, dd, J=5, 8 Hz).

MASS (ES+) m/z: 292 (M+1).

EXAMPLE 18-1 tert-Butyl (1R,3S,4S,6R)-3-{[(2S)-2-cyano-1-pyrrolidinyl]carbonyl}-6-{2-[(methylsulfonyl)amino]-2-oxoethoxy}-2-azabicyclo[2.2.1]heptane-2-carboxylate To a solution of [((1R,3S,4S,6R)-2-(tert-butoxycarbonyl)-3-{[(2S)-2-cyano-1-pyrrolidinyl]carbonyl}-2-azabicyclo [2.2.1]hept-6-yl)oxy]acetic acid obtained in Example 15-2 (195 mg) in dimethylformamide (2.5 mL), was added 1,1'-carbonyldiimodazole (165 mg). The mixture was stirred at room temperature. After 30 minutes, methanesulfonamide (66 mg) and 1,8-diazabicyclo[5,4,0]undec-7-ene (106 mg) were added, and the resulting mixture was stirred at room temperature for 12 hrs.

The reaction mixture was diluted with ethyl acetate, and washed successively with 0.5N hydrochloric acid and brine. The organic phase was dried over sodium sulfate and evaporated in vacuo. The residue was chromatographed on silica gel eluting with chloroform and methanol (9:1) to give the target compound (171 mg).

$^1$H-NMR (300 MHz, CDCl$_3$): δ 1.35 and 1.48(9H, s), 1.42(1H, m), 1.55–1.85(2H, m), 2.05–2.40(5H, m), 2.77(1H, m), 3.34 and 3.36(3H, s), 3.50–3.68(2H, m), 3.99(1H, m), 4.05–4.38(4H, m), 4.84(1H, m).
MASS (ES–) m/z: 469 (M–1).

EXAMPLE 18-2

2-[((1R,3S,4S,6R)-3-{[(2S)-2-Cyano-1-pyrrolidinyl] carbonyl}-2-azabicyclo[2.2.1]hept-6-yl)oxy]-N-(methylsulfonyl)acetamide hydrochloride The title compound was prepared from tert-butyl (1R,3S, 4S,6R)-3-{[(2S)-2-cyano-1-pyrrolidinyl]carbonyl}-6-{2-[(methylsulfonyl)amino]-2-oxoethoxy}-2-azabicyclo[2.2.1] heptane-2-carboxylate obtained in Example 18-1 in a similar manner to that of Example 2-8.
$^1$H-NMR (300 MHz, DMSO-$d_6$): δ 1.52(1H, m), 1.67(1H, m), 1.78–2.32(6H, m), 3.06(1H, m), 3.27(3H, s), 3.62(2H, m), 3.91(1H, m), 3.95–4.19(3H, m), 4.33(1H, m), 4.83(1H, m).
MASS (ES+) m/z: 371 (M+1).

EXAMPLE 19-1 tert-Butyl (1R,3S,4S,6R)-3-{[(2S)-2-cyano-1-pyrrolidinyl]carbonyl}-6-(2-{[(dimethylamino)sulfonyl] amino}-2-oxoethoxy)-2-azabicyclo[2.2.1]heptane-2-carboxylate The title compound was prepared from [((1R,3S,4S,6R)-2-(tert-butoxycarbonyl)-3-{[(2S)-2-cyano-1-pyrrolidinyl] carbonyl}-2-azabicyclo[2.2.1]hept-6-yl)oxy]acetic acid obtained in Example 15-2 in a similar manner to that of Example 18-1.
$^1$H-NMR (300 MHz, CDCl$_3$): δ 1.34 and 1.47(9H, s), 1.42(1H, m), 1.60–1.82(2H, m), 2.05–2.40(5H, m), 2.77(1H, m), 2.98(3H, s), 2.99(3H, s), 3.50–3.68(2H, m), 3.92–4.38 (5H, m), 4.83(1H, m), 8.53(1H, br-s).
MASS (ES–) m/z: 498 (M–1).

EXAMPLE 19-2

2-[((1R,3S,4S,6R)-3-{[(2S)-2-Cyano-1-pyrrolidinyl] carbonyl}-2-azabicyclo[2.2.1]hept-6-yl)oxy]-N-[(dimethylamino)sulfonyl]acetamide hydrochloride The title compound was prepared from tert-butyl (1R,3S, 4S,6R)-3-{[(2S)-2-cyano-1-pyrrolidinyl]carbonyl}-6-(2-{ [(dimethylamino)sulfonyl]amino}-2-oxoethoxy)-2-azabicyclo[2.2.1]heptane-2-carboxylate obtained in Example 19-1 in a similar manner to that of Example 2-8.
$^1$H-NMR (300 MHz, DMSO-$d_6$): δ 1.49(1H, m), 1.66(1H, m), 1.76–2.32(6H, m), 2.82(6H, s), 3.04(1H, m), 3.62(2H, m), 3.72–4.40(5H, m), 4.83(1H, m).
MASS (ES+) m/z: 400 (M+1).

EXAMPLE 20-1 tert-Butyl (1R,3S,4S,6R)-3-{[(2S)-2-cyano-1-pyrrolidinyl]carbonyl}-6-(2-oxo-2-{[(trifluoromethyl) sulfonyl]amino}ethoxy)-2-azabicyclo[2.2.1]heptane-2-carboxylate The title compound was prepared from [((1R,3S,4S,6R)-2-(tert-butoxycarbonyl)-3-{[(2S)-2-cyano-1-pyrrolidinyl] carbonyl}-2-azabicyclo[2.2.1]hept-6-yl)oxy]acetic acid obtained in Example 15-2 in a similar manner to that of Example 18-1.

$^1$H-NMR (300 MHz, CDCl$_3$): δ 1.31 and 1.46(9H, s), 1.42(1H, m), 1.66(1H, m), 1.80(1H, m), 2.0–2.40(5H, m), 2.77(1H, m), 3.52(1H, m), 3.64(1H, m), 3.80–4.40(5H, m), 4.81(1H, m).
MASS (ES–) m/z: 523 (M–1).

EXAMPLE 20-2

2-[((1R,3S,4S,6R)-3-{[(2S)-2-cyano-1-pyrrolidinyl] carbonyl}-2-azabicyclo[2.2.1]hept-6-yl)oxy]-N-[(trifluoromethyl)sulfonyl]acetamide hydrochloride The title compound was prepared from tert-butyl (1R,3S, 4S,6R)-3-{[(2S)-2-cyano-1-pyrrolidinyl]carbonyl}-6-(2-oxo-2-{[(trifluoromethyl)sulfonyl]amino}ethoxy)-2-azabicyclo[2.2.1]heptane-2-carboxylate obtained in Example 20-1 in a similar manner to that of Example 2-8.
$^1$H-NMR (300 MHz, DMSO-$d_6$): δ 1.45(1H, m), 1.66(1H, m), 1.83(2H, m), 2.02(2H, m), 2.05–2.32(2H, m), 3.03(1H, m), 3.63(2H, m), 3.70–4.16(4H, m), 4.31(1H, m), 4.83(1H, m).
MASS (ES+) m/z: 425 (M+1).

EXAMPLE 21-1 tert-Butyl (1R,3S,4S,6R)-3-{[(2S)-2-cyano-1-pyrrolidinyl]carbonyl}-6-{[(2R)-2,3-dihydroxypropyl] oxy}-2-azabicyclo[2.2.1]heptane-2-carboxylate To a solution of tert-butyl (1R,3S,4S,6R)-6-allyloxy-3-{ [(2S)-2-cyano-1-pyrrolidinyl]carbonyl}-2-azabicyclo[2.2.1] heptane-2-carboxylate obtained in Example 16-1(323 mg) in t-butyl alcohol (4.3 mL) and water (4.3 mL), was added AD-mix-α (1.2 g). The mixture was stirred at 0° C. for 4 hrs. Sodium sulfite (1.0 g) was added to the resulting mixture. The mixture was then evaporated in vacuo. The residue was diluted with ethyl acetate, and washed successively with 0.5N hydrochloric acid, sodium hydrogen carbonate solution and brine. The organic phase was dried over sodium sulfate and evaporated in vacuo. The residue was chromatographed on silica gel eluting with chloroform and methanol (19:1) to give the target compound (234 mg).
$^1$H-NMR (300 MHz, CDCl$_3$): δ 1.34 and 1.46(9H, s), 1.65(1H, m), 1.77(1H, m), 2.05–2.37(6H, m), 2.53(1H, m), 2.73(1H, m), 3.50–3.77(6H, m), 3.79–3.98(2H, m), 4.17–4.37(2H, m), 4.84(1H, m).
MASS (ES+) m/z: 410 (M+1).

EXAMPLE 21-2

(2S)-1-[((1R,3S,4S,6R)-6-{[(2R)-2,3-dihydroxypropyl]oxy}-2-azabicyclo[2.2.1]hept-3-yl)carbonyl]-2-pyrrolidinecarbonitrile hydrochloride The title compound was prepared from tert-butyl (1R,3S, 4S,6R)-3-{[(2S)-2-cyano-1-pyrrolidinyl]carbonyl}-6-{ [(2R)-2,3-dihydroxypropyl]oxy}-2- azabicyclo[2.2.1]heptane-2-carboxylate obtained in Example 21-1 in a similar manner to that of Example 2-8.
$^1$H-NMR (300 MHz, DMSO-$d_6$): δ 1.43(1H, m), 1.64(1H, m), 1.70–2.32(6H, m), 3.03(1H, m), 3.20–3.96(9H, m), 4.34(1H, m), 4.83(1H, m).
MASS (ES+) m/z: 310 (M+1).

EXAMPLE 22-1 tert-Butyl (1R,3S,4S)-3-{[(2S)-2-cyano-1-pyrrolidinyl]carbonyl}-6-oxo-2-azabicyclo[2.2.1]heptane-2-carboxylate To a solution of tert-butyl (1R,3S,4S,6R)-3-{[(2S)-2-cyano-1-pyrrolidinyl]carbonyl}-6-hydroxy-2-azabicyclo[2.2.1]heptane-2-carboxylate obtained in Example 5-7 (353 mg) in dichloromethane (10 mL), were added sodium hydrogencarbonate (177 mg) and Dess-Martin periodinane (692 mg). The mixture was stirred at room temperature for 4 hrs.

The resulting mixture was evaporated in vacuo. To the residue, sodium thiosulfate solution and sodium hydrogen carbonate solution were added. The mixture was extracted with ethyl acetate. The combined organic phase was washed with brine, dried over sodium sulfate, and evaporated in vacuo. The residue was triturated with ethyl acetate to give the target compound (284 mg) as a solid.

$^1$H-NMR (300 MHz, CDCl$_3$): δ 1.36 and 1.45(9H, s), 1.83(1H, m), 1.95–2.40(5H, m), 2.45–2.57(1H, m), 3.07(1H, m), 3.55–3.78(2H, m), 4.28 and 4.39(1H, s), 4.52(1H, m), 4.82–4.95(1H, m).

MASS (ES+) m/z: 334 (M+1).

EXAMPLE 22-2

(2S)-1-{[(1R,3S,4S)-6-Oxo-2-azabicyclo[2.2.1]hept-3-yl]carbonyl}-2-pyrrolidinecarbonitrile hydrochloride The title compound was prepared from tert-butyl (1R,3S,4S)-3-{[(2S)-2-cyano-1-pyrrolidinyl]carbonyl}-6-oxo-2-azabicyclo[2.2.1]heptane-2-carboxylate obtained in Example 22-1 in a similar manner to that of Example 2-8.

$^1$H-NMR (300 MHz, DMSO-d$_6$): δ 1.44(1H, m), 1.80–2.38(5H, m), 3.05(1H, m), 3.35–4.0(3H, m), 4.45(1H, m), 4.64(1H, m), 4.79–4.91(2H, m).

MASS (ES+) m/z: 234 (M+1)

EXAMPLE 23-1 tert-Butyl (1R,3S,4S,6R)-3-{[(2S)-2-cyano-1-pyrrolidinyl]carbonyl}-6-{[(2S)-2,3-dihydroxypropyl]oxy}-2-azabicyclo[2.2.1]heptane-2-carboxylate The title compound was prepared from tert-butyl (1R,3S,4S,6R)-6-allyloxy-3-{[(2S)-2-cyano-1-pyrrolidinyl]carbonyl}-2-azabicyclo[2.2.1]heptane-2-carboxylate obtained in Example 16-1 in a similar manner to that of Example 21-1.

$^1$H-NMR (300 MHz, CDCl$_3$): δ 1.34 and 1.46(9H, s), 1.65(1H, m), 1.77(1H, m), 2.05–2.37(6H, m), 2.53(1H, m), 2.73(1H, m), 3.50–3.77(6H, m), 3.79–3.98(2H, m), 4.17–4.38(2H, m), 4.84(1H, m).

MASS (ES+) m/z: 410 (M+1).

EXAMPLE 23-2

(2S)-1-[((1R,3S,4S,6R)-6-{[(2S)-2,3-Dihydroxypropyl]oxy}-2-azabicyclo[2.2.1]hept-3-yl)carbonyl]-2-pyrrolidinecarbonitrile hydrochloride The title compound was prepared from tert-butyl (1R,3S,4S,6R)-3-{[(2S)-2-cyano-1-pyrrolidinyl]carbonyl}-6-{[(2S)-2,3-dihydroxypropyl]oxy}-2-azabicyclo[2.2.1]heptane-2-carboxylate obtained in Example 23-1 in a similar manner to that of Example 2-8.

$^1$H-NMR (300 MHz, DMSO-d$_6$): δ 1.43(1H, m), 1.64(1H, m), 1.70–2.32(6H, m), 3.04(1H, m), 3.20–3.96(9H, m), 4.34(1H, m), 4.83(1H, m).

MASS (ES+) m/z: 310 (M+1).

EXAMPLE 24-1 tert-Butyl (1R,3S,4S,6S)-3-{[(2S)-2-cyano-1-pyrrolidinyl]carbonyl}-6-hydroxy-2-azabicyclo[2.2.1]heptane-2-carboxylate To a solution of tert-butyl (1R,3S,4S)-3-{[(2S)-2-cyano-1-pyrrolidinyl]carbonyl}-6-oxo-2-azabicyclo[2.2.1]heptane-2-carboxylate obtained in Example 22-1 (80 mg) in methanol (8 mL), was added sodium borohydride (1 mg). The mixture was stirred at 0° C. for 1 hr. To the reaction mixture, was added citric acid solution. The mixture was extracted with ethyl acetate. The combined organic phase was washed with brine, dried over sodium sulfate, and evaporated in vacuo. The residue was triturated with ether to give the target compound (82 mg) as a solid.

$^1$H-NMR (300 MHz, CDCl$_3$): δ 1.38 and 1.46(9H, s), 1.63(1H, m), 1.77(1H, m), 1.91(1H, m), 2.05–2.41(5H, m), 2.74(1H, m), 3.55–3.75(2H, m), 4.15–4.48(3H, m), 4.90(1H, m).

MASS (ES+) m/z: 336 (M+1).

EXAMPLE 24-2

(2S)-1-{[(1R,3S,4S,6S)-6-hydroxy-2-azabicyclo[2.2.1]hept-3-yl]carbonyl}-2-pyrrolidinecarbonitrile hydrochloride The title compound was prepared from tert-butyl (1R,3S,4S,6S)-3-{[(2S)-2-cyano-1-pyrrolidinyl]carbonyl}-6-hydroxy-2-azabicyclo[2.2.1]heptane-2-carboxylate obtained in Example 24-1 in a similar manner to that of Example 2-8.

$^1$H-NMR (300 MHz, DMSO-d$_6$): δ 0.91 (H, m), 1.85–2.35(7H, m), 2.98(1H, br-s), 3.46(1H, m), 3.70(1H, m), 3.83(1H, m), 4.26(1H, m), 4.48(1H, m), 4.86(1H, m), 5.75(1H, d, J=4 Hz).

MASS (ES+) m/z: 236 (M+1)

EXAMPLE 25-1 tert-Butyl (1R,3S,4S,6R)-3-{[(2S)-2-cyano-1-pyrrolidinyl]carbonyl}-6-(2-oxoethoxy)-2-azabicyclo[2.2.1]heptane-2-carboxylate To a solution of tert-butyl (1R,3S,4S,6R)-3-{[(2S)-2-cyano-1-pyrrolidinyl]carbonyl}-6-{[(2S)-2,3-dihydroxypropyl]oxy}-2-azabicyclo[2.2.1]heptane-2-carboxylate obtained in Example 23–1 (250 mg) in methanol (5 mL) and water (5 mL), was added sodium periodinate (522 mg). The mixture was stirred at room temperature for 20 minutes. The reaction mixture was diluted with ethyl acetate, and washed successively with water and brine. The organic phase was dried over sodium sulfate and evaporated in vacuo to give the target compound (238 mg). This compound was used immediately without purification.

EXAMPLE 25-2 tert-Butyl (1R,3S,4S,6R)-3-{[(2S)-2-cyano-1-pyrrolidinyl]carbonyl}-6-(2-hydroxyethoxy)-2-azabicyclo[2.2.1]heptane-2-carboxylate To a solution of tert-butyl (1R,3S,4S,6R)-3-{[(2S)-2-cyano-1-pyrrolidinyl]carbonyl}-6-(2-oxoethoxy)-2-azabicyclo[2.2.1]heptane-2-carboxylate obtained in Example 25-1 (238 mg) in methanol (6 mL), was added sodium borohydride (26.2 mg). The mixture was stirred at room temperature for 20 minutes. To the resulting mixture, was added citric acid solution. The mixture evaporated in vacuo. The residue was diluted with ethyl acetate, and washed with water and brine. The organic phase was dried over sodium sulfate and evaporated in vacuo to give the target compound (220 mg).

$^1$H-NMR (300 MHz, CDCl$_3$): δ 1.35 and 1.46(9H, s), 1.66(1H, m), 1.78(1H, m), 2.05–2.37(6H, m), 2.72(1H, m), 3.52–3.67(4H, m), 3.71(2H, m), 3.93(1H, m), 4.17–4.38(2H, m), 4.85(1H, m).

MASS (ES+) m/z: 380 (M+1).

EXAMPLE 25-3

(2S)-1-{[(1R,3S,4S,6R)-6-(2-hydroxyethoxy)-2-azabicyclo[2.2.1]hept-3-yl]carbonyl}-2-pyrrolidinecarbonitrile hydrochloride The title compound was prepared from tert-butyl (1R,3S,4S,6R)-3-{[(2S)-2-cyano-1-pyrrolidinyl]carbonyl}-6-(2-hydroxyethoxy)-2-azabicyclo[2.2.1]heptane-2-carboxylate obtained in Example 25-2 in a similar manner to that of Example 2-8.

$^1$H-NMR (300 MHz, DMSO-d$_6$): δ 1.42(1H, m), 1.64(1H, m), 1.70–2.32(6H, m), 3.04(1H, m), 3.30–3.75(5H, m), 3.82(1H, m), 3.93(1H, s), 4.33(1H, m), 4.83(1H, m).

MASS (ES+) m/z: 280 (M+1).

EXAMPLE 26-1 tert-Butyl (1R,3S,4S,6E)-6-[(benzyloxy)imino]-3-{[(2S)-2-cyano-1-pyrrolidinyl]carbonyl}-2-azabicyclo[2.2.1]heptane-2-carboxylate The title compound was prepared from tert-butyl (1R,3S,4S)-3-{[(2S)-2-cyano-1-pyrrolidinyl]carbonyl}-6-oxo-2-azabicyclo[2.2.1]heptane-2-carboxylate obtained in Example 22-1 in a similar manner to that of Example 28-1 described later.

$^1$H-NMR (300 MHz, CDCl$_3$): δ 1.37 and 1.43(9H, s), 1.68(1H, m), 1.88(1H, m), 2.04–2.36(5H, m), 2.65(1H, m), 2.94(1H, m), 3.57–3.75(4H, m), 4.41(1H, m), 4.65–4.95(2H, m), 5.10(2H, m), 7.20–7.39(5H, m).

MASS (ES+) m/z: 439 (M+1).

EXAMPLE 26-2

(2S)-1-({(1R,3S,4S,6E)-6-[(Benzyloxy)imino]-2-azabicyclo[2.2.1]hept-3-yl}carbonyl)-2-pyrrolidinecarbonitrile hydrochloride The title compound was prepared from tert-butyl (1R,3S,4S,6E)-6-[(benzyloxy)imino]-3-{[(2S)-2-cyano-1-pyrrolidinyl]carbonyl}-2-azabicyclo[2.2.1]heptane-2-carboxylate obtained in Example 26-1 in a similar manner to that of Example 2-8.

$^1$H-NMR (300 MHz, DMSO-d$_6$): δ 1.90–2.55(8H, m), 3.31(1H, m), 3.66(2H, t, J=7 Hz), 4.41(1H, s), 4.55(1H, m), 4.84(1H, m), 5.04–5.17(2H, m), 7.26–7.40(5H, m).

MASS (ES+) m/z: 339 (M+1).

EXAMPLE 27-1 tert-Butyl (1R,3S,4S,6R)-6-[2-({[5-(acetylamino)-1,3,4-thiadiazol-2-yl]sulfonyl}amino)-2-oxoethoxy]-3-{[(2S)-2-cyano-1-pyrrolidinyl]carbonyl}-2-azabicyclo[2.2.1]heptane-2-carboxylate The title compound was prepared from [((1R,3S,4S,6R)-2-(tert-butoxycarbonyl)-3-{[(2S)-2-cyano-1-pyrrolidinyl]carbonyl}-2-azabicyclo[2.2.1]hept-6-yl)oxy]acetic acid obtained in Example 15-2 in a similar manner to that of Example 18-1.

$^1$H-NMR (300 MHz, CDCl$_3$): δ 1.26 and 1.36(9H, s), 1.22(1H, m), 1.50–1.67(2H, m), 1.84(1H, m), 1.95–2.30(4H, m), 2.20 and 2.23(3H, s), 2.77(1H, m), 3.17(1H, d, J=5 Hz), 3.37–3.75(5H, m), 4.09(1H, m), 4.24(1H, m), 4.36(1H, t, J=5 Hz), 4.88(1H, m).

MASS (ES−) m/z: 596 (M−1).

EXAMPLE 27-2

N-{[5-(Acetylamino)-1,3,4-thiadiazol-2-yl]sulfonyl}-2-[((1R,3S,4S,6R)-3-{[(2S)-2-cyano-1-pyrrolidinyl]carbonyl}-2-azabicyclo[2.2.1]hept-6-yl)oxy]acetamide hydrochloride The title compound was prepared from tert-butyl (1R,3S,4S,6R)-6-[2-({[5-(acetylamino)-1,3,4-thiadiazol-2-yl]sulfonyl}amino)-2-oxoethoxy]-3-{[(2S)-2-cyano-1-pyrrolidinyl]carbonyl}-2-azabicyclo[2.2.1]heptane-2-carboxylate obtained in Example 27-1 in a similar manner to that of Example 2-8.

$^1$H-NMR (300 MHz, DMSO-d$_6$): δ 1.47(1H, m), 1.65(1H, m), 1.75–2.29(6H, m), 2.25(3H, s), 3.03(1H, m), 3.62(2H, m), 3.84–4.13(4H, m), 4.33(1H, m), 4.82(1H, m).

MASS (ES+) m/z: 498 (M+1).

EXAMPLE 28-1 tert-Butyl (1R,3S,4S,6E)-3-{[(2S)-2-cyano-1-pyrrolidinyl]carbonyl}-6-hydroxyimino-2-azabicyclo[2.2.1]heptane-2-carboxylate To a solution of tert-butyl (1R,3S,4S)-3-{[(2S)-2-cyano-1-pyrrolidinyl]carbonyl}-6-oxo-2-azabicyclo[2.2.1]heptane-2-carboxylate obtained in Example 22-1 (296 mg) in ethanol (5 mL) and water (1 mL),were added hydroxylamine hydrochloride (123 mg) and sodium acetate (153 mg). The mixture was stirred at 80° C. for 20 minutes.

The resulting mixture was evaporated in vacuo. To the residue, was added water. The mixture was extracted with ethyl acetate. The combined organic phase was washed with brine, dried over sodium sulfate, and evaporated in vacuo. The residue was chromatographed on silica gel eluting with chloroform and methanol (19:1) to give the target compound (106 mg) as a solid.

$^1$H-NMR (300 MHz, CDCl$_3$): δ 1.36 and 1.45(9H, s), 1.71(1H, m), 1.90(1H, m), 2.05–2.38(5H, m), 2.66(1H, m), 2.97(1H, m), 3.55–3.74(2H, m), 4.44(1H, m), 4.67 and 4.77(1H, s), 4.90(1H, m), 7.02(1H, br-s).

MASS (ES+) m/z: 349 (M+1).

EXAMPLE 28-2

(2S)-1-{[(1R,3S,4S,6Z)-6-hydroxyimino-2-azabicyclo[2.2.1]hept-3-yl]carbonyl}-2-pyrrolidinecarbonitrile hydrochloride The title compound was prepared from tert-butyl (1R,3S,4S,6E)-3-{[(2S)-2-cyano-1-pyrrolidinyl]carbonyl}-6-hydroxyimino-2-azabicyclo[2.2.1]heptane-2-carboxylate obtained in Example 28-1 in a similar manner to that of Example 2-8.
$^1$H-NMR (300 MHz, DMSO-d$_6$): δ 1.87–2.43(8H, m), 3.28(1H, m),3.66(2H, t, J=7 Hz),4.35(1H, s),4.53(1H, m),4.83(1H, m).
MASS (ES+) m/z: 249 (M+1).

EXAMPLE 29-1

2-tert-Butyl 3-methyl (1R,3S,4S,6R)-6-[(methylsulfonyl)oxy]-2-azabicyclo[2.2.1]heptane-2,3-dicarboxylate To a solution of 2-tert-butyl 3-methyl (1R,3S,4S,6R)-6-hydroxy-2-azabicyclo[2.2.1]heptane-2,3-dicarboxylate (185 mg) in pyridine (2 mL), was added methanesulfonyl chloride (117 mg). The mixture was stirred at room temperature for 2 hrs. The resulting mixture was evaporated in vacuo. To the residue, water was added. The mixture was extracted with ethyl acetate. The combined organic phase was washed with brine, dried over sodium sulfate, and evaporated in vacuo. The residue was chromatographed on silica gel eluting with hexane and ethyl acetate (1:1) to give the target compound (237 mg).
$^1$H-NMR (300 MHz, CDCl$_3$): δ 1.39 and 1.48(9H, s), 1.58–1.88(3H, m), 2.83(1H, m), 3.04 and 3.06(3H, s), 3.75 (3H, s), 4.12(1H, m), 4.45(1H, br-s), 4.84(1H, m).
MASS (ES+) m/z: 350 (M+1).

EXAMPLE 29-2

2-tert-Butyl 3-methyl (1R,3S,4S,6R)-6-azido-2-azabicyclo[2.2.1]heptane-2,3-dicarboxylate To a solution of 2-tert-butyl 3-methyl (1R,3S,4S,6R)-6-[(methylsulfonyl)oxy]-2-azabicyclo[2.2.1]heptane-2,3-dicarboxylate obtained in Example 29-1 (232 mg) in dimethylformamide (2.0 mL) and water (0.4 mL), was added sodium azide (108 mg). The mixture was stirred at 80° C. for 1 hr. The resulting mixture was diluted with ethyl acetate, and washed successively with water and brine. The organic layer was dried over sodium sulfate and evaporated in vacuo. The residue was chromatographed on silica gel eluting with hexane and ethyl acetate (4:1) to give the target compound (175 mg).
$^1$H-NMR (300 MHz, CDCl$_3$): δ 1.40 and 1.49(9H, s), 1.40–1.71(3H, m), 1.87–2.02(2H, m), 2.72(1H, m), 3.63–3.77(1H, m), 3.73(3H, s), 4.10–4.33(1H, m).
MASS (ES+) m/z: 297 (M+1).

EXAMPLE 29-3

2-tert-butyl 3-methyl (1R,3S,4R,6R)-6-amino-2-azabicyclo[2.2.1]heptane-2,3-dicarboxylate To a solution of 2-tert-butyl 3-methyl (1R,3S,4S,6R)-6-azido-2-azabicyclo[2.2.1]heptane-2,3-dicarboxylate obtained in Example 29-2 (170 mg) in methanol (4 mL), was added 10% palladium on carbon (30 mg). The mixture was stirred under 1 atm of hydrogen for 1.5 hrs at room temperature. The resulting mixture was filtered through celite and washed with methanol. The filtrate and washings were evaporated in vacuo to give the target compound (155 mg).

EXAMPLE 29-4

2-tert-Butyl 3-methyl (1R,3S,4R,6R)-6-acetylamino-2-azabicyclo[2.2.1]heptane-2,3-dicarboxylate To a solution of 2-tert-butyl 3-methyl (1R,3S,4R,6R)-6-amino-2-azabicyclo[2.2.1]heptane-2,3-dicarboxylate obtained in Example 29-3 (155 mg) in methanol (10 mL), was added acetic anhydride (30 mg). The mixture was stirred at room temperature for 1 hr. The resulting mixture was evaporated in vacuo and chromatographed on silica gel eluting with chloroform and methanol (19:1) to give the target compound (153 mg).
$^1$H-NMR (300 MHz, CDCl$_3$): δ 1.39 and 1.51(9H, s), 1.30–1.55(2H, m), 1.95 and 1.97(3H, s), 2.04–2.20(2H, m), 2.71(1H, m), 3.67–3.80(1H, m), 3.73(3H, s), 3.98–4.28(2H, m).
MASS (ES+) m/z: 313 (M+1).

EXAMPLE 29-5

(1R,3S,4R,6R)-6-Acetylamino-2-(tert-butoxycarbonyl)-2-azabicyclo[2.2.1]heptane-3-carboxylic acid The title compound was prepared from tert-butyl 3-methyl (1R,3S,4R,6R)-6-acetylamino-2-azabicyclo[2.2.1]heptane-2,3-dicarboxylate obtained in Example 29-4 in a similar manner to that of Example 5-6.
$^1$H-NMR (300 MHz, DMSO-d$_6$): δ 1.32 and 1.41(9H, s), 1.33–1.50(2H, m), 1.68(1H, m), 1.78(3H, s), 1.92(1H, m), 2.59(1H, m), 3.57(1H, s), 3.70–3.98(2H, m), 7.74(1H, m)
MASS (ES−) m/z: 297 (M−1).

EXAMPLE 29-6 tert-Butyl (1R,3R,4R,6R)-6-acetylamino-3-{[(2S)-2-cyano-1-pyrrolidinyl]carbonyl}-2-azabicyclo[2.2.1]heptane-2-carboxylate The title compound was prepared from (1R,3S,4R,6R)-6-acetylamino-2-(tert-butoxycarbonyl)-2-azabicyclo[2.2.1]heptane-3-carboxylic acid obtained in Example 29-5 in a similar manner to that of Example 5-7.
$^1$H-NMR (300 MHz, CDCl$_3$): δ 1.35 and 1.49(9H, s), 1.4–1.6(2H, m), 1.98(3H, s), 2.0–2.42(6H, m), 2.60(1H, m), 3.55–3.82(3H, m), 4.00–4.25(2H, m), 4.83(1H, m), 5.25(1H, m).
MASS (ES+) m/z: 377 (M+1).

EXAMPLE 29-7

N-((1R,3S,4S,6R)-3-{[(2S)-2-Cyano-1-pyrrolidinyl]carbonyl}-2-azabicyclo[2.2.1]hept-6-yl)acetamide hydrochloride The title compound was prepared from tert-butyl (1R,3R,4R,6R)-6-acetylamino-3-{[(2S)-2-cyano-1-pyrrolidinyl]carbonyl}-2-azabicyclo[2.2.1]heptane-2-carboxylate obtained in Example 29-6 in a similar manner to that of Example 2-8.

¹H-NMR (300 MHz, DMSO-d₆): δ 1.32–1.65(2H, m), 1.67–2.32(6H, m), 1.83(3H, s),2.96(1H, m), 3.58–3.70(2H, m), 3.83(1H, m), 4.07(1H, m), 4.17(1H, m), 4.80(1H, dd, J=5.1, 8.1 Hz), 8.14(1H, d, J=8 Hz), 8.53(1H, m).

MASS (ES+) m/z: 277 (M+1).

EXAMPLE 30-1

3-Benzyl 2-tert-butyl (1R,3S,4S,6R)-6-hydroxy-2-azabicyclo[2.2.1]heptane-2,3-dicarboxylate To a solution of (1R,3S,4S,6R)-2-(tert-butoxycarbonyl)-6-hydroxy-2-azabicyclo[2.2.1]heptane-3-carboxylic acid obtained in Example 5-6 (1.0 g) in dichloromethane (8 mL), were added benzyl alcohol (504 mg), dicyclohexylcarbodiimide (962 mg) and 4-(dimethylamino)pyridine (12 mg). The mixture was stirred at room temperature for 20 hrs.

The resulting mixture was filtered through celite and washed with dichloromethane. The filtrate and washings were evaporated in vacuo. The residue was chromatographed on silica gel eluting with hexane and ethyl acetate (1:1) to give the target compound (597 mg).

¹H-NMR (300 MHz, CDCl₃): δ 1.32 and 1.46(9H, s), 1.60–2.03(3H, m), 2.77(1H, m), 4.07–4.22(3H, m), 5.06–5.28(2H, m), 7.25–7.37(5H, m).

MASS m/z: 370 (M+Na).

EXAMPLE 30-2

3-Benzyl 2-tert-butyl (1R,3S,4S,6R)-6-{[(1E)-3-ethoxy-3-oxo-1-propen-1-yl]oxy}-2-azabicyclo[2.2.1]heptane-2,3-dicarboxylate To a solution of 3-benzyl 2-tert-butyl (1R,3S,4S,6R)-6-hydroxy-2-azabicyclo[2.2.1]heptane-2,3-dicarboxylate obtained in Example 30-1 (593 mg) in dichloromethane (10 mL), were added ethyl propiolate (670 mg) and 4-methylmorpholine (190 mg). The mixture was stirred at room temperature for 3 hrs. The resulting mixture was evaporated in vacuo and the residue was chromatographed on silica gel eluting with hexane and ethyl acetate (4:1) to give the target compound (760 mg).

¹H-NMR (300 MHz, CDCl₃): δ 1.26(3H, m), 1.34 and 1.50(9H, s), 1.42(1H, m), 1.63–1.78(2H, m), 1.97(1H, m), 2.82(1H, m), 4.07–4.43(5H, m), 5.07–5.37(3H, m), 7.28–7.42(5H, m), 7.48(1H, m).

EXAMPLE 30-3

(1R,3S,4S,6R)-2-(tert-Butoxycarbonyl)-6-(3-ethoxy-3-oxopropoxy)-2-azabicyclo[2.2.1]heptane-3-carboxylic acid To a solution of 3-benzyl 2-tert-butyl (1R,3S,4S,6R)-6-{[(1E)-3-ethoxy-3-oxo-1-propen-1-yl]oxy}-2-azabicyclo[2.2.1]heptane-2,3-dicarboxylate obtained in Example 30-2 (316 mg) in ethanol (8 mL), was added 10% palladium on carbon (60 mg). The mixture was stirred under 4 atm of hydrogen for 1 hr at room temperature. The resulting mixture was filtered through celite and washed with ethanol. The filtrate and washings were evaporated in vacuo and the residue was chromatographed on silica gel eluting with chloroform and methanol (19:1) to give the target compound (210 mg).

¹H-NMR (300 MHz, DMSO-d₆): δ 1.26(3H, t, J=7 Hz), 1.3–1.55(1H, m), 1.59(1H, m), 1.73(1H, m), 2.06(1H, m), 2.54(2H, t, J=6 Hz), 2.84(1H, m), 3.61–3.81(3H, m), 4.09–4.18(3H, m), 4.35(1H, m).

EXAMPLE 30-4 tert-Butyl (1R,3R,4S,6R)-3-{[(2S)-2-cyano-1-pyrrolidinyl]carbonyl}-6-(3-ethoxy-3-oxopropoxy)-2-azabicyclo[2.2.1]heptane-2-carboxylate The title compound was prepared from (1R,3S,4S,6R)-2-(tert-butoxycarbonyl)-6-(3-ethoxy-3-oxopropoxy)-2-azabicyclo[2.2.1]heptane-3-carboxylic acid obtained in Example 30-3 in a similar manner to that of Example 5-7.

¹H-NMR (300 MHz, CDCl₃): δ 1.27(3H, m), 1.34 and 1.47(9H, s), 1.44(1H, m), 1.63(1H, m), 1.76(1H, m), 2.05–2.38(5H, m), 2.54(2H, m), 2.68(1H, m), 3.50–3.93(5H, m), 4.09–4.38(4H, m), 4.85(1H, m).

EXAMPLE 30-5

Ethyl 3-[((1R,3R,4S,6R)-3-{[(2S)-2-cyano-1-pyrrolidinyl]carbonyl}-2-azabicyclo[2.2.1]hept-6-yl)oxy] propionate hydrochloride The title compound was prepared from tert-butyl (1R,3R,4S,6R)-3-{[(2S)-2-cyano-1-pyrrolidinyl]carbonyl}-6-(3-ethoxy-3-oxopropoxy)-2-azabicyclo[2.2.1]heptane-2-carboxylate obtained in Example 30-4 in a similar manner to that of Example 2-8.

¹H-NMR (300 MHz, DMSO-d₆): δ 1.18(1H, t, J=7 Hz), 1.37(1H, m), 1.62(1H, m), 1.73(1H, m), 1.84(1H, m), 1.90–2.32(4H, m), 2.53(2H, m), 3.03(1H, m), 3.54–3.75(4H, m), 3.81(1H, m), 3.92(1H, br-s), 4.07(2H, q, J=7 Hz), 4.33(1H, m), 4.83(1H, dd, J=5, 8 Hz).

MASS (ES+) m/z: 336 (M+1).

EXAMPLE 31

Ethyl [((1R,3S,4S,6R)-3-{[(2S)-2-cyano-1-pyrrolidinyl]carbonyl}-2-azabicyclo[2.2.1]hept-6-yl)oxy] acetate hydrochloride The title compound was prepared from tert-butyl (1R,3S,4S,6R)-3-{[(2S)-2-cyano-1-pyrrolidinyl]carbonyl}-6-(2-ethoxy-2-oxoethoxy)-2-azabicyclo[2.2.1]heptane-2-carboxylate obtained in Example 15-1 in a similar manner to that of Example 2-8.

¹H-NMR (300 MHz, DMSO-d₆): δ 1.22(1H, t, J=7 Hz), 1.48(1H, m), 1.68(1H, m), 1.81(1H, m), 1.93–2.32(5H, m), 3.05(1H, br-s), 3.53–3.71(2H, m), 3.90(1H, m), 4.02(1H, br-s), 4.07–4.20(4H, m), 4.33(1H, m), 4.82(1H, dd, J=5, 8 Hz).

MASS (ES+) m/z: 322 (M+1).

EXAMPLE 32-1 tert-Butyl (1R,3S,4S,6R)-3-{[(2S)-2-cyano-1-pyrrolidinyl]carbonyl}-6-{[(2E)-2-(hydroxyimino)ethyl]oxy}-2-azabicyclo[2.2.1]heptane-2-carboxylate To a solution of tert-butyl (1R,3S,4S,6R)-3-{[(2S)-2-cyano-1-pyrrolidinyl]carbonyl}-6-(2-oxoethoxy)-2-azabicyclo[2.2.1]heptane-2-carboxylate obtained in Example 25-1 (163 mg) in ethanol (6 mL) and water (1 mL), were added hydroxylamine hydrochloride (36 mg) and sodium acetate (46 mg). The mixture was stirred at reflux for 20 minutes. To the resulting mixture, brine was added. The mixture extracted with ethyl acetate. The combined organic phase was washed with brine, dried over sodium sulfate, and evaporated in vacuo. The residue was chromatographed on silica gel eluting with ethyl acetate to give the target compound (131 mg).

$^1$H-NMR (300 MHz, CDCl$_3$): δ 1.35 and 1.47(9H, s), 1.3–1.5(1H, m), 1.65(1H, m), 1.80(1H, m), 2.05–2.37(5H, m), 2.72(1H, m), 3.49–3.67(2H, m), 3.93(1H, m), 4.07–4.26 (3H, m), 4.85(1H, m), 6.85 and 7.46(1H, m).

MASS (ES+) m/z: 393 (M+1).

EXAMPLE 32-2

(2S)-1-[((1R,3S,4S,6R)-6-{[(2E)-2-(hydroxyimino) ethyl]oxy}-2-azabicyclo[2.2.1]hept-3-yl)carbonyl]-2-pyrrolidinecarbonitrile hydrochloride The title compound was prepared from tert-butyl (1R,3S, 4S,6R)-3-{[(2S)-2-cyano-1-pyrrolidinyl]carbonyl}-6-{ [(2E)-2-(hydroxyimino)ethyl]oxy}-2-azabicyclo[2.2.1]heptane-2-carboxylate obtained in Example 32-1 in a similar manner to that of Example 2-8.

$^1$H-NMR (300 MHz, DMSO-d$_6$): δ 1.4–2.32(8H, m), 3.06(7H, m), 3.5–4.4(5H, m), 4.83(1H, m), 6.78 and 7.36 (1H, m).

MASS (ES+) m/z: 293 (M+1).

EXAMPLE 33-1

2-tert-Butyl 3-methyl (1R,3S,4R,6R)-6-[(tert-butoxycarbonyl)amino]-2-azabicyclo[2.2.1]heptane-2, 3-dicarboxylate The title compound was prepared from 2-tert-butyl 3-methyl (1R,3S,4R,6R)-6-amino-2-azabicyclo[2.2.1]heptane-2, 3-dicarboxylate obtained in Example 29-3 in a similar manner to that of Example 29-4.

$^1$H-NMR (300 MHz, CDCl$_3$): δ 1.39 and 1.50(9H, s), 1.45(9H, s), 1.30–1.55(2H, m), 1.93(1H, m), 2.06(1H, m), 2.77(1H, m), 3.7–3.83(1H, m), 3.72 and 3.73(3H, s), 4.03–4.40(2H, m).

MASS (ES+) m/z: 371 (M+1).

EXAMPLE 33-2

(1R,3S,4R,6R)-2-(tert-Butoxycarbonyl)-6-[(tert-butoxycarbonyl)amino]-2-azabicyclo[2.2.1]heptane-3-carboxylic acid The title compound was prepared from 2-tert-butyl 3-methyl (1R,3S,4R,6R)-6-[(tert-butoxycarbonyl)amino]-2-azabicyclo[2.2.1]heptane-2,3-dicarboxylate obtained in Example 33-1 in a similar manner to that of Example 5-6.

$^1$H-NMR (300 MHz, DMSO-d$_6$): δ 1.32 and 1.42(9H, s), 1.39(9H, s), 1.2–1.54(2H, m), 1.62(1H, m), 1.87(1H, m), 2.53(1H, m), 3.45–3.58(2H, m), 3.77–3.96(1H, m), 6.89(1H, m).

MASS (ES–) m/z: 355 (M–1).

EXAMPLE 33-3 tert-Butyl (1R,3R,4R,6R)-6-[(tert-butoxycarbonyl) amino]-3-{[(2S)-2-cyano-1-pyrrolidinyl]carbonyl}-2-azabicyclo[2.2.1]heptane-2-carboxylate The title compound was prepared from (1R,3S,4R,6R)-2-(tert-butoxycarbonyl)-6-[(tert-butoxycarbonyl)amino]-2-azabicyclo[2.2.1]heptane-3-carboxylic acid obtained in Example 33-2 in a similar manner to that of Example 5-7.

$^1$H-NMR (300 MHz, CDCl$_3$): δ 1.35 and 1.48(9H, s), 1.45(9H, s), 1.33–1.53(2H, m), 1.97–2.37(6H, m), 2.58(1H, m), 3.56–3.88(4H, m), 4.09(1H, m), 4.34(1H, m), 4.83(1H, m).

MASS (ES+) m/z: 435 (M+1).

EXAMPLE 33-4

(2S)-1-{[(1R,3S,4R,6R)-6-Amino-2-azabicyclo [2.2.1]hept-3-yl]carbonyl}-2-pyrrolidinecarbonitrile dihydrochloride The title compound was prepared from tert-butyl (1R,3R, 4R,6R)-6-[(tert-butoxycarbonyl)amino]-3-{[(2S)-2-cyano-1-pyrrolidinyl]carbonyl}-2-azabicyclo[2.2.1]heptane-2-carboxylate obtained in Example 33-3 in a similar manner to that of Example 2-8.

$^1$H-NMR (300 MHz, DMSO-d$_6$): δ 1.53(1H, m), 1.67–2.32(7H, m), 3.06(1H, m), 3.45–3.71(2H, m), 3.89(1H, m), 4.12(1H, m), 4.26(1H, m), 4.80(1H, dd, J=5, 8 Hz).

MASS (ES+) m/z: 235 (M+1).

EXAMPLE 34-1

2-tert-Butyl 3-methyl (1R,3S,4S,6R)-6-{[(4-methylphenyl)sulfonyl]amino}-2-azabicyclo[2.2.1]heptane-2,3-dicarboxylate To a solution of 2-tert-butyl 3-methyl (1R,3S,4R,6R)-6-amino-2-azabicyclo[2.2.1]heptane-2,3-dicarboxylate obtained in Example 29-3 (321 mg) in pyridine (4 mL), was added p-toluenesulfonyl chloride (249 mg). The mixture was stirred at room temperature for 1 hr. The resulting mixture was evaporated in vacuo, and the residue chromatographed on silica gel eluting with hexane and ethyl acetate (1:1) to give the target compound (440 mg)

$^1$H-NMR (300 MHz, CDCl$_3$): δ 1.37 and 1.47(9H, s), 1.30–1.55(2H, m), 1.84–1.99(2H, m), 2.44(3H, s), 2.61–2.74(1H, m), 3.26–3.68(2H, m), 3.70(3H, s), 4.06–4.50(2H, m), 7.33(2H, d, J=8 Hz), 7.75–7.85(2H, m).

MASS (ES+) m/z: 425 (M+1).

EXAMPLE 34-2

(1R,3S,4S,6R)-2-(tert-Butoxycarbonyl)-6-{[(4-methylphenyl)sulfonyl]amino}-2-azabicyclo[2.2.1]heptane-3-carboxylic acid The title compound was prepared from 2-tert-butyl 3-methyl (1R,3S,4S,6R)-6-{[(4-methylphenyl)sulfonyl]amino}-2-azabicyclo[2.2.1]heptane-2,3-dicarboxylate obtained in Example 34-1 in a similar manner to that of Example 5-6.

$^1$H-NMR (300 MHz, CDCl$_3$): δ 1.23–1.92(4H, m), 1.51 (9H, s), 2.45(3H, s), 2.94(1H, m), 3.35(1H, m), 3.67(1H, m), 4.15(1H, m), 4.68(1H, m), 7.33(2H, d, J=8 Hz), 7.77(2H, d, J=8 Hz).

MASS (ES–) m/z: 409 (M–1).

EXAMPLE 34-3 tert-Butyl (1R,3R,4S,6R)-3-{[(2S)-2-cyano-1-pyrrolidinyl]carbonyl}-6-{[(4-methylphenyl)sulfonyl]amino}-2-azabicyclo[2.2.1]heptane-2-carboxylate The title compound was prepared from (1R,3S,4S,6R)-2-(tert-butoxycarbonyl)-6-{[(4-methylphenyl)sulfonyl]amino}-2-azabicyclo[2.2.1]heptane-3-carboxylic acid obtained in Example 34-2 in a similar manner to that of Example 5-7.

$^1$H-NMR (300 MHz, CDCl$_3$): δ 1.35–1.48(2H, m), 1.43 (9H, s), 1.91(1H, m), 2.05–2.28(5H, m), 2.44(3H, s), 2.55 (1H, m), 3.38(1H, m), 3.42–3.73(3H, m), 4.11(1H, m), 4.65(1H, m), 4.80(1H, m), 7.32(2H, d, J=8 Hz), 7.78(2H, d, J=8 Hz).

MASS (ES−) m/z: 487 (M−1).

EXAMPLE 34-4

N-((1R,3S,4S,6R)-3-{[(2S)-2-Cyano-1-pyrrolidinyl]carbonyl}-2-azabicyclo[2.2.1]hept-6-yl)-4-methyl-benzenesulfonamide hydrochloride The title compound was prepared from tert-butyl (1R,3R,4S,6R)-3-{[(2S)-2-cyano-1-pyrrolidinyl]carbonyl}-6-{[(4-methylphenyl)sulfonyl]amino}-2-azabicyclo[2.2.1]heptane-2-carboxylate obtained in Example 34-3 in a similar manner to that of Example 2-8.

$^1$H-NMR (300 MHz, DMSO-d$_6$): δ 1.37–1.50(2H, m), 1.70–2.30(6H, m), 2.41(3H, s), 2.88(1H, m), 3.57(2H, m), 3.67–3.81(2H, m), 3.98(1H, s), 4.77(1H, dd, J=5, 8 Hz), 7.44(2H, d, J=8 Hz), 7.74(2H, d, J=8 Hz), 7.97(1H, d, J=7 Hz).

MASS (ES+) m/z: 389 (M+1).

EXAMPLE 35-1 tert-Butyl (1R,3S,4S,6R)-6-(2-tert-butoxy-2-oxoethoxy)-3-{[(2S)-2-cyano-1-pyrrolidinyl]carbonyl}-2-azabicyclo[2.2.1]heptane-2-carboxylate To a solution of tert-butyl (1R,3S,4S,6R)-3-{[(2S)-2-cyano-1-pyrrolidinyl]carbonyl}-6-hydroxy-2-azabicyclo[2.2.1]heptane-2-carboxylate obtained in Example 5-7 (322 mg) in dichloromethane (6 mL), were added rhodium acetate dimer (4.24 mg) and tert-butyl diazoacetate (0.27 mL). The mixture was stirred at room temperature for 4 hrs. The resulting mixture was evaporated in vacuo and the residue was chromatographed on silica gel eluting with ethyl acetate to give the target compound (236 mg).

$^1$H-NMR (300 MHz, CDCl$_3$): δ 1.43(1H, m), 1.47(9H, s), 1.49(9H, s), 1.64(1H, m), 1.90(1H, m), 2.05–2.38(5H, m), 2.72(1H, m), 3.55–3.67(2H, m), 3.85–4.05(3H, m), 4.19(1H, m), 4.32(1H, m), 4.84(1H, m).

MASS (ES+) m/z: 450 (M+1).

EXAMPLE 35-2

[((1R,3S,4S,6R)-3-{[(2S)-2-Cyano-1-pyrrolidinyl]carbonyl}-2-azabicyclo[2.2.1]hept-6-yl)oxy]acetic acid hydrochloride The title compound was prepared from tert-butyl (1R,3S,4S,6R)-6-(2-tert-butoxy-2-oxoethoxy)-3-{[(2S)-2-cyano-1-pyrrolidinyl]carbonyl}-2-azabicyclo[2.2.1]heptane-2-carboxylate obtained in Example 35-1 in a similar manner to that of Example 2-8.

$^1$H-NMR (300 MHz, DMSO-d$_6$): δ 1.30–2.35(8H, m), 3.05(1H, m), 3.45(1H, m), 3.63(1H, m), 3.78–4.11(4H, m), 4.32(1H, m), 4.83(1H, m).

MASS (ES+) m/z: 294 (M+1).

EXAMPLE 36-1 tert-Butyl (1R,3S,4S,6R)-3-{[(2S)-2-cyano-1-pyrrolidinyl]carbonyl}-6-[2-oxo-2-(2-pyridinylamino)ethoxy]-2-azabicyclo[2.2.1]heptane-2-carboxylate The title compound was prepared from [(((1R,3S,4S,6R)-2-(tert-butoxycarbonyl)-3-{[(2S)-2-cyano-1-pyrrolidinyl]carbonyl}-2-azabicyclo[2.2.1]hept-6-yl)oxy]acetic acid obtained in Example 15-2 in a similar manner to that of Example 15-3.

$^1$H-NMR (300 MHz, CDCl$_3$): δ 1.35 and 1.47(9H, s), 1.47(1H, m), 1.73(1H, m), 1.86(1H, m), 2.08–2.38(5H, m), 2.77(1H, m), 3.53–3.69(2H, m), 3.99–4.42(5H, m), 4.85(1H, m), 7.07(1H, m), 7.73(1H, m), 8.25(1H, d, J=8 Hz), 8.29 (1H, m), 8.75(1H, br-s).

MASS (ES+) m/z: 470 (M+1).

EXAMPLE 36-2

2-[((1R,3S,4S,6R)-3-{[(2S)-2-cyano-1-pyrrolidinyl]carbonyl}-2-azabicyclo[2.2.1]hept-6-yl)oxy]-N-2-pyridinylacetamide Dihydrochloride The title compound was prepared from tert-butyl (1R,3S,4S,6R)-3-{[(2S)-2-cyano-1-pyrrolidinyl]carbonyl}-6-[2-oxo-2-(2-pyridinylamino)ethoxy]-2-azabicyclo[2.2.1]heptane-2-carboxylate obtained in Example 36-1 in a similar manner to that of Example 2-8.

$^1$H-NMR (300 MHz, DMSO-d$_6$): δ 1.4–2.32(8H, m), 3.08(1H, m), 3.56–4.10(4H, m), 4.20–4.37(3H, m), 4.83(1H, dd, J=5, 8 Hz), 7.26(1H, m), 7.96(1H, m), 8.07(1H, m), 8.37(1H, m).

MASS (ES+) m/z: 370 (M+1).

EXAMPLE 37-1

Ethyl (1S,4R,5S,7S,8S)-8-bromo-4-hydroxy-6-[(1R)-1-phenylethyl]-6-azabicyclo[3.2.1]octane-7-carboxylate The title compound was prepared from ethyl (1S,3S,4R)-2-[(1R)-1-phenylethyl]-2-azabicyclo-[2.2.2]oct-5-ene-3-carboxylate obtained in Example 2-2 in a similar manner to that of Example 5-2.

$^1$H-NMR (300 MHz, CDCl$_3$): δ 1.26(3H, t, J=7 Hz), 1.41(3H, d, J=7 Hz), 1.42–1.55(2H, m), 2.12–2.41(2H, m), 2.46(1H, d, J=11 Hz), 2.77(1H, m), 3.32(1H, m), 3.47(1H, m), 3.80(1H, d, J=7 Hz), 4.96–4.06(2H, m), 4.17(2H, m), 7.20–7.35(3H, m), 7.49(2H, d, J=7 Hz).

MASS (ES+) m/z: 382, 384 (M+1).

EXAMPLE 37-2

Ethyl (1R,4R,5R,7S)-4-hydroxy-6-[(1R)-1-phenylethyl]-6-azabicyclo[3.2.1]octane-7-carboxylate The title compound was prepared from ethyl (1S,4R,5S, 7S,8S)-8-bromo-4-hydroxy-6-[(1R)-1-phenylethyl]-6- azabicyclo[3.2.1]octane-7-carboxylate obtained in Example 37-1 in a similar manner to that of Example 5-3.

¹H-NMR (300 MHz, CDCl₃): δ 1.24(3H, t, J=7 Hz), 1.22–1.49(3H, m), 1.38(3H, d, J=7 Hz),1.64(1H, m), 1.99 (1H, d, J=11 Hz), 2.30(1H, m), 2.61(1H, m), 3.13(1H, m), 3.49(1H, m), 3.84(1H, d, J=5 Hz), 3.97(1H, q, J=7 Hz), 4.13(2H, m), 7.17–7.33(3H, m), 7.54(2H, d, J=7 Hz).

MASS (ES+) m/z: 304 (M+1).

EXAMPLE 37-3

Ethyl (1R,4R,5R,7S)-4-hydroxy-6-azabicyclo[3.2.1]octane-7-carboxylate

The title compound was prepared from ethyl (1R,4R,5R,7S)-4-hydroxy-6-[(1R)-1-phenylethyl]-6-azabicyclo[3.2.1]octane-7-carboxylate obtained in Example 37-2 in a similar manner to that of Example 2-4.

EXAMPLE 37-4

6-tert-Butyl 7-ethyl (1R,4R,5R,7S)-4-hydroxy-6-azabicyclo[3.2.1]octane-6,7-dicarboxylate The title compound was prepared from ethyl (1R,4R,5R,7S)-4-hydroxy-6-azabicyclo[3.2.1]octane-7-carboxylate obtained in Example 37-3 in a similar manner to that of Example 5-5.

¹H-NMR (300 MHz, CDCl₃): δ 1.29(3H, m), 1.23–1.50 (2H, m), 1.41 and 1.47(9H, s), 1.66(1H, m), 1.80(1H, m), 2.20(1H, m), 2.34(1H, m), 2.64(1H, m), 4.03–4.37(5H, m).

MASS (ES+) m/z: 300 (M+1).

EXAMPLE 37-5

(1R,4R,5R,7S)-6-(tert-Butoxycarbonyl)-4-hydroxy-6-azabicyclo[3.2.1]octane-7-carboxylic acid The title compound was prepared from 6-tert-butyl 7-ethyl (1R,4R,5R,7S)-4-hydroxy-6-azabicyclo[3.2.1]octane-6,7-dicarboxylate obtained in Example 37-4 in a similar manner to that of Example 5-6.

¹H-NMR (300 MHz, CDCl₃): δ 1.16(1H, m), 1.43 and 1.47(9H, s), 1.54–1.75(3H, m), 1.78–1.95(2H, m), 2.09(1H, m), 2.4–2.7(2H, m), 3.95–4.15(3H, m).

MASS (ES–) m/z: 270 (M–1).

EXAMPLE 37-6 tert-Butyl (1R,4R,5R,7S)-7-{[(2S)-2-cyano-1-pyrrolidinyl]carbonyl}-4-hydroxy-6-azabicyclo[3.2.1]octane-6-carboxylate The title compound was prepared from (1R,4R,5R,7S)-6-(tert-butoxycarbonyl)-4-hydroxy-6-azabicyclo[3.2.1]octane-7-carboxylic acid obtained in Example 37-5 in a similar manner to that of Example 5-7.

¹H-NMR (300 MHz, CDCl₃): δ 1.44 and 1.46(9H, s), 1.50–2.53(12H, m), 3.35–3.88(2H, m), 4.01–4.29(3H, m), 2.73(1H, m), 4.67–4.83(1H, m).

MASS (ES+) m/z: 350 (M+1).

EXAMPLE 37-7

(2S)-1-{[(1R,4R,5R,7S)-4-hydroxy-6-azabicyclo[3.2.1]oct-7-yl]carbonyl}-2-pyrrolidinecarbonitrile hydrochloride The title compound was prepared from tert-butyl (1R,4R,5R,7S)-7-{[(2S)-2-cyano-1-pyrrolidinyl]carbonyl}-4-hydroxy-6-azabicyclo[3.2.1]octane-6-carboxylate obtained in Example 37-6 in a similar manner to that of Example 2-8.

¹H-NMR (300 MHz, DMSO-d₆): δ 1.38–2.35(10H, m), 2.66(1H, m), 3.3–3.5(1H, m), 3.84–3.95(2H, m), 4.01(1H, m), 4.52(1H, s), 4.82(1H, m).

MASS (ES+) m/z: 250 (M+1).

EXAMPLE 38-1 tert-Butyl (1R,3S,4S,6R)-3-{[(2S)-2-cyano-1-pyrrolidinyl]carbonyl}-6-(2-pyridinyloxy)-2-azabicyclo[2.2.1]heptane-2-carboxylate To a solution of tert-butyl (1R,3S,4S,6R)-3-{[(2S)-2-cyano-1-pyrrolidinyl]carbonyl}-6-hydroxy-2-azabicyclo[2.2.1]heptane-2-carboxylate obtained in Example 5-7 (209 mg) in dimethylformamide (2.5ml), were added 2-fluoropyridine (109 mg) and sodium hydride (60% in mineral oil, 25 mg). The mixture was then stirred at room temperature for 50 minutes. The reaction mixture was diluted with ethyl acetate, and washed successively with water and brine. The organic phase was dried over sodium sulfate and evaporated in vacuo. The residue was chromatographed on silica gel eluting with ethyl acetate to give the target compound (162 mg).

¹H-NMR (300 MHz, CDCl₃): δ 1.37, 1.46 and 1.49(9H, s), 1.55(1H, m), 1.72(1H, m), 1.96(1H, m), 2.08–2.42(5H, m), 2.68–2.83(1H, m), 3.45–3.83(2H, m), 4.24–4.34(1H, m), 4.45–4.53(1H, m), 4.73–5.05(1H, m), 5.13(1H, m), 6.76(1H, m), 6.86(1H, m), 7.57(1H, m), 8.17(1H, m).

MASS (ES+) m/z: 413 (M+1).

EXAMPLE 38-2

(2S)-1-{[(1R,3S,4S,6R)-6-(2-pyridinyloxy)-2-azabicyclo[2.2.1]hept-3-yl]carbonyl}-2-pyrrolidinecarbonitrile dihydrochloride The title compound was prepared from tert-butyl (1R,3S,4S,6R)-3-{[(2S)-2-cyano-1-pyrrolidinyl]carbonyl}-6-(2-pyridinyloxy)-2-azabicyclo[2.2.1]heptane-2-carboxylate obtained in Example 38-1 in a similar manner to that of Example 2-8.

¹H-NMR (300 MHz, DMSO-d₆): δ 1.42–1.61(1H, m), 1.85–2.35(7H, m), 3.05–3.17(1H, m), 3.40–3.88(2H, m), 4.03(1H, m), 4.35–4.52(1H, m), 4.84–4.98(1H, m), 5.14–5.28(1H, m), 6.84(1H, m), 7.04(1H, m), 7.74(1H, m), 8.19(1H, m).

MASS (ES+) m/z: 313 (M+1).

EXAMPLE 39-1 tert-Butyl (1R,3S,4S,6R)-6-[(5-cyano-2-pyridinyl)oxy]-3-{[(2S)-2-cyano-1-pyrrolidinyl]carbonyl}-2-azabicyclo[2.2.1]heptane-2-carboxylate The title compound was prepared from tert-butyl (1R,3S, 4S,6R)-3-{[(2S)-2-cyano-1-pyrrolidinyl]carbonyl}-6-hydroxy-2-azabicyclo[2.2.1]heptane-2-carboxylate obtained in Example 5-7 in a similar manner to that of Example 38-1.

$^1$H-NMR (300 MHz, CDCl$_3$): δ 1.36, 1.46 and 1.49(9H, s), 1.52(1H, m), 1.76(1H, m), 1.92(1H, m), 2.07–2.44(5H, m), 2.70–2.84(1H, m), 3.53–3.84(2H, m), 4.25–4.35(1H, m), 4.42–4.53(1H, m), 4.72–4.97(1H, m), 5.28(1H, m), 6.78(1H, m), 7.78(1H, m), 8.47(1H, m).

MASS (ES+) m/z: 438 (M+1).

EXAMPLE 39-2

6-[((1R,3S,4S,6R)-3-{[(2S)-2-Cyano-1-pyrrolidinyl] carbonyl}-2-azabicyclo[2.2.1]hept-6-yl)oxy]nicotinonitrile dihydrochloride The title compound was prepared from tert-butyl (1R,3S, 4S,6R)-6-[(5-cyano-2-pyridinyl)oxy]-3-{[(2S)-2-cyano-1-pyrrolidinyl]carbonyl}-2-azabicyclo[2.2.1]heptane-2-carboxylate obtained in Example 39-1 in a similar manner to that of Example 2-8.

$^1$H-NMR (300 MHz, DMSO-d$_6$): δ 1.45–1.67(1H, m), 1.85–2.35(7H, m), 3.06–3.18(1H, m), 3.35–3.88(2H, m), 4.08(1H, m), 4.35–4.52(1H, m), 4.84–4.98(1H, m), 5.20–5.35(1H, m), 7.04(1H, m), 8.21(1H, m), 8.74(1H, m).

MASS (ES+) m/z: 338 (M+1).

EXAMPLE 40-1

2-tert-Butyl 3-methyl (1R,3S,4S,6R)-6-[(phenoxycarbonothioyl)oxy]-2-azabicyclo[2.2.1]heptane-2,3-dicarboxylate To a solution of 2-tert-butyl 3-methyl (1R,3S,4S, 6R)-6-hydroxy-2-azabicyclo[2.2.1]heptane-2,3-dicarboxylate (4.5 g) in pyridine (10 mL), was added O-phenyl chlorothiocarbonate (3.15 g). The mixture was then stirred at room temperature for 3 hrs. The resulting mixture was evaporated in vacuo. To the residue, water was added. The mixture was extracted with ethyl acetate. The combined organic phase was washed successively with diluted hydrochloric acid, sodium hydrogen carbonate solution and brine, dried over sodium sulfate, and evaporated in vacuo. The residue was chromatographed on silica gel eluting with hexane and ethyl acetate (2:1) to give the target compound (5.22 g).

$^1$H-NMR (300 MHz, CDCl$_3$): δ 1.41 and 1.47(9H, s), 1.58–1.92(3H, m), 2.24(1H, m), 2.88(1H, m), 3.76(3H, s), 4.17(1H, m), 4.58(1H, m), 5.34(1H, m), 7.09(2H, m), 7.29(1H, m), 7.43(2H, m).

MASS (ES+) m/z: 408 (M+1).

EXAMPLE 40-2

2-tert-Butyl 3-methyl (1S,3S,4R)-2-azabicyclo[2.2.1]heptane-2,3-dicarboxylate

The title compound was prepared from 2-tert-butyl 3-methyl (1R,3S,4S,6R)-6-[(phenoxycarbonothioyl)oxy]-2-azabicyclo[2.2.1]heptane-2,3-dicarboxylate obtained in Example 40-1 in a similar manner to that of Example 5-3.

$^1$H-NMR (300 MHz, CDCl$_3$): δ 1.39 and 1.46(9H, s), 1.23–1.72(5H, m), 1.85(1H, m), 2.77(1H, m), 3.74(3H, s), 4.17–4.40(2H, m).

MASS (ES+) m/z: 256 (M+1).

EXAMPLE 40-3

(1S,3S,4R)-2-(tert-Butoxycarbonyl)-2-azabicyclo[2.2.1]heptane-3-carboxylic acid

The title compound was prepared from 2-tert-butyl 3-methyl (1S,3S,4R)-2-azabicyclo[2.2.1]heptane-2,3-dicarboxylate obtained in Example 40-2 in a similar manner to that of Example 5-6.

$^1$H-NMR (300 MHz, DMSO-d$_6$): δ 1.26–1.65(6H, m), 1.32 and 1.38(9H, s), 2.68(1H, m), 4.03(1H, m), 4.15(1H, m).

MASS (ES–) m/z: 240 (M–1).

EXAMPLE 40-4 tert-Butyl (1S,3S,4R)-3-{[(2S)-2-cyano-1-pyrrolidinyl]carbonyl}-2-azabicyclo[2.2.1]heptane-2-carboxylate The title compound was prepared from (1S,3S, 4R)-2-(tert-butoxycarbonyl)-2-azabicyclo[2.2.1]heptane-3-carboxylic acid obtained in Example 40-3 in a similar manner to that of Example 5-7.

$^1$H-NMR (300 MHz, CDCl$_3$): δ 1.35 and 1.45(9H, s), 1.36–1.55(3H, m), 1.62–1.75(2H, m), 1.91(1H, m), 2.05–2.37(4H, m), 2.68–2.78(1H, m), 3.50–3.67(2H, m), 4.1–4.4(2H, m), 4.88(1H, m).

MASS (ES+) m/z: 320 (M+1).

EXAMPLE 40-5

(2S)-1-[(1S,3S,4R)-2-Azabicyclo[2.2.1]hept-3-ylcarbonyl]-2-pyrrolidinecarbonitrile hydrochloride The title compound was prepared from tert-butyl (1S,3S, 4R)-3-{[(2S)-2-cyano-1-pyrrolidinyl]carbonyl}-2-azabicyclo[2.2.1]heptane-2-carboxylate obtained in Example 40-4 in a similar manner to that of Example 2-8.

$^1$H-NMR (300 MHz, DMSO-d$_6$): δ 1.15–1.38(1H, m), 1.52–2.35(9H, m), 3.05(1H, br-s), 3.64–3.71(2H, m), 3.95(1H, m), 4.37(1H, m), 4.84(1H, m).

MASS (ES+) m/z: 220 (M+1).

EXAMPLE 41-1 tert-Butyl (1R,3S,4S,6R)-3-{[(2S)-2-cyano-1-pyrrolidinyl]carbonyl}-6-(4-nitrophenoxy)-2-azabicyclo[2.2.1]heptane-2-carboxylate The title compound was prepared from tert-butyl (1R,3S, 4S,6R)-3-{[(2S)-2-cyano-1-pyrrolidinyl]carbonyl}-6-hydroxy-2-azabicyclo[2.2.1]heptane-2-carboxylate obtained in Example 5-7 in a similar manner to that of Example 38-1.

$^1$H-NMR (300 MHz, CDCl$_3$): δ 1.48 and 1.1.52(9H, s), 1.55(1H, m), 1.74–1.93(2H, m), 2.08–2.50(5H, m), 2.75(1H, m), 3.44–3.88(2H, m), 4.31–4.52(1H, m), 4.68–4.81(2H, m), 7.03–7.11(2H, m), 8.16–8.24(2H, m).

MASS (ES+) m/z: 457 (M+1).

EXAMPLE 41-2

(2S)-1-{[(1R,3S,4S,6R)-6-(4-Nitrophenoxy)-2-azabicyclo[2.2.1]hept-3-yl]carbonyl}-2-pyrrolidinecarbonitrile bonitrile hydrochloride The title compound was prepared from tert-butyl (1R,3S, 4S,6R)-3-{[(2S)-2-cyano-1-pyrrolidinyl]carbonyl}-6-(4-nitrophenoxy)-2-azabicyclo[2.2.1]heptane-2-carboxylate obtained in Example 41-1 in a similar manner to that of Example 2-8.

$^1$H-NMR (300 MHz, DMSO-d$_6$): δ 1.66(1H, m), 1.84–2.33(7H, m), 3.13(1H, m), 3.48(1H, m), 3.84(1H, m), 4.04(1H, m), 4.50(1H, m), 4.77(1H, m), 4.91(1H, m), 7.26 (2H, m), 8.26(2H, m).

MASS (ES+) m/z: 357 (M+1).

EXAMPLE 42-1

Methyl (2Z)-{[(1R)-1-phenylethyl]imino}acetate

To a solution of 2-hydroxy-2-methoxyacetic acid methyl ester (151 g) in toluene (300 mL), was added (R)-(+)-1-phenylethylamine (150 g) dropwise. The mixture was then stirred for 1 hr at room temperature. The resulting mixture was extracted with ethyl acetate. The organic layer was washed with water and brine, dried over magnesium sulfate, and evaporated to obtain the target compound as a yellow oil. The target compound was used in the next step without further purification.

$^1$H-NMR (300 MHz, CDCl$_3$): δ 1.63(3H, d, J=6. 6 Hz), 3.87(3H, s), 4.61(1H, dq, J=6. 6, 0.7 Hz), 7.22–7.36(5H, m),7.75(1H, d, J=0.7 Hz).

EXAMPLE 42-2

Methyl (1S,3S,4R)-2-[(1R)-1-phenylethyl]-2-azabicyclo[2.2.1]hept-5-ene-3-carboxylate To a solution of methyl (2Z)-{[(1R)-1-phenylethyl]imino}acetate obtained in Example 42-1 (238 g) in 2,2,2-trifluoroethanol, was added trifluoromethylacetic acid (95.9 mL) at −10° C. The mixture was then stirred at the same temperature. After 1 hr, cyclopentadiene was added dropwise at −10° C. over 30 minutes.

The mixture was stirred at the same temperature and then the solution was concentrated. The residue was diluted with 3N hydrochloric acid (1200 mL) and washed with ether. The ether layer was extracted with 3N hydrochloric acid (300 mL). The combined aqueous layer was basified with 28% ammonium hydroxide (300 mL) and extracted with ethyl acetate (×2, 1200 mL+200 mL). The combined organic layer was washed with brine, dried over MgSO$_4$, and concentrated to obtain a crude oil.

The crude oil was placed in a refrigerator overnight. The solid which crystallized from the oil was washed with pre-cooled hexane to obtain yellow crystal (96.4 g). The mother liquid was evaporated and placed in a refrigerator 2 days. The solid which crystallized from the liquid was washed similarly to obtain yellow crystal (12.4 g). The mother liquid (c.a. 180 g) was purified by short column chromatography on silica gel eluting with 10% ethyl acetate/hexane to give an colorless oil, which was crystallized in a refrigerator and washed similarly (×2) to obtain colorless crystal (24.0g, 18.3 g).

$^1$H-NMR (300 MHz, CDCl$_3$): δ 1.35–1.47(1H, m), 1.42 (3H, d, J=6.6 Hz), 2.06–2.13(1H, m), 2.18–2.23(1H, m), 2.86–2.93(1H, m), 3.04(1H, q, J=6.6 Hz), 3.35(3H, s), 4.31(1H, s), 6.21–6.30(1H, m), 6.37–6.45(1H, m), 7.11–7.32(5H, m).

MASS m/z: 258.25.

EXAMPLE 42-3

Methyl (1S,3S,4S,6R,7S)-6-acetyloxy-7-iodo-2-[(1R)-1-phenylethyl]-2-azabicyclo[2.2.1]heptane-3-carboxylate To a solution of methyl (1S,3S,4R)-2-[(1R)-1-phenylethyl]-2-azabicyclo[2.2.1]hept-5-ene-3-carboxylate obtained in Example 42-2 (1.0 g) in acetic acid (9 mL), was added portionwise 1,3-diiodo-5,5-dimethylhydantoin (782 mg). The mixture was stirred at room temperature for 30 minutes. The solution was concentrated under reduced pressure. The resulting mixture was diluted with ethyl acetate, and washed successively with sodium hydrogencarbonate solution, sodium thiosulfate solution, sodium hydrogen carbonate solution and brine. The organic layer was dried over MgSO$_4$ and evaporated in vacuo to give the target compound as a solid (1.74 g).

$^1$H-NMR (300 MHz, CDCl$_3$): δ 1.42(3H, d, J=6 Hz), 2.05(3H, s), 2.02–2.15(2H, m), 2.66–2.72(1H, m), 3.30–3.40(1H, m), 3.46(3H, s), 3.67(1H, s), 3.72(1H, q, J=6 Hz), 3.83(1H, s), 4.88–4.95(1H, m), 7.20–7.31(5H, m).

MASS (ES+) m/z: 444.0 (M+1).

EXAMPLE 42-4

Methyl (1R,3S,4S,6R)-6-acetyloxy-2-[(1R)-1-phenylethyl]-2-azabicyclo[2.2.1]heptane-3-carboxylate A solution of methyl (1S,3S,4S,6R,7S)-6-acetyloxy-7-iodo-2-[(1R)-1-phenylethyl]-2-azabicyclo[2.2.1]heptane-3-carboxylate obtained in Example 42-3 (1.73 g) in methanol (20 mL) containing 20% Pd(OH)$_2$ (173 mg) and triethylamine (0.6 mL) was stirred at room temperature for 1.5 hrs under 1 atm pressure with hydrogen.

The reaction mixture was filtered through a bed of Celite and concentrated. The residue was diluted with ethyl acetate, and washed successively with sodium hydrogencarbonate solution, sodium thiosulfate solution, sodium hydrogencarbonate solution and brine. The organic layer was dried over MgSO$_4$ and evaporated in vacuo to give the target compound as a brawn oil (1.28 g).

$^1$H-NMR (300 MHz, CDCl$_3$): δ 1.23–1.32(1H, m), 1.40 (3H, d, J=6 Hz), 1.45–1.56(2H, m), 1.99(3H, s), 2.00–2.08 (1H, m), 2.60(1H, br-s), 3.35(1H, d, J=2 Hz), 3.43(1H, s), 3.49(3H, s), 3.71(1H, q, J=6 Hz), 4.84(1H, d, J=7 Hz), 7.19–7.38(5H, m).

MASS (ES+) m/z: 318.2 (M+1).

EXAMPLE 42-5

Methyl (1R,3S,4S,6R)-6-acetyloxy-2-azabicyclo [2.2.1]heptane-3-carboxylate

A solution of methyl (1R,3S,4S,6R)-6-acetyloxy-2-[(1R)-1-phenylethyl]-2-azabicyclo[2.2.1]heptane-3-carboxylate obtained in Example 42-4 (1.25 g) in methanol (20 mL) containing 20% Pd(OH)$_2$ (250 mg) was stirred at room temperature for 17 hrs under 4 atm pressure with hydrogen.

The reaction mixture was filtered through a bed of Celite and concentrated. The residue was dissolved with 1N hydrochloric acid and washed with diethylether. The aqueous phase was basified with sodium hydrogencarbonate and extracted with chloroform. The organic layer was dried over MgSO$_4$ and evaporated in vacuo. The residue was dissolved with methanol (20 mL) containing 20% Pd(OH)$_2$ (160 mg) was stirred at room temperature for 3 hrs under 4 atm pressure with hydrogen. The reaction mixture was filtered through a bed of Celite and concentrated to give the target compound as an oil (750 mg).

¹H-NMR (300 MHz, CDCl₃): δ 1.38–1.47(1H, m), 1.68–1.85(4H, m), 2.01(3H, m), 2.69(1H, br-s), 3.43(1H, s), 3.75(3H, s), 3.74–3.78(1H, m), 4.62–4.68(1H, m).

MASS (ES+) m/z: 214.2 (M+1).

EXAMPLE 42-6

(1R,3S,4S,6R)-2-(tert-Butoxycarbonyl)-6-hydroxy-2-azabicyclo[2.2.1]heptane-3-carboxylic acid To a solution of methyl (1R,3S,4S,6R)-6-acetyloxy-2-azabicyclo[2.2.1]heptane-3-carboxylate obtained in Example 42-5 (744 mg) in dioxane (8 mL), was added 1N sodium hydroxide (12.2 mL) at 0° C. The mixture was stirred at the same temperature for 1 hr. To this mixture, di-tert-butyl dicarbonate (777 mg) in dioxane (2 mL) was added. The mixture was then stirred at room temperature for 14 hrs.

The resulting mixture was evaporated in vacuo. To the residue, 1N hydrochloric acid was added, and the mixture was extracted with chloroform (60 mL×2). The combined organic phase was dried over magnesium sulfate and evaporated in vacuo. The residue was triturated with diisopropylether to give the target compound as a white solid (615 mg).

¹H-NMR (300 MHz, DMSO-d₆): δ 1.09–1.20(1H, m), 1.32 and 1.39(9H, s), 1.45–1.55(1H, m), 1.66(1H, d, J=11 Hz), 1.72–1.86(1H, m), 2.58–2.66(1H, m), 3.74–3.82(1H, m), 3.85–3.96(2H, m), 4.96–5.03(1H, m).

MASS (ES−) m/z: 256.2 (M−1).

EXAMPLE 42-7 tert-Butyl (1R,3S,4S,6R)-3-{[(2S)-2-aminocarbonyl-1-pyrrolidinyl]carbonyl}-6-hydroxy-2-azabicyclo[2.2.1]heptane-2-carboxylate To a suspension of (1R,3S,4S,6R)-2-(tert-butoxycarbonyl)-6-hydroxy-2-azabicyclo[2.2.1]heptane-3-carboxylic acid obtained in Example 42-6 (45 g) in chloroform (450 mL), were added (2S)-2-pyrrolidinecarboxamide (21 g), 1-hydroxybenzotriazole hydrate (29.5 g), 1-(3-dimethylaminopropyl)-3-ethylcarbodiimide hydrochloride (36.9 g) and diisopropylethylamine (45.3 g) in water bath. The mixture was stirred at room temperature for 5 hrs. The precipitate collected by vacuum filtration and washed with ethyl acetate to give the target compound as a solid (51.5 g).

¹H-NMR (300 MHz, DMSO-d₆): δ 0.91–1.04(1H, m), 1.24 and 1.35(9H, s), 1.40–1.54(1H, m), 1.58–1.69(1H, m), 1.69–2.05(5H, m), 2.69–2.79(1H, m), 3.45–3.59(2H, m), 3.70–3.88(2H, m), 4.13–4.25(2H, m), 4.79–4.86(1H, m), 6.79–6.89(1H, m), 7.20(1H, br-s).

MASS m/z: 354.

EXAMPLE 42-8 tert-Butyl (1R,3S,4S,6R)-3-{[(2S)-2-cyano-1-pyrrolidinyl]carbonyl}-6-hydroxy-2-azabicyclo[2.2.1]heptane-2-carboxylate To a mixture of tert-butyl (1R,3S,4S,6R)-3-{[(2S)-2-aminocarbonyl-1-pyrrolidinyl]carbonyl}-6-hydroxy-2-azabicyclo[2.2.1]heptane-2-carboxylate obtained in Example 42-7 (53.4 g) and pyridine (71.7 g) in tetrahydrofuran (550 mL), was added trifluoroacetic anhydride (95.2 g) dropwise at 0° C. under nitrogen.

The mixture was stirred at the same temperature for 10 minutes and was then stirred at room temperature for 1.5 hrs. The reaction mixture was adjusted with aqueous sodium hydrogencarbonate solution (ca. 500 mL) to pH8 and concentrated in vacuo. The residue was partitioned between water and chloroform. The organic layer was separated, washed with 0.5 mol/L hydrochloric acid, water and brine, dried over magnesium sulfate, and evaporated in vacuo. The residue was washed with isopropylether, and a mixture of hexane and ethyl acetate (2:1) to give the target compound as a solid (43.5 g).

¹H-NMR (300 MHz, CDCl₃): δ 1.23–1.34(1H, m), 1.34 and 1.46(9H, s), 1.64(1H, d, J=9 Hz), 1.82 and 1.97(1H, d, J=3 Hz), 1.84–1.94(1H, m), 2.03–2.36(5H, m), 2.66–2.76 (1H, m), 3.46–3.69(2H, m), 4.08–4.23(2H, m), 4.23–4.35 (1H, m), 4.76–4.90(1H, m).

MASS m/z: 336.

EXAMPLE 42-9

(2S)-1-{[(1R,3S,4S,6R)-6-hydroxy-2-azabicyclo[2.2.1]hept-3-yl]carbonyl}-2-pyrrolidinecarbonitrile hydrochloride To a solid of tert-butyl (1R,3S,4S,6R)-3-{[(2S)-2-cyano-1-pyrrolidinyl]carbonyl}-6-hydroxy-2-azabicyclo[2.2.1]heptane-2-carboxylate obtained in Example 42-8 (796 mg), was added a mixture of 4N hydrochloride in dioxane (1.87 mL) and water (0.13 mL). The mixture was stirred at room temperature for 5 minutes. The resulting mixture was evaporated in vacuo and the residual solid was washed with isopropyl alcohol. The solid was recrystalized from ethanol-water to give the target compound as a white crystal (367 mg)

¹H-NMR (300 MHz, DMSO-d₆): δ 1.32(1H, m), 1.62(1H, ddd, J=1.8, 6.9, 13.8 HZ), 1.79(1H, m), 1.88–2.33(5H, m), 3.03(1H, br-s), 3.53–3.71(3H, m), 3.97(1H, m), 4.31(1H, m), 4.82(1H, dd, J=5.1, 8.1 Hz), 5.46(1H, d, J=4.2 Hz).

MASS (ES+) m/z: 236 (M+1).

EXAMPLE 43-1

1-Methyl-1,2,3,4-tetrahydro-4-quinolinamine

1-Methyl-2,3-dihydro-4(1H)-quinolinone oxime (360 mg) was dissolved in methanol (25 mL) and 20% Pd(OH)₂ on carbon (100 mg) was added. The mixture was stirred under hydrogen atmosphere at room temperature for 1.5 hrs. The reaction mixture was filtered through a bed of Celite and washed with methanol. The filtrate was concentrated in vacuo to give the target compound as a colorless oil (330 mg)

¹H-NMR (300 MHz, CDCl₃): δ 1.57(2H, br-s), 1.87(1H, m), 2.07(1H, m), 2.91(3H, s), 3.22(1H, m), 3.33(1H, m), 3.98(1H, t, J=4 Hz), 6.62(1H, d, J=8 Hz), 6.67(1H, dd, J=8, 8 Hz), 7.14(1H, dd, J=8, 8 Hz), 7.19(1H, d, J=8 Hz).

EXAMPLE 43-2

(2S,4S)-4-Fluoro-1-{[(1-methyl-1,2,3,4-tetrahydro-4-quinolinyl)amino]acetyl}-2-pyrrolidinecarbonitrile To a solution of 1-methyl-1,2,3,4-tetrahydro-4-quinolinamine obtained in Example 43-1 (329 mg) in tetrahydrofuran (4 mL), were added (2S,4S)-1-chloroacetyl-4-fluoro-2-pyrrolidinecarbonitrile obtained in Example 7-11 (193 mg) and a catalytic amount of NaI. The reaction mixture was stirred for 22 hrs.

The reaction mixture was diluted with tetrahydrofuran (10 mL) and washed with tetrahydrofuran. The combined organic layer was concentrated in vacuo. The residue was purified with silica gel chromatography (SiO$_2$: 25 g, ethyl acetate then methanol/CHCl$_3$=10/0–20/1) to give the target compound as a pale brawn amorphous (137 mg).

$^1$H-NMR (300 MHz, CDCl$_3$): δ 2.15–2.43(1H, m), 2.66 (1H, m), 2.91(3H, s), 3.16(1H, m), 3.31–4.06(1H, m), 4.86–5.50(2H, m), 6.55–6.66(2H, m), 7.05–7.22(2H, m).

MASS (ES+) m/z: 317.2 (M+1).

EXAMPLE 44-1

3,4-Dihydro-2H-chromen-4-ylamine

The title compound was prepared from 4-chromanone oxime in a similar manner to that of Example 43-1.

$^1$H-NMR (300 MHz, CDCl$_3$): δ 1.86(1H, m), 2.16(1H, m), 4.05(1H, m), 4.18–4.33(2H, m), 6.82(1H, d, J=8 Hz), 6.90(1H, dd, J=8, 8 Hz), 7.15(1H, dd, J=8, 8 Hz), 7.30(1H, d, J=8 Hz).

EXAMPLE 44-2

(2S,4S)1-[(3,4-Dihydro-2H-chromen-4-ylamino) acetyl]-4-fluoro-2-pyrrolidinecarbonitrile The title compound was prepared from 3,4-dihydro-2H-chromen-4-ylamine obtained in Example 44–1 in a similar manner to that of Example 43-2.

$^1$H-NMR (300 MHz, CDCl$_3$): δ 1.83–2.07(2H, m), 2.32 (1H, m), 2.70(1H, m), 3.40–3.95(5H, m), 4.16–4.40(2H, m), 4.97(1H, d, J=8 Hz), 5.25–5.52(1H, m), 6.82(1H, d, J=8 Hz), 6.90(1H, dd, J=8, 8 Hz), 7.17(1H, dd, J=8, 8 Hz), 7.35(1H, dd, J=8, 8 Hz).

MASS (ES+) m/z: 304.2 (M+1).

EXAMPLE 45-1 tert-Butyl (1R,3S,4S,6R)-3-{[(2S,4S)-2-aminocarbonyl-4-fluoro-1-pyrrolidinyl]carbonyl}-6-hydroxy-2-azabicyclo[2.2.1]heptane-2-carboxylate The title compound was prepared from (1R,3S,4S,6R)-2-(tert-butoxycarbonyl)-6-hydroxy-2-azabicyclo[2.2.1]heptane-3-carboxylic acid obtained in Example 5-6 in a similar manner to that of Example 5-7.

$^1$H-NMR (300 MHz, CDCl$_3$): δ 1.34–1.15(1H, m), 1.44 (9H, s), 1.61–1.72(1H, m), 1.82–1.94(1H, m), 1.98–3.04 (4H, m), 3.66–4.46(6H, m), 5.11–5.34(1H, m), 5.62–5.77 (1H, m), 6.69–6.76(2H, br-s).

EXAMPLE 45-2 tert-Butyl (1R,3S,4S,6R)-3-{[(2S,4S)-2-cyano-4-fluoro-1-pyrrolidinyl]carbonyl}-6-hydroxy-2-azabicyclo[2.2.1]heptane-2-carboxylate To a solution of tert-butyl (1R,3S,4S,6R)-3-{[(2S,4S)-2-aminocarbonyl-4-fluoro-1-pyrrolidinyl]carbonyl}-6-hydroxy-2-azabicyclo[2.2.1]heptane-2-carboxylate obtained in Example 45-1 (689 mg) in tetrahydrofuran (6.9 mL), was added trifluoroacetic anhydride (0.66 mL) at room temperature.

After stirring for 15 minutes, 1N NaOH (14 mL) was added. After stirring for 10 minutes, the resulting solution was extracted with ethyl acetate. The combined organic layer was washed with saturated aqueous NaCl and dried over MgSO$_4$. After removal of the solvent, the target compound was obtained as a white powder (475 mg). Further purification was not attempted.

$^1$H-NMR (300 MHz, CDCl$_3$): δ 1.20–1.99(13H, m), 2.16–2.46(2H, m), 2.51–2.83(2H, m), 3.80–4.37(5H, m), 4.98–5.10(1H, m), 5.33–5.58(1H, m).

MASS (ES+) m/z: 354.46 (M+1).

EXAMPLE 45-3

(2S,4S)-4-Fluoro-1-{[(1R,3S,4S,6R)-6-hydroxy-2-azabicyclo[2.2.1]hept-3-yl]carbonyl}-2-pyrrolidinecarbonitrile hydrochloride The title compound was prepared from tert-butyl (1R,3S, 4S,6R)-3-{[(2S,4S)-2-cyano-4-fluoro-1-pyrrolidinyl]carbonyl}-6-hydroxy-2-azabicyclo[2.2.1]heptane-2-carboxylate obtained in Example 45-2 in a similar manner to that of Example 2-8.

$^1$H-NMR (300 MHz, DMSO-d$_6$): δ 1.17–1.41(1H, m), 1.55–1.70(1H, m), 1.72–1.85(1H, m), 1.87–2.65(4H, m), 2.99–3.18(1H, m), 3.52–3.70(1H, m), 3.70–3.86(1H, m), 3.86–4.07(2H, m), 4.21(1H, br-s), 5.00–5.19(1H, m), 5.40–5.73(1H, m), 7. 67–8.05(1H, m), 10.16–10.61(1H, m).

EXAMPLE 46-1

Ethyl (3S)-2-azabicyclo[2.2.2]octane-3-carboxylate

A solution of ethyl (1S,3S,4R)-2-[(1R)-1-phenylethyl]-2-azabicyclo[2.2.2]oct-5-ene-3-carboxylate (1.1 g) in ethanol (20 mL) was hydrogenated under H$_2$ atmosphere (4 atm) for 2 hrs. After removal of the catalyst by filtration, the solvent was removed in vacuo to give the target compound as a colorless oil (700 mg).

$^1$H-NMR (CDCl$_3$): δ 1.20(3H, t, J=7.5 Hz), 1.47–2.04 (7H, m), 2.90–3.10(2H, m), 3.73–4.08(2H, m), 4.23(2H, q, J=7.5 Hz)

MASS m/z: 184.25.

EXAMPLE 46-2

(3S)-2-(tert-Butoxycarbonyl)-2-azabicyclo[2.2.2] octane-3-carboxylic acid

Ethyl (3S)-2-azabicyclo[2.2.2]octane-3-carboxylate obtained in Example 46-1 (0.7 g) was dissolved in dioxane (10 mL) and 1N NaOH (7.7 mL) at room temperature, and the reaction mixture was stirred at room temperature for 1 hr. After removal of the organic solvent in vacuo, the aqueous residue was washed with diethylether (10 mL) to remove the impurities, and the aqueous layer was diluted with dioxane (10 mL). To the mixture di-tert-butyl dicarbonate was added (840 mg). The reaction mixture was stirred at room temperature overnight.

The reaction mixture was neutralized with 1N HCl, and the organic solvent was removed in vacuo. The aqueous residue was acidified with 1N HCl. The resulting precipitate was collected by filtration, washed with water to give the target compound as a white powder (200 mg).

$^1$H-NMR (CDCl$_3$): δ 1.44(9H, s), 1.55–2.31(10H, m), 3.98–4.27(2H, m).

MASS m/z: 256.36.

EXAMPLE 46-3 tert-Butyl (3S)-3-{[(2S)-2-aminocarbonyl-1-pyrrolidinyl]carbonyl}-2-azabicyclo[2.2.2]octane-2-carboxylate The title compound was prepared from (3S)-2-(tert-butoxycarbonyl)-2-azabicyclo[2.2.2]octane-3-carboxylic acid obtained in Example 46-2 in a similar manner to that of Example 5-7.

$^1$H-NMR (CDCl$_3$): δ 1.40(9H, s), 1.55–2.31(12H, m), 3.46–3.77(2H, m), 4.00–4.37(2H, m), 4.68–4.75(1H, m), 5.21–5.50(1H, m).

MASS m/z: 352.41.

EXAMPLE 46-4 tert-Butyl (3S)-3-{[(2S)-2-cyano-1-pyrrolidinyl]carbonyl}-2-azabicyclo[2.2.2]octane-2-carboxylate The title compound was prepared from tert-butyl (3S)-3-{[(2S)-2-aminocarbonyl-1-pyrrolidinyl]carbonyl}-2-azabicyclo[2.2.2]octane-2-carboxylate obtained in Example 45-2 in a similar manner to that of Example 5-7.

$^1$H-NMR (CDCl$_3$): δ 1.38(9H, s), 1.50–2.35(13H, m), 3.52–3.78(2H, m), 4.03–4.30(2H, m), 4.85–4.93(1H, m).

MASS m/z: 334.40.

EXAMPLE 46-5

(2S)-1-[(3S)-2-Azabicyclo[2.2.2]oct-3-ylcarbonyl]-2-pyrrolidinecarbonitrile hydrochloride The title compound was prepared from tert-butyl (3S)-3-{[(2S)-2-cyano-1-pyrrolidinyl]carbonyl}-2-azabicyclo[2.2.2]octane-2-carboxylate obtained in Example 46-4 in a similar manner to that of Example 2-8.

$^1$H-NMR (DMSO-d$_6$): δ 1.33–2.35(13H, m), 3.40–3.46 (1H, m), 3.52–3.71(2H, m), 4.20–4.27(1H, m), 4.82–4.90 (1H, m), 8.03(1H, br-s), 9.90(1H, br-s).

MASS (ES+) m/z: 234.30 (M+1).

In order to illustrate the usefulness of the object Compound (I), (1) and (2), the pharmacological test is carried out as shown in the following.

Inhibition Test of Human Plasma DPP-IV (i) Material and Method:

The effect of test compounds on DPP-IV activity in human plasma was evaluated with a modified version of the assay described by Hughes et al (Biochemistry, 38, pp 11597–11603(1999)).

Briefly, 20 μL of human plasma were mixed with 20 μL of 80 mM MgCl$_2$ in assay buffer (25 mM HEPES, 140 mM NaCl, 1% RIA-grade BSA, pH7.8), and were incubated in a room temperature for 60 minutes. Then the reaction was initiated by the addition of both 20 μL of test compounds and 20 μL of 0.2 mM substrate (H-glycine-proline-AMC; AMC is 7-amino-4-methylcoumarine), they were dissolved in the assay buffer.

After 20 minutes incubation in a room temperature (kept in the dark), fluorescence was measured (Excitation 380 nm, Emission 460 nm). A fluorescence-concentration curve of free AMC was obtained using AMC solution in the assay buffer with appropriate concentration. Plasma DPP-IV activities, with or without the test compounds, were expressed as the amount of product per minute per mL. The potency of the test compounds as DPP-IV inhibitor was expressed as IC$_{50}$.

(ii) Results

The following IC$_{50}$ values were obtained.

TABLE 1

| Compound | IC$_{50}$ value for human plasma DPP-IV (nM) |
| --- | --- |
| Example 2-8 | 8.5 |
| Example 5-8 | 8.7 |
| Example 7-12 | 15 |
| Example 10-8 | 13 |
| Example 25-3 | 4.5 |
| Example 45-3 | 4.7 |
| LAF 237 | 24 |

It appeared, from the above-mentioned inhibition test, that the compound (I), (1) and (2) or pharmaceutically acceptable salts thereof of the present invention have an inhibiting activity against DPP-IV.

Therefore, the compound (I), (1) and (2) or pharmaceutically acceptable salts thereof are useful for treating or preventing disease mediated by DPP-IV, more particularly useful for treating or preventing altered glucose tolerance, glucosuria, hyperlipidemia, metabolic acidosis, diabetes mellitus (IDDM and NIDDM), diabetic neuropathy, nephropathy, and secondary diseases in mammals caused by diabetes mellitus.

Further, the compound (I), (1) and (2) or pharmaceutically acceptable salts thereof are useful for treating or preventing autoimmune disease, arthritis, rejection of transplanted organs, systemic lupus erythematosus (SLE), acquired immunodeficiency syndrome (AIDS), hypertension, atherosclerosis, gallbladder disease, cancer, intestinal disease and dwarfism.

The invention claimed is:

1. A compound of the formula (I) or pharmaceutically acceptable salt thereof,

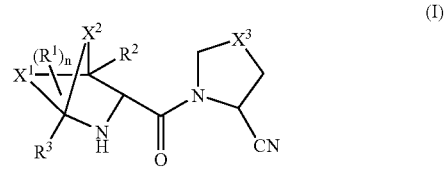

wherein $X^1$ and $X^2$ each is independently lower alkylene;

$X^3$ is =CH$_2$, =CHF or =CF$_2$;

$R^1$ is selected from the group consisting of:

(a) R$^4$O— wherein R$^4$ is H, lower alkyl optionally substituted with substituent α, lower alkenyl, aryl optionally substituted with substituent α, or heteroaryl optionally substituted with substituent α, (b) R$^5$R$^6$N— wherein R$^5$ and R$^6$ each is independently H, lower alkyl, lower alkanoyl, (lower alkyl)sulfonyl, arylsulfonyl optionally substituted with substituent α, or heteroarylsulfonyl optionally substituted with substituent α, (c) R$^7$N= wherein R$^7$ is H, hydroxy, lower alkoxy, aryl(lower alkyl)oxy optionally substituted with substituent α on the aryl group, or heteroaryl(lower alkyl) oxy optionally substituted with substituent α on the heteroaryl group,
(d) saturated heterocyclyl;
(e) carboxy;
(f) sulfonic acid;
(g) halogen; and
(h) oxo;
$R^2$ and $R^3$ are independently H or lower alkyl;
n is 0,1,2,3 or 4 wherein said substituent α is selected from the group consisting of lower alkyl, hydroxyl, lower alkoxy, aryloxy optionally substituted with substituent β, heteroaryloxy optionally substituted with substituent β, amino, (lower alkyl) amino, di(lower alkyl)amino, arylamino optionally substituted with substituent β on the aryl group, heteroarylamino optionally substituted with substituent β on the heteroaryl group, (lower alkyl) sulfonylamino, [halogenated(lower alkyl)[sulfonylamino, arylsulfonylamino optionally substituted with substituent β on the aryl group, heteroarylsulfonylamino optionally substituted with substituent β on the heteroaryl group, di(lower alkyl) aminosulfonylamino, oxo, imino, hydroxyimino, (lower alkyl)sulfonyl, arylsulfonyl optionally substituted with substituent β, heteroarylsulfonyl optionally substituted with substituent β, heteroarylsulfonyl optionally substituted with substituent β, lower alkanoyl, halogen, cyano, nitro and carboxy; and wherein the said substituent β is selected from the group consisting of lower alkyl, hydroxyl, lower atkoxy, amino, (lower alkyl)amino, di(lower alkyl)amino, (lower alkyl)amino, (lower alkanoyl)amino, halogen, cyano, nitro, and carboxy.

2. The compound of claim 1, wherein the said substituent α is selected from the group consisting of:
lower alkyl,
hydroxy,
lower alkoxy,
aryloxy optionally substituted with substituent β,
heteroaryloxy optionally substituted with substituent β,
amino,
(lower alkyl)amino,
di(lower alkyl)amino,
arylamino optionally substituted with substituent β on the aryl group,
heteroarylamino optionally substituted with substituent β on the heteroaryl group,
(lower alkyl)sulfonylamino,
[halogenated(lower alkyl)]sulfonylamino,
arylsulfonylamino optionally substituted with substituent β on the aryl group,
heteroarylsulfonylamino optionally substituted with substituent β on the heteroaryl group,
di(lower alkyl)aminosulfonylamino,
oxo,
imino,
hydroxyimino,
(lower alkyl)sulfonyl,
arylsulfonyl optionally substituted with substituent β,
heteroarylsulfonyl optionally substituted with substituent β,
lower alkanoyl,
halogen,
cyano,
nitro and
carboxy;
the said substituent β is selected from the group consisting of lower alkyl, hydroxy, lower alkoxy, amino, (lower alkyl)amino, di(lower alikyl)amino, (lower alkanoyl) amino, halogen, cyano, nitro and carboxy.

3. The compound of claim 2, wherein $R^1$ is selected from the group consisting of hydroxy, lower alkoxy optionally substituted with hydroxy(s), lower alkenyloxy, amino optionally substituted with substituent lower alkanoyl, halogen, oxo, imino and hydroxyimino.

4. The compound of claim 3, wherein $R^1$ is selected from the group consisting of hydroxy, amino and halogen.

5. The compound of claim 4, wherein $R^1$ is hydroxy.

6. The compound of claim 2, wherein $R^1$ is $R^4O$— wherein $R^4$ is lower alkyl optionally substituted with substituent α aryl optionally substituted with substituent α, or heteroaryl optionally substituted with substituent α,
the said substituent a is selected from the group consisting of hydroxy, arylamino, heteroarylamino, arylsulfonylamino, heteroarylsulfonylamino, oxo, imino, hydroxyimino, lower alkanoyl, halogen, cyano, nitro and carboxy.

7. The compound of claim 2, wherein $R^1$ is lower alkoxy optionally substituted with substituent α,
the said substituent α is selected from the group consisting of hydroxy, lower alkoxy, amino, (lower alkyl) amino, di(lower alkyl)amino, (lower alkyl)sulfonylamino, [halogenated(lower alkyl)]sulfonylamino, di(lower alkyl)aminosulfonylamino, oxo, imino, hydroxyimino and carboxy.

8. The compound of claim 2, wherein $R^1$ is lower alkoxy optionally substituted with substituent α,
the substituent α is selected from the group consisting of heteroarylamino optionally substituted with substituent β on the heteroaryl group, heteroarylsulfonylamino optionally substituted with substituent β on the heteroaryl group and oxo;
the said substituent β is selected from the group consisting of lower alkyl, hydroxy, lower alkoxy, amino, (lower alkyl)amino, di(lower alkyl)amino, lower alkanoyl, halogen, cyano, nitro and carboxy.

9. The compound of claim 2, wherein $R^1$ is selected from the group consisting of aryloxy optionally substituted with substituent α, heteroaryloxy optionally substituted with substituent α, and saturated heterocyclyl;
the said substituent a is selected from the group consisting of lower alkyl, hydroxy, lower alkoxy, amino, (lower alkyl)amino, di(lower alkyl)amino, lower alkanoyl, halogen, cyano, nitro and carboxy.

10. The compound of claim 9, wherein $R^1$ is selected from the group consisting of aryloxy optionally substituted with substituent α, and heteroaryloxy optionally substituted with substituent α,
the said substituent a is selected from the group consisting of lower alkyl, hydroxy, lower alkoxy, amino, (lower alkyl)amino, di(lower alkyl)amino, lower alkanoyl, halogen, cyano, nitro and carboxy.

11. The compound of claim 2, wherein $R^1$ is $R^5R^6N$— wherein $R^5$ and $R^6$ each is independently (lower alkyl)sulfonyl, arylsulfonyl optionally substituted with substituent α, or heteroarylsulfonyl optionally substituted with substituent α;
the said substituent a is selected from the group consisting of lower alkyl, hydroxy, lower alkoxy, amino, (lower alkyl)amino, di(lower alkyl)amino, lower alkanoyl, halogen, cyano, nitro and carboxy.

12. The compound of claim 2, wherein $R^1$ is $R^7N$= wherein $R^7$ is H, hydroxy, lower alkoxy, aryl(lower alkyl) oxy optionally substituted with substituent α on the aryl group;

the said substituent α is selected from the group consisting of lower alkyl, hydroxy, lower alkoxy, amino, (lower alkyl)amino, di(lower alkyl)amino, lower alkanoyl, halogen, cyano, nitro and carboxy.

13. The compound of claim 1, wherein $X^1$ and $X^2$ each is independently (C1–C4)alkylene.

14. The compound of claim 1, wherein $X^1$ and $X^2$ each is independently (C1–C2)alkylene.

15. The compound of claim 1, wherein $X^3$ is =$CH_2$ or =CHF.

16. The compound of claim 1, wherein $X^3$ is =$CH_2$.

17. The compound of claim 1, wherein $R^2$ and $R^3$ each is independently H or (C1–C4)alkyl.

18. The compound of claim 1, wherein $R^2$ and $R^3$ each is independently H or (C1–C2)alkyl.

19. The compound of claim 1, wherein $R^2$ and $R^3$ are H.

20. The compound of claim 1, wherein n is 1, 2, 3 or 4.

21. The compound of claim 1, wherein n is 1 or 2.

22. The compound of claim 1, wherein n is 1.

23. The compound of claim 1, selected from:

(2S)- 1-{[(1S,3S,4S,5S,6R)-5,6-Dihydroxy-2-azabicyclo[2.2.2]oct-3-yl[carbonyl}-2-pyrrolidinecarbonitrile hydrochloride;

(2S)- 1- {[(1S,3S,4S,5R)-5-Hydroxy-2-azabicyclo[2.2.2]oct-3-yl]carbonyl}-2-pyrrolidinecarbonitrile hydrochloride;

(2S)- 1- {[(1R,3S,4S,6R)-6-Hydroxy-2-azabicyclo[2.2.1]hept-3-yl]carbonyl}-2-pyrrolidinecarbonitrile hydrochloride;

(2S)- 1- {[(1R,3S,4S,6S)-6-Hydroxy-2-azabicyclo[2.2.1]hept-3-yl]carbonyl}-2-pyrrolidinecarbonitrile hydrochloride;

(2S)- 1- {[(1R,3S,4S,6R)-6-(2-Hydroxyethoxy)-2- azabicyclo[2.2. 1 ]hept-3-yl]carbonyl}-2- pyrrolidinecarbonitrile hydrochloride;

(2S)- 1- {[(1R,3S,4S,6Z)-6-Hydroxyimino-2-azabicyclo[2.2.1]hept-3-yl]carbonyl}-2-pyrrolidinecarbomtrile hydrochloride;

N-((1R,3S,4S,6R)-3- {[(2S)-2-Cyano- 1-pyrrolidinyl]carbonyl}-2-azabicyclo[2.2.1]hept-6-yl)acetamide hydrochloride;

(2S)- 1- {[(1R,3S,4R,6R)-6-Amino-2-azabicyclo[2.2.1]hept-3-yl]carbonyl}-2-pyrrolidinecarbonitrile dihydrochloride;

(2S)- 1- {[(1R,4R,5R,7S)-4-Hydroxy-6-azabicyclo[3.2.1]oct-7-yl]carbonyl}-2-pyrrolidinecarbonitrile hydrochloride.

24. A method for producing the compound of formula (I) of claim 1, comprising deprotecting the following compound of formula (IV):

wherein $R^{1'}$ is $R^1$ protected not to inhibit this reaction, if needed;
Pro is protective group of amino group.

25. A pharmaceutical composition comprising a compound of claim 1 as an active ingredient, in association with a pharmaceutically acceptable carrier or excipient.

26. A method for treating Non-Insulin Dependent Diabetes Mellitus ("NIDDM") which comprises administering an effective amount of the compound of claim 1 to human beings or animals.

27. A commercial package comprising the pharmaceutical composition containing the compound identified in claim 1 and a written matter associated therewith, wherein the written matter states that the compound (I) can or should be used for treating Non-Insulin Dependent Diabetes Mellitus ("NIDDM").

\* \* \* \* \*